US008476319B2

(12) United States Patent
Scholz et al.

(10) Patent No.: US 8,476,319 B2
(45) Date of Patent: Jul. 2, 2013

(54) METHODS OF TREATING EAR INFECTIONS

(75) Inventors: Matthew T. Scholz, Woodbury, MN (US); Danli Wang, Shoreview, MN (US); Jeffrey F. Andrews, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1130 days.

(21) Appl. No.: 11/908,185

(22) PCT Filed: Mar. 10, 2006

(86) PCT No.: PCT/US2006/008953
§ 371 (c)(1),
(2), (4) Date: May 8, 2008

(87) PCT Pub. No.: WO2006/099325
PCT Pub. Date: Sep. 21, 2006

(65) Prior Publication Data
US 2009/0005339 A1 Jan. 1, 2009

Related U.S. Application Data

(60) Provisional application No. 60/660,593, filed on Mar. 10, 2005.

(51) Int. Cl.
*A61K 31/23* (2006.01)
*C07C 69/533* (2006.01)
*C07C 69/58* (2006.01)
*C07C 69/28* (2006.01)
*C07C 69/30* (2006.01)
*A61K 31/225* (2006.01)

(52) U.S. Cl.
CPC ............. *A61K 31/225* (2013.01); *C07C 69/533* (2013.01); *C07C 69/58* (2013.01); *C07C 69/28* (2013.01); *C07C 69/30* (2013.01)
USPC ............ 514/549; 514/552; 560/224; 560/263

(58) Field of Classification Search
None
See application file for complete search history.

(56) References Cited

U.S. PATENT DOCUMENTS

| 2,818,390 | A |   | 12/1957 | Beaver et al. |
|---|---|---|---|---|
| 3,048,266 | A |   | 8/1962 | Hackhel et al. |
| 3,489,148 | A |   | 1/1970 | Duncan et al. ................ 128/284 |
| 3,806,615 | A |   | 4/1974 | Frankenfeld et al. |
| 3,983,214 | A |   | 9/1976 | Misato et al. |
| 3,985,903 | A |   | 10/1976 | Hasegawa |
| 4,002,775 | A |   | 1/1977 | Kabara |
| 4,010,252 | A |   | 3/1977 | Hewitt |
| 4,067,997 | A |   | 1/1978 | Kabara |
| 4,073,937 | A | * | 2/1978 | Van Cleave ................... 514/552 |
| 4,113,854 | A |   | 9/1978 | Andrews et al. |
| 4,160,820 | A |   | 7/1979 | Wagenknecht et al. |
| 4,189,481 | A |   | 2/1980 | Kabara |
| 4,252,834 | A |   | 2/1981 | Inamine et al. |
| 4,284,653 | A |   | 8/1981 | Shigeoka et al. |
| 4,299,852 | A |   | 11/1981 | Ueno et al. |
| 4,338,342 | A |   | 7/1982 | Tan et al. |
| 4,364,929 | A |   | 12/1982 | Sasmor |
| 4,485,029 | A |   | 11/1984 | Kato et al. |
| 4,512,987 | A |   | 4/1985 | Schindlery et al. |
| 4,557,935 | A |   | 12/1985 | af Ekenstam et al. |
| 4,597,975 | A |   | 7/1986 | Woodward et al. |
| 4,599,233 | A |   | 7/1986 | Misato et al. |
| 4,648,876 | A |   | 3/1987 | Becker et al. |
| 4,722,941 | A |   | 2/1988 | Eckert et al. |
| 4,724,149 | A |   | 2/1988 | Gul et al. |
| 4,840,738 | A |   | 6/1989 | Hardy et al. |
| 4,894,220 | A |   | 1/1990 | Nabi et al. |
| 4,931,282 | A |   | 6/1990 | Asmus et al. |
| 4,962,093 | A |   | 10/1990 | Ohkawa et al. |
| 4,963,555 | A |   | 10/1990 | Jones et al. |
| 4,980,163 | A |   | 12/1990 | Blackburn et al. |
| 4,983,394 | A |   | 1/1991 | Hussein et al. |
| 4,983,595 | A |   | 1/1991 | Benjamin et al. |
| 4,985,242 | A |   | 1/1991 | Sekine et al. |
| 4,997,851 | A |   | 3/1991 | Isaacs et al. |
| 5,084,096 | A |   | 1/1992 | Stovicek |
| 5,093,140 | A |   | 3/1992 | Watanabe |
| 5,098,694 | A |   | 3/1992 | Komp et al. |
| 5,135,910 | A |   | 8/1992 | Blackburn et al. |
| 5,145,685 | A |   | 9/1992 | Carmody |
| 5,188,822 | A |   | 2/1993 | Viccaro et al. |
| 5,192,802 | A |   | 3/1993 | Rencher |
| 5,208,257 | A | * | 5/1993 | Kabara ......................... 514/552 |
| 5,217,950 | A |   | 6/1993 | Blackburn et al. |
| 5,219,887 | A |   | 6/1993 | Andrews et al. |
| 5,225,473 | A |   | 7/1993 | Duan |
| 5,231,087 | A |   | 7/1993 | Thornfeldt |
| 5,234,719 | A |   | 8/1993 | Richter et al. |
| 5,260,271 | A |   | 11/1993 | Blackburn et al. |
| 5,270,188 | A |   | 12/1993 | Yamaguchi et al. |
| 5,304,540 | A |   | 4/1994 | Blackburn et al. |
| 5,314,915 | A |   | 5/1994 | Rencher |
| 5,318,955 | A |   | 6/1994 | Mueller et al. |
| 5,320,772 | A |   | 6/1994 | Tricca |
| 5,326,567 | A |   | 7/1994 | Capelli |

(Continued)

FOREIGN PATENT DOCUMENTS

| AU | 16317/95 | 11/1995 |
|---|---|---|
| AU | 2000 49587 | 12/2000 |

(Continued)

OTHER PUBLICATIONS

The Merck Manual of Diagnosis and Therapy, Seventeenth Edition, published 1999 by Merck Research Laboratories, pp. 673-677.*

(Continued)

*Primary Examiner* — Eric S Olson

(57) ABSTRACT

Methods of treating and/or preventing otitis media in a subject are provided. Methods of treating and/or preventing otitis externa are also provided.

13 Claims, 1 Drawing Sheet

U.S. PATENT DOCUMENTS

| | | | |
|---|---|---|---|
| 5,334,582 A | 8/1994 | Blackburn et al. |
| 5,346,724 A | 9/1994 | Ohgake et al. |
| 5,362,555 A | 11/1994 | Lal |
| 5,364,650 A | 11/1994 | Guthery |
| 5,378,731 A | 1/1995 | Andrews et al. |
| 5,380,756 A | 1/1995 | Andrews et al. |
| 5,389,374 A | 2/1995 | Brown-Skrobot |
| 5,408,022 A | 4/1995 | Imazato et al. |
| 5,429,819 A | 7/1995 | Oka et al. |
| 5,434,182 A | 7/1995 | Isaacs et al. |
| 5,460,802 A | 10/1995 | Asami et al. |
| 5,460,833 A | 10/1995 | Andrews et al. |
| 5,462,749 A | 10/1995 | Rencher |
| 5,466,685 A | 11/1995 | Brown-Skrobot et al. |
| 5,482,931 A | 1/1996 | Harris et al. |
| 5,490,992 A | 2/1996 | Andrews et al. |
| 5,516,510 A | 5/1996 | Beilfuss |
| 5,516,536 A | 5/1996 | Mikkelsen et al. |
| 5,547,677 A | 8/1996 | Wright |
| 5,549,901 A | 8/1996 | Wright |
| 5,550,145 A | 8/1996 | Olund et al. |
| 5,569,461 A | 10/1996 | Andrews |
| 5,629,019 A | 5/1997 | Lee et al. |
| 5,656,591 A | 8/1997 | Tomita |
| 5,660,842 A | 8/1997 | Petschow |
| 5,665,776 A | 9/1997 | Yu et al. |
| 5,705,182 A | 1/1998 | Brown-Skrobot |
| 5,708,023 A | 1/1998 | Modak et al. |
| 5,728,756 A | 3/1998 | Gaffar et al. |
| 5,736,178 A | 4/1998 | Cook et al. |
| 5,736,574 A | 4/1998 | Burnier et al. |
| 5,747,069 A | 5/1998 | Asakura et al. |
| 5,753,252 A | 5/1998 | Brown-Skrobot |
| 5,759,584 A | 6/1998 | Traupe et al. |
| 5,762,948 A | 6/1998 | Blackburn |
| 5,804,549 A | 9/1998 | Blackburn et al. |
| 5,817,325 A | 10/1998 | Sawan et al. |
| 5,862,949 A | 1/1999 | Markey et al. |
| 5,906,814 A | 5/1999 | Epstein |
| 5,945,110 A | 8/1999 | Vianen et al. |
| 5,951,993 A | 9/1999 | Scholz et al. |
| 5,955,502 A | 9/1999 | Hansen et al. |
| 5,965,088 A | 10/1999 | Lever et al. |
| 5,965,610 A | 10/1999 | Modak et al. |
| 5,968,498 A | 10/1999 | Okada et al. |
| 5,968,539 A | 10/1999 | Beerse et al. |
| 6,008,261 A | 12/1999 | Genova et al. | 516/58 |
| 6,022,551 A | 2/2000 | Jampani et al. |
| 6,033,705 A | 3/2000 | Isaacs |
| 6,045,254 A | 4/2000 | Inbar et al. |
| 6,054,139 A | 4/2000 | Lambert et al. |
| 6,054,143 A | 4/2000 | Jones |
| 6,057,274 A | 5/2000 | Bator |
| 6,071,866 A | 6/2000 | Fujiwara et al. |
| 6,089,389 A | 7/2000 | Sharon et al. |
| 6,090,075 A | 7/2000 | House |
| 6,093,417 A | 7/2000 | Petrus |
| 6,094,414 A | 7/2000 | Taira et al. |
| 6,106,851 A | 8/2000 | Beerse et al. |
| 6,110,516 A | 8/2000 | Hoover et al. |
| 6,110,908 A * | 8/2000 | Guthery | 514/188 |
| 6,113,933 A | 9/2000 | Beerse et al. |
| 6,114,319 A | 9/2000 | Kimura et al. |
| 6,121,327 A | 9/2000 | Tsuzuki et al. |
| 6,121,329 A | 9/2000 | Fujii et al. |
| 6,123,933 A | 9/2000 | Hayama et al. |
| 6,165,494 A | 12/2000 | Picciano |
| 6,171,611 B1 | 1/2001 | Picciano |
| 6,177,071 B1 | 1/2001 | Lin et al. |
| 6,183,757 B1 | 2/2001 | Beerse et al. |
| 6,183,763 B1 | 2/2001 | Beerse et al. |
| 6,187,327 B1 | 2/2001 | Stack |
| 6,187,332 B1 | 2/2001 | Gern et al. |
| 6,190,674 B1 | 2/2001 | Beerse et al. |
| 6,190,675 B1 | 2/2001 | Beerse et al. |
| 6,197,315 B1 | 3/2001 | Beerse et al. |
| 6,210,695 B1 | 4/2001 | Beerse et al. |
| 6,211,243 B1 | 4/2001 | Johnson |
| 6,214,866 B1 | 4/2001 | Drogemoller et al. |
| 6,217,877 B1 | 4/2001 | Weidner |
| 6,224,898 B1 | 5/2001 | Balogh et al. |
| 6,228,383 B1 | 5/2001 | Hansen et al. |
| 6,238,682 B1 | 5/2001 | Klofta et al. |
| 6,258,368 B1 | 7/2001 | Beerse et al. |
| 6,278,008 B1 | 8/2001 | Endo et al. |
| 6,287,577 B1 | 9/2001 | Beerse et al. |
| 6,294,186 B1 | 9/2001 | Beerse et al. |
| 6,319,895 B1 | 11/2001 | Tomita et al. |
| 6,333,045 B1 | 12/2001 | Yasueda et al. |
| 6,352,727 B1 | 3/2002 | Takahashi |
| 6,375,984 B1 | 4/2002 | Kim |
| 6,383,523 B1 | 5/2002 | Murad |
| 6,403,069 B1 | 6/2002 | Chopra |
| 6,414,023 B1 | 7/2002 | Brandsborg |
| 6,436,430 B1 | 8/2002 | Mulye |
| 6,440,405 B1 | 8/2002 | Cooper et al. |
| 6,468,521 B1 | 10/2002 | Pedersen et al. |
| 6,494,856 B1 | 12/2002 | Zygmont |
| 6,500,861 B1 | 12/2002 | Wider |
| 6,506,873 B1 | 1/2003 | Ryan et al. |
| 6,534,075 B1 | 3/2003 | Hei et al. |
| 6,548,552 B1 | 4/2003 | Deresiewicz et al. |
| 6,555,566 B2 | 4/2003 | Ponikau |
| 6,559,189 B2 | 5/2003 | Baker, Jr. et al. |
| 6,579,906 B2 | 6/2003 | Cooper et al. |
| 6,590,051 B1 | 7/2003 | Carter et al. |
| 6,596,763 B1 | 7/2003 | Thormar et al. |
| 6,635,676 B2 | 10/2003 | Baker et al. |
| 6,746,635 B2 | 6/2004 | Mathoiwitz et al. |
| 6,846,846 B2 * | 1/2005 | Modak et al. | 514/722 |
| 6,943,197 B2 | 9/2005 | Maibach et al. |
| 6,951,642 B2 | 10/2005 | Scholz et al. |
| 7,030,203 B2 | 4/2006 | Mosbey et al. |
| 7,569,530 B1 | 8/2009 | Pan |
| 7,678,389 B1 * | 3/2010 | Cordray | 424/678 |
| 7,858,662 B2 | 12/2010 | Chang |
| 2002/0013305 A1 | 1/2002 | Hanna |
| 2002/0025344 A1 | 2/2002 | Newman et al. |
| 2002/0031556 A1 | 3/2002 | Lindahl |
| 2002/0037268 A1 | 3/2002 | Stack |
| 2002/0058010 A1 | 5/2002 | Picard-Lesboueyries |
| 2002/0086039 A1 | 7/2002 | Lee et al. |
| 2002/0193417 A1 | 12/2002 | Seidel et al. |
| 2003/0147925 A1 | 8/2003 | Sawan et al. |
| 2003/0152644 A1 * | 8/2003 | Modak et al. | 424/667 |
| 2003/0194447 A1 | 10/2003 | Scholz et al. |
| 2003/0228376 A1 | 12/2003 | Mody et al. |
| 2003/0235626 A1 | 12/2003 | Maibach et al. |
| 2004/0009130 A1 * | 1/2004 | Detore et al. | 424/59 |
| 2004/0052834 A1 | 3/2004 | West |
| 2004/0091428 A1 | 5/2004 | Libin |
| 2004/0126414 A1 * | 7/2004 | Michaelis | 424/446 |
| 2004/0186183 A1 | 9/2004 | Johnson |
| 2004/0247685 A1 | 12/2004 | Modak et al. |
| 2004/0253139 A1 | 12/2004 | Denton | 422/28 |
| 2004/0265345 A1 | 12/2004 | Perricone |
| 2005/0019355 A1 | 1/2005 | Denton | 425/401 |
| 2005/0020678 A1 | 1/2005 | Denton | 514/546 |
| 2005/0053593 A1 | 3/2005 | Wang |
| 2005/0058673 A1 | 3/2005 | Scholz et al. |
| 2005/0084471 A1 | 4/2005 | Andrews et al. |
| 2005/0089539 A1 | 4/2005 | Scholz et al. |
| 2005/0112188 A1 | 5/2005 | Eliaz et al. |
| 2005/0118124 A1 | 6/2005 | Reinhart et al. |
| 2006/0029569 A1 | 2/2006 | Scholz et al. |
| 2006/0034798 A1 | 2/2006 | Mosbey et al. |
| 2006/0051384 A1 | 3/2006 | Scholz et al. |
| 2006/0051385 A1 | 3/2006 | Scholz |
| 2006/0052452 A1 | 3/2006 | Scholz |
| 2006/0099237 A1 | 5/2006 | Modak et al. |
| 2006/0205838 A1 | 9/2006 | Velamakanni |
| 2006/0275349 A1 | 12/2006 | Andrews |
| 2006/0276541 A1 | 12/2006 | Tautvydas et al. |
| 2007/0020029 A1 | 1/2007 | Baumann et al. |
| 2008/0142023 A1 | 6/2008 | Schmid |
| 2008/0287538 A1 | 11/2008 | Scholz |
| 2009/0226541 A1 | 9/2009 | Scholz |

FOREIGN PATENT DOCUMENTS

| | | |
|---|---:|---:|
| CH | 634 749 | 2/1983 |
| DE | 43 02 812 | 8/1994 |
| DE | 43 19 546 | 12/1994 |
| DE | 196 42 127 | 4/1998 |
| DE | 10156794 | 6/2003 |
| DE | 101 61 885 | 7/2003 |
| DE | 10 2004 034691 | 2/2005 |
| EP | 0 104 346 | 4/1984 |
| EP | 0 131 393 | 1/1985 |
| EP | 0 156 563 | 10/1985 |
| EP | 0 172 724 | 2/1986 |
| EP | 0 191 217 | 8/1986 |
| EP | 0 243 145 | 10/1987 |
| EP | 0 244 144 | 11/1987 |
| EP | 0 245 928 | 11/1987 |
| EP | 0 253 535 | 1/1988 |
| EP | 0 272 149 | 6/1988 |
| EP | 0 312 519 | 4/1989 |
| EP | 0 375 827 | 4/1990 |
| EP | 0 455 370 | 11/1991 |
| EP | 0 465 423 | 1/1992 |
| EP | 0 483 835 | 5/1992 |
| EP | 0 489 967 | 6/1992 |
| EP | 0 497 607 | 8/1992 |
| EP | 0 530 861 | 3/1993 |
| EP | 0 547 727 | 6/1993 |
| EP | 0 567 704 | 11/1993 |
| EP | 0 608 433 | 8/1994 |
| EP | 0 629 347 | 12/1994 |
| EP | 0 876 768 | 11/1998 |
| EP | 0 937 812 | 8/1999 |
| EP | 1449909 | 8/2004 |
| ES | 2 095 183 | 1/1997 |
| FR | 2 729 050 | 7/1996 |
| GB | 2 053 195 | 2/1981 |
| GB | 2 193 892 | 2/1988 |
| GB | 2 323 784 | 10/1989 |
| GB | 2 338 649 | 12/1999 |
| JP | 72022252 | 9/1968 |
| JP | 51-15669 | 2/1976 |
| JP | 51-139645 | 2/1976 |
| JP | 76-84022 | 9/1976 |
| JP | 51106731 | 9/1976 |
| JP | 52-07428 | 1/1977 |
| JP | 52003859 | 1/1977 |
| JP | 77-22781 | 2/1977 |
| JP | 52-33181 | 8/1977 |
| JP | 77-73621 | 9/1977 |
| JP | 53 066415 | 6/1978 |
| JP | 53-091126 | 8/1978 |
| JP | 79032058 | 10/1979 |
| JP | 56-43211 | 4/1981 |
| JP | 83018050 | 11/1981 |
| JP | 57176903 | 10/1982 |
| JP | Sho 59-163477 | 9/1984 |
| JP | 60-44539 | 3/1985 |
| JP | 85043111 | 9/1985 |
| JP | 61-152269 | 10/1986 |
| JP | 63-0166837 | 2/1987 |
| JP | 62-48612 | 3/1987 |
| JP | 63-130541 | 6/1988 |
| JP | 1-256343 | 10/1989 |
| JP | 2-46255 | 2/1990 |
| JP | 02-116302 | 5/1990 |
| JP | 3067573 | 3/1991 |
| JP | 4016173 | 1/1992 |
| JP | 4018003 | 1/1992 |
| JP | 05 229915 | 9/1993 |
| JP | 05-320067 | 12/1993 |
| JP | 6022730 | 1/1994 |
| JP | 8-151326 | 11/1994 |
| JP | 07-039356 | 2/1995 |
| JP | 8-40861 | 2/1996 |
| JP | 08-056631 | 3/1996 |
| JP | 8099878 | 4/1996 |
| JP | 8099887 | 4/1996 |
| JP | 08-175989 | 7/1996 |
| JP | 8-187070 | 7/1996 |
| JP | 8205771 | 8/1996 |
| JP | 9067593 | 3/1997 |
| JP | 9-510976 | 11/1997 |
| JP | 10109928 | 4/1998 |
| JP | 10508337 | 8/1998 |
| JP | 11113780 | 4/1999 |
| JP | Hei 11-113779 | 4/1999 |
| JP | 11302462 | 11/1999 |
| JP | 3040282 | 5/2000 |
| JP | 2000-295976 | 10/2000 |
| JP | 2001 226205 | 8/2001 |
| JP | 2001 323298 | 11/2001 |
| JP | 2002-145736 | 5/2002 |
| JP | 2001-53564 | 9/2002 |
| JP | 2002-255711 | 9/2002 |
| JP | 2002-322090 | 11/2002 |
| KR | 9105620 | 8/1991 |
| WO | WO 82/03173 | 9/1982 |
| WO | WO 89/02754 | 4/1989 |
| WO | WO 89/12399 | 12/1989 |
| WO | WO 92/21320 | 12/1992 |
| WO | WO 93/15018 | 8/1993 |
| WO | WO 93/20812 | 10/1993 |
| WO | WO 93/21906 | 11/1993 |
| WO | WO 94/18943 | 9/1994 |
| WO | WO 94/27440 | 12/1994 |
| WO | WO 95/07616 | 3/1995 |
| WO | WO 95/24179 | 9/1995 |
| WO | WO 95-26134 | 10/1995 |
| WO | WO 95/31956 | 11/1995 |
| WO | WO 96/02228 | 2/1996 |
| WO | WO 96/25469 | 8/1996 |
| WO | WO 96/29867 | 10/1996 |
| WO | WO 97/00076 | 1/1997 |
| WO | WO 97/00163 | 1/1997 |
| WO | WO 97/11912 | 4/1997 |
| WO | WO 97/16168 | 5/1997 |
| WO | WO 97/23577 | 7/1997 |
| WO | WO 97/25032 | 7/1997 |
| WO | WO 98/09520 | 3/1998 |
| WO | WO 98/14189 | 4/1998 |
| WO | 99/06064 | 2/1999 |
| WO | WO 99/11237 | 3/1999 |
| WO | WO 99/22703 | 5/1999 |
| WO | WO 99/37172 | 7/1999 |
| WO | WO 99/44444 | 9/1999 |
| WO | WO 99/59538 | 11/1999 |
| WO | WO 99/60998 | 12/1999 |
| WO | WO 99/66793 | 12/1999 |
| WO | WO 00/01351 | 1/2000 |
| WO | WO 00/03612 | 1/2000 |
| WO | WO 00/04118 | 1/2000 |
| WO | WO 00/69267 | 11/2000 |
| WO | WO 00/71183 | 11/2000 |
| WO | WO 00/71789 | 11/2000 |
| WO | WO 00/78141 | 12/2000 |
| WO | WO 01/12155 | 2/2001 |
| WO | WO 01/24839 | 4/2001 |
| WO | WO 01/28552 | 4/2001 |
| WO | 01/37806 | 5/2001 |
| WO | WO 01/43549 | 6/2001 |
| WO | WO 02/26261 | 4/2002 |
| WO | WO 02/47637 | 6/2002 |
| WO | WO 02/089849 | 11/2002 |
| WO | WO 02/100244 | 12/2002 |
| WO | WO 02/102244 A1 | 12/2002 |
| WO | WO 03/022211 | 3/2003 |
| WO | WO 03/028767 | 4/2003 |
| WO | WO 03-032948 | 4/2003 |
| WO | WO 03/037293 | 5/2003 |
| WO | WO 03/047636 | 6/2003 |
| WO | WO 2004/032927 | 4/2004 |
| WO | WO 2004-052308 | 6/2004 |
| WO | WO 2004/062643 | 7/2004 |
| WO | WO 2005-002482 | 1/2005 |
| WO | WO 2005/009353 | 3/2005 |
| WO | WO 2005/022998 | 3/2005 |
| WO | WO 2005/023233 | 3/2005 |

| | | |
|---|---|---|
| WO | WO 2005/102287 | 11/2005 |
| WO | WO 2006/026876 | 3/2006 |
| WO | WO 2006/029351 | 3/2006 |

OTHER PUBLICATIONS

Merriam-Webster's Collegiate Dictionary, published 1998 by Merriam-Webster, incorporated, p. 924.*
Gokalp et al. "Antimicrobial Screening of Mentha piperita Essential Oils, J. Agric", Food Chem. 2002, 50, 3943-3946.
Mannose may be useful for treating uterine infections [retrieved from the internet on Apr. 9, 2003], URL http://www.equinescienceupdate.co.uk/mannos.htm.
NutritionalTest.com, 10105 E Via Linda #103-192, Scottsdale, AZ 85258. Take the guess work out of taking nutrients, D. Mannose [retrieved from the internet on Apr. 9, 2003], URL <http://www.nutritionaltest.com/dmannose.html>.
Database Medline—US National Library of Medicine (NLM) Jul. 1992, Kida N. etal. "Effect of pH on preferential antibacterial-activity of ethylenediaminetetraacetic acid (EDTA)" XP002400661 Database accession No. NLM1433911.
Van Putten, P.L.; "Mandelic acid and urinary tract infections"; Antonie van Leeuwenhoek, International Journal of General and Molecular Microbiology 1979 NL; vol. 45, No. 4, 1979 pp. 622.
Rutala et al.Susceptibility of Antibiotic-Auaceptibke and Antibiotic-Resistant Hospital Bacteria to Disinfectants. Infection Control and Hospital Epidemiology Jun. 1997, vol. 18, No. 6, pp. 417-421.
ABDA: Rezepturhinweise: Triclosan in Dermatika "NRF—Neues Rezeptur Formularium" pp. 1-4 XP002391034, (Apr. 16, 2004).
Ahvenainen, "New approaches in improving the shelf life of minimally processed fruit and vegetables," Trends in Food Science & Technology, vol. 7, pp. 179-187 (Jun. 1996).
Baker et al., "Antimicrobial Properties of Lauricidin in Mechanically Deboned Chicken, Minced Fish and Chicken Sausage" J. of Food Safety, vol. 4, pp. 177-184 (1982).
Bell et al., "The Efficacy of Nisin, Sorbic Acid and Monolaurin as Perservatives in Pasteurized Cured Meat Products" Food Microbiology, vol. 4, pp. 277-283 (1987).
Block, S., "Acid-Anionic Surfactant Sanitizers", Disinfection, Sterilization and Preservation, Chapter 16, Lea & Febiger, Philidelphia PA, pp. 319-323 (1977).
Boddie, R.L., "Evaluation of postmilking teat germicides containing Lauricidin, saturated fatty acids and lactic acid", Stn Caplus, vol. 6, No. 117, XP002030991 (1992).
Branen, J.K., et al., "Enhancement of nisin, lysozyme, and monolaurin antimicrobial activities by ethylenediaminetetraacetic acid and lactoferrin", Intl Journal of Food & Microbiology, vol. 90, No. 1, pp. 63-74 XP002316393 (Jan. 1, 2004).
Chavigny, K.H., "The Use of polymixin B as a urethral lubricant to reduce the post-instrumental incidence of bacteiuria in females", Int. J. Nurs. Stud., vol. 12, pp. 33-42, (1975).
Federal Register, 21 CFR Parts 333 and 369, Tentative Final Monograph for Healthcare Antiseptic Drug Products; Proposed Rule (1994).
Flournoy, et al., "The Role of Lauricidin as an Antimicrobil Agent" Drugs of Today, vol. 21 No. 8, pp. 373-377 (1985).
Gillespie, W.A., et al., "Prevention of Catheter Infection of Urine in Female Patients", British Medical Journal, pp. 13-16 (1962).
Gloor, M., et al., "Triclosan, ein dermatologishes Lokaltherapeutikum" Hautarzt, vol. 53, pp. 724-729, XP002391035, (Nov. 2002).
Hall et al., "Spice Extracts, Lauricidin, and Propylene Glycol as Inhibitors of Clostridium botulinum in Turkey Frankfurter Slurries", Poultry Science, vol. 65, No. 6, pp. 1167-1171 (1986).
Hill, R.L. and M.W. Casewell, "The in-vitro activity of povidone-iodine cream against Staphylococus aureas and its bioavailability in nasal secretions", Journal of Hospital Infection, vol. 45, pp. 198-205 (2000).
Izat et al., "The Use of Propylene Glycol and/or Lactic Acid in Chill Water for Reducing Salmoneallae on Broilers" J. of Food Processing and Preservation, vol. 14, pp. 369-374 (1990).

Karabra, J.J., et al. "Antimicrobial Lipids: Natural and Synthetic Fatty Acids and Monoglycerides", Lipids, Champaign, IL, vol. 12, No. 9, pp. 753-759 XP000563038 (Sep. 1, 1977).
Kabara, "GRAS Antimicrobial Agents for Cosmetic Products", J. Soc. Cosmet. Chem. vol. 31, pp. 1-10 (1980).
Kabara, "Food-Grade Chemicals for Use in Designing Food Preservative Systems", J. of Food Protection, vol. 44, pp. 633-647 (1981).
Kabara, A New Preservative System for Food, J. of Food Safety, vol. 4, pp. 13-25 (1982).
Kabara, "Medium-Chain Fatty Acids and Esters as Antimicrobial Agents" Cosmetic and Drug Preservation, vol. 16, pp. 275-304 (1984).
Kato et al., "Combined Effect on Different Drugs on the Antibacterial Activity of Fatty Acids and their Esters", vol. 4, pp. 355-363 (1975).
Kato, et al., "Combined Effect of Citric and Polyphosphoric Acid on the Antibacterial Activity of Monoglycerides", vol. 4, No. 6 pp. 254-261 (1976).
Kiser, K. et al., "Development and Characterization of Staphylococcus aureus Nasal Colonization Model in Mice," Infect and Immunity, vol. 67, No. 10, pp. 5001-5006 (1999).
Kostiala, A.A.I., et al., "Effect of nitrofurantoin and methenamine hippurate prophylaxis on bacteria and yeasts in the urine of patients with an indwelling catheter", J. of Hospital Infection, vol. 3, pp. 347-364 (1982).
MacFarlane, D.E., "Prevention and treatment of catheter-associated urinary tract invections", J. of Infection, vol. 10, pp. 96-106 (1985).
May, et al., "Time-kill studies of tea tree oils on clinical isolates",J. of Antimicrobial Chemotherapy, vol. 45, pp. 639-643 (2000).
Mead et al., "Food-Related Illness and Death in the United States", Emerg. Infect. Dis., vol. 5, No. 5, pp. 607-625 (1999).
Merianos, "Chapter 13, Quaternary Ammonium Antimicrobial Compounds," in Disinfection, Sterilization, and Preservation, 4th Ed., Block, Ed., Philadelphia, PA, Title page, Publication page, and Chapter 13 (pp. 225-255), (1991).
Morgan, D. M., "Urinary tract infection in hospitalized patients", Canadian Hospital, pp. 27-30 (1973).
Nakagaki, et al., "Solubility & Hydrolysis Rate of I-Monolaurin in Aqueous Solutions", Yakugaku Zasshi, vol. 90, No. 10, pp. 1310-1315 (1970).
Nicoletti, G. et al., The Antimicrobial Activity in vitro of chlorhexidine, a mixture of isothiazolinones (Kathon CG) and cetyl trimethyl ammonium bromide (CTAB), Journal of Hospital Infection, vol. 23, pp. 87-111 (1993).
Oh, et al., "Enhanced Inhibition of Listeria monocytogenes by Glycerol Monolaurate with Organic Acids", Journal of Food Science, vol. 59, No. 6, pp. 1258-1261 (1994).
Perez-Roth, E. et al. "Mupirocin resistance in methicillin-resistant Staphylococcus aureus clinical isolates in a Spanish hospital. Co-application of multiplex PCR assay and conventional microbiology methods", Diag. Micro. Infect. Dis., vol. 43, pp. 123-128 (2002).
Perl, T. et al., "New Approaches to Reduce Staphylococcus aureua Nosocomial Infection Rates: Treating S. aureus Nasal Carriage", Ann. Pharmacother., vol. 32, pp. S7-S16 (1998).
Physician's Desk Reference, definition of the composition of Aquaphor, p. 685, Edition (1993).
Product Information Brochure, Sensive SC 50 a multifunctional additive, Schuelke & Mayer (16 pgs.) (Nov. 2006).
Projan, et al., "Glycerol Monolaurate Inhibits the Production of β-Lactamase, Toxic Shock Syndrom Toxin-1, and Other Staphylococal Exoproteins by Interfering with Signal Transduction" Journal of Bacteriology, vol. 176, No. 14, pp. 4204-4209 (Jul. 1994).
Remington's Pharmaceutical Services, definition of absorption base, 14th Ed., p. 1600 (1970).
Rice, J. "Organic acid sprays," Food Processing, pp. 45, 47-48, 50 (Apr. 1994).
Sawhney, A.S. et al., "Bioerodible Hydrogels Based on Photopolymerized Poly(ethylene glycol)-co-poly(a-hydroxy acid) Diacrylate Macromers", Macromolecules, vol. 26, pp. 581-587 (1993).
Schemmel et al., "Monolaurin As an Anticaries Agent", Chapter 4, Symposium on the Pharmacological Effect of Lipds, pp. 37-43 (1983).

Sciarra and Cutie, "Aersols," *Chapter 92 in Remington's Pharmaceutical Sciences*, 18th edition, pp. 1694-1712 (1990).

Silverman, Chapter 44 in *Disinfection, Sterilization, and Preservation*, First addition, C. A. Lawrence and S.S. Block (1968).

Stecker, Ph.D., "Chapter 14, The Salicylanilides and Carbanilides," in Disinfection, Sterilization, and Preservation, 2nd Ed., Block, Ed., Philadelphia, PA, Title page, Publication page, and Chapter 14 (pp. 282-300) (1977).

United States Pharmacopeia Official Monographs for Povidone-Iodine, Assay for Available Iodine (pp. 1600-1602).

Vadehra et al., "Comparison of Antibacterial Properties of Lauricidin® and BHA against Antibotic Resistant and Sensitive Strains of *Staphylococcus aureus* and *Pseudomonos aeruginosa*" *AOCS Monograph* vol. 13, No. 2, pp. 77-87, XP000560207 (1985).

Venkitanarayanan et al., "Inactivation of *Escherichia coli* 0157:H7 by combinations of GRAS chemicals and temperature", *Food Microbiology*, vol. 16, pp. 75-82 (1999).

Vorum, H. et al., "Solubility of Long-Chain Fatty Acids in Phosphate Buffer at pH 7.4," *Biochimica et. Biophysica Acta*, vol. 1126, pp. 135-142 (1992).

Wakabayashi, et al., Increased *Staphylococcus*-killing Activity of an Antimicrobial Peptide, Lactoferricin B, with Minocycline and Monoacylglyserol, *Bioscience Biotechnology and Biochemistry* vol. 66, No. 10, pp. 2161-2167 (Oct. 2002).

Wang et al., "Inhibition of *Listeria monocytogenes* by Monoacylglycerols Synthesized from Coconut Oil and Milkfat by Lipase-Catalzed Glycerolysis" *J. of Agric. Food Chem.*, vol. 41, pp. 1000-1005 (1993).

Watanabe, H. et al., "Low Concentrations of Mupirocin in the Pharynx following Intranasal Application May Conrtibute to Mupirocin Resistance in Methicillin-Resistant *Staphylococcus aureus*," *J. Clin. Micro.*, vol. 39, No. 10 pp. 3775-3777 (2001).

Whitley, et al., "Herpes zoster: focus on treatment in older adults", *Antiviral Research* vol. 44, pp. 145-154 (1999).

Williams, J.D., et al., "Trials of Five Antibacterial Creams in the Control of Nasal Carriage of *Staphylococcus aureus*", *The Lancet*, vol. 290, Issue 7512, pp. 390-392 (Aug. 1967).

Williamson et al., "A New Method for the Quantitative Investigation of Cutaneous Bacteria," J. Invest. Derm., vol. 45, pp. 498-503 (1965).

Wooley, "EDTA-tris Potentiation of Antimicrobial Agents", *Modern Veterinary Practice*, pp. 113-116 (1983).

http://www.lungusa.org/site/pp.asp?c=dvLUK9O0E&b=35873, published Aug. 22, 2007.

http://www.merck.com/mmhe/sec06/ch089/ch089d.html, (2003).

Mosges R., Hassan H.. The role of the respiratory mucosa in the infectous process. *Respiratory mucosa: the core of infection and inflammation*, Title page, Editorial page, pp. 1-32, Product information page, and Publication page (36 pgs. Total) 1998 (Servier, Paris).

Berkow, The Merck Manual of Diagnosis and Therapy, 16th Edition, May 1, 1995, vol. 3, pp. 2228-2231.

Clemons, "Evaluation of a Subcutaneously Implanted Chamber for Antibody Production in Rabbits", Laboratory Animal Science, Jun. 1992, vol. 42, No. 3, pp. 307-311.

Elliott, "Bladder Irrigation or Irritation?",British Journal of Urology, Oct. 1989, vol. 64, pp. 391-394.

Medical Digest, May 1991, vol. 40, No. 3, pp. 2-6.

Morizono, Safety of Antimicrobials Applied in the Middle Ear Cavity, Aurinasal Clinic, Practica. Oto.rhino.laryngologica. Suppl., 2002, vol. 95, No. 7, pp. 663-669.

Osborne, "Skin Penetration Enhancers, in Technical literature", Pharmaceutical Technology, Nov. 1997, pp. 58-66.

Physicians' Desk Reference, To Pharmaceutical Specialties and Biologicals, 26th Edition, 628 (1972).

Schlievert, "Effect of glycerol monolaurate on bacterial growth and toxin production",Antimicrobial Agents Chemotherapy, Mar. 1992, vol. 36, No. 3, pp. 626-631.

Schneeberger, "A randomized study on the effect of bladder irrigation with povidone-iodine before removal of an indwelling catheter", Journal of Hospital Infection, Jul. 1992, vol. 21, No. 3, pp. 223-229.

Tanaka, "Antibacterial Compounds From Nutmeg Against Upper Airway Respiratory Tract Bacteris", ITE Letters on Batteries, New Technologies and Medicine, 2000, vol. 1, No. 3, pp. 412-417.

Stillman et al., "Relative irritancy of free fatty acids of different chain length," *Contact Dermatitis*, 1975;1:65-69.

Wright and Roland, "Chapter 11: Middle Ear Effects of Ototopical Agents," *Ototoxicity*, Hamilton, Ontario, Canada; 2004: 107-113.

* cited by examiner

METHODS OF TREATING EAR INFECTIONS

CROSS REFERENCE TO RELATED APPLICATIONS

This application is a national stage filing under 35 U.S.C. 371 of PCT/US2006/008953, filed Mar. 20, 2006, which claims priority to U.S. Provisional Application No. 60/660,593, filed Mar. 10, 2005, the disclosure of which is incorporated by reference in its/their entirety herein.

RELATED APPLICATIONS

The present application claims priority to U.S. Provisional Patent Application Ser. No. 60/660,593, filed on Mar. 10, 2005, which is incorporated herein by reference.

BACKGROUND

Most ear infections are characterized by inflammation. In general, this condition, referred to as "otitis," is treated upon diagnosis to reduce the risk of such conditions as hearing loss, tinnitus, facial nerve palsy, mastoiditis, labyrinthitis, vertigo, and encephalitis. The majority of ear infections affect either the external or the middle ear.

Otitis externa (infection of the external ear) is primarily caused by bacterial infections (caused, for example, by *Staphylococcus intermedius, Streptococcus* spp., *Pseudomonas* spp., *Proteus* spp., and *Escherichia coli*). Normally, the external auditory canal is inhabited by a low concentration of bacteria, whose growth is largely inhibited by the slightly acidic pH and the build-up of cerumen (ear wax). Patients who scrape away the cerumen and epithelium leave an open wound characterized by a high pH, in turn establishing an environment favorable for bacterial infection. Furthermore, in patients whose ears are often submersed in water (due to swimming or sweating, for example), the skin swells and loses its natural acidic protection, therefore increasing the susceptibility of such patients to otitis externa. If untreated, infection of the external auditory canal may lead to inflammation of the middle and inner ear and may even spread to the pinna, periauricular soft tissues, or the temporal bone. Otitis externa often results in a large build up of cerumen that may actually plug the ear canal and result in temporary hearing loss and pain. Otitis externa is also a problem in domestic pets, and particularly in dogs with ear canals that are covered with the ear such as Cocker Spaniels.

Otitis media, a common ailment in children, is a painful condition characterized by inflammation of the middle ear and resulting from a bacterial (e.g., *Streptococcus pneumoniae, Haemophilis influenza,* or *Moraxella catarhalis*) or viral infection. More than two-thirds of children in the United States have had at least one episode of otitis media by the age of three. It has been reported that treatment of otitis media costs the United States healthcare system more than 5 billion dollars annually. Treatment of otitis media is critical, since otitis media is associated with significant childhood morbidity and is a primary cause of hearing loss in children. During episodes of otitis media, fluid accumulates in the middle ear or, as it is also known, the tympanic cavity.

Acute otitis media is a condition in which fluid accumulation in the middle ear is accompanied by signs or symptoms of ear infection (including both viral and bacterial etiologies). Such pathology may exhibit a bulging eardrum accompanied by pain or, in some instances, perforation of the tympanic membrane. Such perforations may also be accompanied by drainage of purulent material. In contrast, otitis media with effusion is typified by fluid accumulation within the tympanic cavity without signs of infection.

Both acute otitis media and otitis media with effusion may cause substantial pain as pressure increases, positively or negatively, within the confines of the tympanic chamber. Oral antibiotics, steroids, and antibiotic/steroid combinations have been utilized to treat otitis media. Antihistamine/decongestants have also been utilized in the treatment of otitis media with effusion.

The anatomical features of the middle ear define what can be described as a "sealed" chamber although pressure equalization is accomplished through the Eustachian tube. On its lateral border, the middle ear is effectively isolated from the external auditory meatus (in the absence of a punctured ear drum), by the tympanic membrane. Medially, the middle ear is effectively sealed from the inner ear by a bony wall and the round window. The posterior wall of the tympanic cavity communicates with a large, but effectively sealed mastoid antrum. Only the anterior wall of the middle ear contains a passageway for effective communication outside of the tympanic cavity. There, a natural pathway provided by the auditory or, as it is also known, the eustachian tube, provides communication with the nasopharynx.

During episodes of acute otitis media, the painful increase in middle ear pressure may naturally resolve through a resultant perforation of, and drainage through, the tympanic membrane. However, the increased fluid pressure associated with otitis media with effusion (OME) does not resolve via this mechanism. In fact, for those patients suffering otitis media for prolonged periods of time, and especially for those with significant associated hearing loss, myringotomy with the placement of a tympanostomy tube may be indicated as a means of equalizing middle ear pressure and in restoring normal hearing. Recently, laser surgery has also been utilized to provide an aperture through the tympanic membrane through which the fluid trapped within the middle ear may drain. Usually these artificial perforations of the tympanic membrane heal once the infection is resolved; however, in a significant number of patients the perforation does not heal resulting in hearing loss and increased susceptibility to middle ear infections. As used herein, a "middle ear infection" is a bacterial or viral infection of the middle ear or Eustachian tube. This term is used interchangeably with the clinical term "otitis media."

Besides the perforations of the eardrum provided by infection (acute otitis media), myringotomy and laser surgery, the eustachian tube (the natural middle ear drainage path described above) provides potential drainage of fluid from the middle ear. Unfortunately, episodes of otitis media with effusion (OME) effectively eliminate this drainage path of relieving middle ear pressurization. Reduced patency of the eustachian tube is believed to be one of the primary causes of OME in pediatric patients. In fact, it is known that OME elevates eustachian tube opening pressure independent of other pathological conditions effecting this conduit. Several references have suggested that improving the patency of the Eustachian tube may aide in resolving otitis media.

Thus, there is still a need for additional antimicrobial compositions.

SUMMARY

The present invention provides methods of preventing or treating ear infections (particularly, otitis media) by the local delivery of an antimicrobial composition. Use of this therapy can provide a higher concentration of antimicrobial delivered to the site of infection. This typically results in little or no systemic effects. That is, typically topical delivery allows alteration of the local microenvironment without the adverse effects of eliminating microbial flora in other parts of the body (e.g., the vagina) and/or induction of antibiotic resistance. The antimicrobial compositions used in the methods of the present invention include one or more antiseptics that have little or no chance of antimicrobial resistance formation and are rapid acting with broad spectrum antimicrobial activity. Ototopical medications also provide cost-effective treatment over comparable systemic medications.

The composition may be delivered to the middle ear by injection through the tympanic membrane or transfer through a ruptured tympanic membrane (TM) but is preferably delivered through an intact TM by diffusion across the TM and/or TM surrounding tissue or by delivery via the Eustachian tube.

In one embodiment, a method of treating and/or preventing otitis media in a subject is provided. The method includes contacting the middle ear, tympanic membrane, tympanic membrante surrounding tissue, and/or Eustachian tube with an antimicrobial composition comprising an effective amount of an antimicrobial component comprising a (C7-C14)saturated fatty ether of a polyhydric alcohol, a (C8-C22)unsaturated fatty ether of a polyhydric alcohol, a (C7-C14)fatty alcohol ester of a (C2-C8)hydroxycarboxylic acid, a (C8-C22)mono- or poly-unsaturated fatty alcohol ester of a (C2-C8) hydroxycarboxylic acid, an alkoxylated derivative of any of the foregoing having a free hydroxyl group, and combinations thereof; wherein the alkoxylated derivative has less than 5 moles of alkoxide per mole of polyhydric alcohol or hydroxycarboxylic acid; with the proviso that for polyhydric alcohols other than sucrose, the esters comprise monoesters and the ethers comprise monoethers, and for sucrose the esters comprise monoesters, diesters, or combinations thereof, and the ethers comprise monoethers; and an effective amount of a penetration agent, wherein the penetration agent promotes the diffusion of the antimicrobial component into the middle ear.

In one embodiment, a method of treating and/or preventing otitis media in a subject is provided. The method includes contacting the middle ear, tympanic membrane, tympanic membrane surrounding tissue, and/or Eustachian tube with an antimicrobial composition, the composition comprising an effective amount of an antimicrobial component comprising a (C7-C14)saturated fatty ether of a polyhydric alcohol, a (C8-C22)unsaturated fatty ether of a polyhydric alcohol, a (C7-C14)fatty alcohol ester of a (C2-C8)hydroxycarboxylic acid, a (C8-C22)mono- or poly-unsaturated fatty alcohol ester of a (C2-C8)hydroxycarboxylic acid, an alkoxylated derivative of any of the foregoing having a free hydroxyl group, and combinations thereof; wherein the alkoxylated derivative has less than 5 moles of alkoxide per mole of polyhydric alcohol or hydroxycarboxylic acid; with the proviso that for polyhydric alcohols other than sucrose, the esters comprise monoesters and the ethers comprise monoethers, and for sucrose the esters comprise monoesters, diesters, or combinations thereof, and the ethers comprise monoethers; wherein the viscosity of the composition is less than 20 cps at 23° C.

In one embodiment, a method of treating and/or preventing otitis media in a subject is provided. The method includes contacting the middle ear, tympanic membrane, tympanic membrane surrounding tissue, and/or Eustachian tube with an antimicrobial composition comprising an effective amount of an antimicrobial component comprising a (C6-C14)alkyl carboxylic acid, a (C8-C22)mono- or poly-unsaturated carboxylic acid, a fatty acid ester formed from one of the foregoing fatty acids with a hydroxyl carboxylic acid, and combinations thereof; and an effective amount of a penetration agent, wherein the penetration agent promotes the diffusion of the antimicrobial component into the middle ear.

In one embodiment, a method of treating and/or preventing otitis media and/or otitis externa in a subject is provided. The method includes contacting the middle ear, tympanic membrane, tympanic membrane surrounding tissue, and/or Eustachian tube with an antimicrobial composition, the composition comprising an effective amount of an antimicrobial component comprising an antiseptic selected from the group consisting of an antimicrobial lipid and a phenolic antiseptic, or combinations thereof a (C6-C14)alkyl carboxylic acid, a (C8-C22)mono- or poly-unsaturated carboxylic acid, a fatty acid ester formed from one of the foregoing fatty acids with a hydroxyl carboxylic acid, and combinations thereof; wherein the viscosity of the composition is less than 20 cps at 23° C.

In one embodiment, a method of treating and/or preventing otitis media in a subject is provided. The method includes contacting the middle ear, tympanic membrane, tympanic membrane surrounding tissue, and/or Eustachian tube with an antimicrobial composition comprising an effective amount of an antimicrobial component comprising (C7-C14)saturated fatty acid ester of a polyhydric alcohol, a (C8-C22) unsaturated fatty acid ester of a polyhydric alcohol; an alkoxylated derivative of any of the foregoing having a free hydroxyl group, and combinations thereof; wherein the alkoxylated derivative has less than 5 moles of alkoxide per mole of polyhydric alcohol; with the proviso that for polyhydric alcohols other than sucrose, the esters comprise monoesters and the ethers comprise monoethers, and for sucrose the esters comprise monoesters, diesters, or combinations thereof, and the ethers comprise monoethers; and an effective amount of a penetration agent, wherein the penetration agent promotes the diffusion of the antimicrobial component into the middle ear; wherein the fatty acid esters or alkoxylate derivatives thereof comprise less than 15 wt-% di- or tri-esters based on the total weight of the antimicrobial lipid component; and wherein the viscosity of the composition is less than 20 cps at 23° C.

In one embodiment, a method of treating and/or preventing otitis media and/or otitis externa in a subject is provided. The method includes contacting the middle ear, tympanic membrane, tympanic membrane surrounding tissue, and/or Eustachian tube with an antimicrobial composition, the composition comprising greater than 2 wt-% and less than 6 wt-% of an antimicrobial component comprising (C7-C14)saturated fatty acid ester of a polyhydric alcohol, a (C8-C22)unsaturated fatty acid ester of a polyhydric alcohol; an alkoxylated derivative of any of the foregoing having a free hydroxyl group, and combinations thereof; wherein the alkoxylated derivative has less than 5 moles of alkoxide per mole of polyhydric alcohol; with the proviso that for polyhydric alcohols other than sucrose, the esters comprise monoesters and the ethers comprise monoethers, and for sucrose the esters comprise monoesters, diesters, or combinations thereof, and the ethers comprise monoethers; wherein the viscosity of the composition is less than 20 cps at 23° C.

In one embodiment, a method of treating and/or preventing otitis media in a subject is provided. The method includes contacting the middle ear, tympanic membrane, tympanic membrane surrounding tissue, and/or Eustachian tube with an antimicrobial composition comprising an effective amount of an antimicrobial component comprising a (C7-C14)saturated fatty acid ester of a polyhydric alcohol, a (C8-C22) unsaturated fatty acid ester of a polyhydric alcohol; an alkoxylated derivative of any of the foregoing having a free hydroxyl group, and combinations thereof; wherein the alkoxylated derivative has less than 5 moles of alkoxide per mole of polyhydric alcohol; with the proviso that for polyhydric alcohols other than sucrose, the esters comprise monoesters and the ethers comprise monoethers, and for sucrose the esters comprise monoesters, diesters, or combinations thereof, and the ethers comprise monoethers; and an effective amount of a penetration agent, wherein the penetration agent promotes the diffusion of the antimicrobial component into the middle ear; wherein the antimicrobial composition is free of antibiotics.

In one embodiment, a method of treating and/or preventing otitis media in a subject is provided. The method includes contacting the middle ear, tympanic membrane, tympanic membrane surrounding tissue, and/or Eustachian tube with an antimicrobial composition comprising an effective amount of an antimicrobial component comprising a phenolic antiseptic, a cationic antiseptic, and combinations thereof; and an effective amount of a penetration agent, wherein the penetration agent promotes the diffusion of the antimicrobial component into the middle ear.

In one embodiment, a method of treating and/or preventing otitis media in a subject is provided. The method includes contacting the middle ear, tympanic membrane, tympanic membrante the surrounding tissue, and/or Eustachian tube with an antimicrobial composition comprising an effective amount of an antimicrobial component comprising a phenolic antiseptic, a cationic antiseptic, and combinations thereof; wherein the viscosity of the composition is less than 20 cps.

In one embodiment, a method of treating and/or preventing otitis media in a subject is provided. The method includes contacting the middle ear, tympanic membrane, tympanic membrane surrounding tissue, and/or Eustachian tube with an antimicrobial composition, the composition comprising an effective amount of an antimicrobial component comprising a (C7-C14)saturated fatty ether of a polyhydric alcohol, a (C8-C22)unsaturated fatty ether of a polyhydric alcohol, a (C7-C14)fatty alcohol ester of a (C2-C8)hydroxycarboxylic acid, a (C8-C22)mono- or poly-unsaturated fatty alcohol ester of a (C2-C8)hydroxycarboxylic acid, an alkoxylated derivative of any of the foregoing having a free hydroxyl group, and combinations thereof; wherein the alkoxylated derivative has less than 5 moles of alkoxide per mole of polyhydric alcohol or hydroxycarboxylic acid; with the proviso that for polyhydric alcohols other than sucrose, the esters comprise monoesters and the ethers comprise monoethers, and for sucrose the esters comprise monoesters, diesters, or combinations thereof, and the ethers comprise monoethers.

In one embodiment, a method of treating and/or preventing otitis media in a subject is provided. The method includes contacting the middle ear, tympanic membrane, tympanic membrane surrounding tissue, and/or Eustachian tube with an antimicrobial composition, the composition comprising an effective amount of an antimicrobial component comprising a (C6-C14)alkyl carboxylic acid, a (C8-C22)mono- or poly-unsaturated carboxylic acid, a fatty acid ester formed from one of the foregoing fatty acids with a hydroxyl carboxylic acid, and combinations thereof.

In one embodiment, the present invention provides a method of treating or preventing otitis media by introduction of an antimicrobial composition into the middle ear wherein the an antimicrobial composition that includes an antimicrobial lipid component and is substantially free of antigenic components and antibiotics.

DEFINITIONS

The following terms are used herein according to the following definitions.

"Effective amount" means the amount of the antimicrobial component and/or the enhancer component when in a composition, as a whole, provides an antimicrobial (including, for example, antiviral, antibacterial, or antifungal) activity that reduces, prevents, or eliminates one or more species of microbes such that an acceptable level of the microbe results. Typically, this is at least a 0.5 log reduction using the Antimicrobial Kill Rate Test described herein, and is desirably at least a 1 log reduction, more preferably at least a 2 log reduction, and most desirably reduces the bacteria to a non-detectable level. It should be understood that in the compositions described herein, the concentrations or amounts of the components, when considered separately, may not kill to an acceptable level, or may not kill as broad a spectrum of undesired microorganisms, or may not kill as fast; however, when used together such components provide an enhanced (preferably synergistic) antimicrobial activity (as compared to the same components used alone under the same conditions).

It should be understood that (unless otherwise specified) the listed concentrations of all components are for "ready to use" or "as used" compositions. The compositions can be in a concentrated form. That is, certain embodiments of the compositions can be in the form of concentrates that would be diluted by the user with an appropriate vehicle; however, this is typically not convenient for the present application.

"Hydrophilic" refers to a material that will dissolve or disperse in water (or other aqueous solution as specified) at a temperature of 23° C. in an amount of at least 7% by weight, preferably at least 10% by weight, more preferably at least 20% by weight, even more preferably at least 25% by weight, even more preferably at least 30% by weight, and most preferably at least 40% by weight, based on the total weight of the hydrophilic material and the water. The component is considered dissolved if after thoroughly mixing the compound with water at 60° C. for at least 4 hours and allowing this to cool to 23-25° C. for 24 hours, and then again mixing the composition thoroughly it appears as a uniform clear solution without visible cloudiness, phase separation, or precipitate in a jar having a path length of 4 cm. Typically, when placed in 1×1 cm cell, the sample containing a hydrophilic material exhibits greater than, or equal to, 70% transmission measured in a suitable spectrophotometer at a wavelength of 655 nm. This dissolution test is done at the concentration of interest, e.g., at 7-40% by weight. Water dispersible hydrophilic materials disperse in water to form uniform cloudy dispersions after vigorous shaking of a 5% by weight mixture of the hydrophilic component in water above the melting point of the component followed by cooling to room temperature for 4 hours, or preferably placing in a Warning Blender half full for 3 minutes and allowing any foam to settle to form a uniform dispersion without visible phase separation (creaming or settling) after standing for 60 minutes. Preferred hydrophilic components are water-soluble. The hydrophilic component can be water.

"Hydrophobic" or "water-insoluble" refers to a material that will not significantly dissolve in water at 23° C. This means that less than 5% by weight, preferably less than 1% by weight, more preferably less than 0.5% by weight, and even more preferably less than 0.1% by weight, based on the total weight of the hydrophobic material and the water, will dissolve. Solubility can be determined by thoroughly mixing the compound with water at the appropriate concentration at 23° C. for at least 24 hours (or at elevated temperature if that is necessary to dissolve the compound), allowing this to sit at 23-25° C. for 24 hours, and observing the sample. In a glass jar with a 4-cm path length the sample should have evidence of a second phase, which can be liquid or solid and may be separated on the top, bottom, or distributed throughout the sample. For crystalline compounds care should be taken to avoid producing a supersaturated solution. The components should be mixed and observed. Cloudiness or presence of a visible precipitate or separate phase indicates that the solubility limit has been exceeded. Typically, when placed in 1×1 cm cell the sample composition containing the hydrophobic compound in water has less than 70% transmission measured in a suitable spectrophotometer at a wavelength of 655 nm. For solubility determinations less than that which can be observed with the naked eye the solubility is determined using radiolabeled compounds as described under "Conventional Solubility Estimations in Solubility of Long-Chain Fatty Acids in Phosphate Buffer at pH 7.4," Henrik Vorum, et al. in *Biochimica et. Biophysica Acta,* 1126, 135-142 (1992).

"Stable" means physically stable or chemically stable, which are both defined in greater detail below.

"Enhancer" means a component that enhances the effectiveness of the antimicrobial component such that when the composition less the antimicrobial component and the composition less the enhancer component are used separately, they do not provide the same level of antimicrobial activity as the composition as a whole. For example, an enhancer component in the absence of the antimicrobial component may not provide any appreciable antimicrobial activity. The enhancing effect can be with respect to the level of kill, the speed of kill, and/or the spectrum of microorganisms killed, and may not be seen for all microorganisms. In fact, an enhanced level of kill is most often seen in Gram negative bacteria such as *Escherichia coli.* An enhancer may be a synergist such that when combined with the remainder of the composition, the composition as a whole displays an activity that is greater than the sum of the activity of the composition less the enhancer component and the composition less the antimicrobial component.

"Microorganism" or "microbe" or "microorganism" refers to bacteria, yeast, mold, fungi, protozoa, mycoplasma, as well as viruses (including lipid enveloped RNA and DNA viruses).

"Antibiotic" means an organic chemical produced by microorganisms that has the ability in dilute concentrations to destroy or inhibit microorganisms and is used to treat infectious disease. This may also encompass semi-synthetic compounds that are chemical derivatives of the compound produced by microorganisms or synthetic compounds that act on very specific biochemical pathways necessary for the cell's survival.

"Antiseptic" means a chemical agent that kills pathogenic and non-pathogenic microorganisms. Preferred antiseptics exhibit at least a 4 log reduction of both *P. aeruginosa* and *S. aureus* in 60 minutes and in some instances 10 minutes, from an initial inoculum of $1-3 \times 10^7$ CFU/mL when tested in Mueller Hinton broth at 35° C. at a concentration of 0.25 wt-% in a Rate of Kill assay using an appropriate neutralizer as described in "The Antimicrobial Activity in vitro of chlorhexidine, a mixture of isothiazolinones (Kathon CG) and cetyl trimethyl ammonium bromide (CTAB)," G. Nicoletti et al., *Journal of Hospital Infection,* 23, 87-111 (1993). Antiseptics generally interfere more broadly with the cellular metabolism and/or the cell envelope. Antiseptics are sometimes referred to as disinfectants, especially when used to treat hard surfaces.

"Mucous membranes," "mucosal membranes," and "mucosal tissue" are used interchangeably and refer to the surfaces of the nasal (including anterior nares, nasoparangyl cavity, etc.), oral (e.g., mouth), middle ear, and other similar tissues.

"Antimicrobial lipid" means an antimicrobial compound having at least one alkyl or alkylene group having at least 6 carbon atoms, more preferably, 7 carbon atoms, and more preferably 8 carbon atoms, and preferably having a solubility in water of no greater than 1.0 gram per 100 grams (1.0 g/100 g) deionized water. Preferred antimicrobial lipids have a solubility in water of no greater than 0.5 g/100 g deionized water, more preferably, no greater than 0.25 g/100 g deionized water, and even more preferably, no greater than 0.10 g/100 g deionized water. Solubilities are determined using radiolabeled compounds as described under "Conventional Solubility Estimations" in Solubility of Long-Chain Fatty Acids in Phosphate Buffer at pH 7.4, Henrik Vorum et al., in *Biochimica et. Biophysica Acta.,* 1126, 135-142 (1992). Preferred antimicrobial lipids have a solubility in deionized water of at least 100 micrograms (µg) per 100 grams deionized water, more preferably, at least 500 µg/100 g deionized water, and even more preferably, at least 1000 µg/100 g deionized water. The antimicrobial lipids preferably have a hydrophile/lipophile balance (HLB) of at most 6.2, more preferably at most 5.8, and even more preferably at most 5.5. The antimicrobial lipids preferably have an HLB of at least 3, preferably at least 3.2, and even more preferably at least 3.4.

"Fatty" as used herein refers to a straight or branched chain alkyl or alkylene moiety having at least 6 (odd or even number) carbon atoms, unless otherwise specified.

"Affliction" means a condition to a body resulting from sickness, disease, injury, bacterial colonization, etc.

"Treat" or "treatment" means to improve the condition of a subject relative to the affliction, typically in terms of clinical symptoms of the condition.

"Decolonization" refers to a reduction in the number of microorganisms (e.g., bacteria, virus, and fungi) present in or on tissue that do not necessarily cause immediate clinical symptoms. Examples of decolonization include, but are not limited to, decolonization of the outer ear, middle ear, and Eustachian tube. Ordinarily, fewer microorganisms are present in colonized tissue than in infected tissue. When the tissue is completely decolonized the microorganisms have been "eradicated" and are non-detectable.

An "instrument" means any medical article intended to perform a task on a subject, and most often includes tubes such as myringotomy tubes, surgical instruments, fluid sampling devices, and the like.

"Subject" and "patient" includes humans, sheep, horses, cattle, pigs, dogs, cats, rats, mice, or other mammal.

"Otitis media" as used herein includes, without limitation, otitis media, acute otitis media, and otitis media with effusion.

"Otitis inflammation" and "ear infections" as used herein includes, without limitation, otitis media and otitis externa.

"Middle ear" means the main cavity of the ear; between the ear drum and the inner ear.

"External ear" means the part of the ear visible externally.

"Tympanic membrane" is also referred to as the ear drum.

The tympanic membrane "surrounding tissue" refers to the parts of the external auditory canal immediately adjacent to the tympanic membrane (ear drum) where a composition of the present invention could diffuse through this tissue into the middle ear.

"Diffuse" or "diffusion" as used herein refers to movement of a compound(s) or composition through an otherwise intact tissue such as the tympanic membrane, tissue surrounding the tympanic membrane, and the like.

The terms "comprises" and variations thereof do not have a limiting meaning where these terms appear in the description and claims.

As used herein, "a," "an," "the," "at least one," and "one or more" are used interchangeably. The term "and/or" means one or all of the listed elements (e.g., preventing and/or treating an infection means preventing, treating, or both treating and preventing further infections).

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF DRAWINGS

FIG. 1 (a-d) are GC Chromatograms of material recovered from the right middle ear of a Chinchilla and comparison Chromatograms of components used to treat the ear.

DETAILED DESCRIPTION OF ILLUSTRATIVE EMBODIMENTS

Figure 1A:
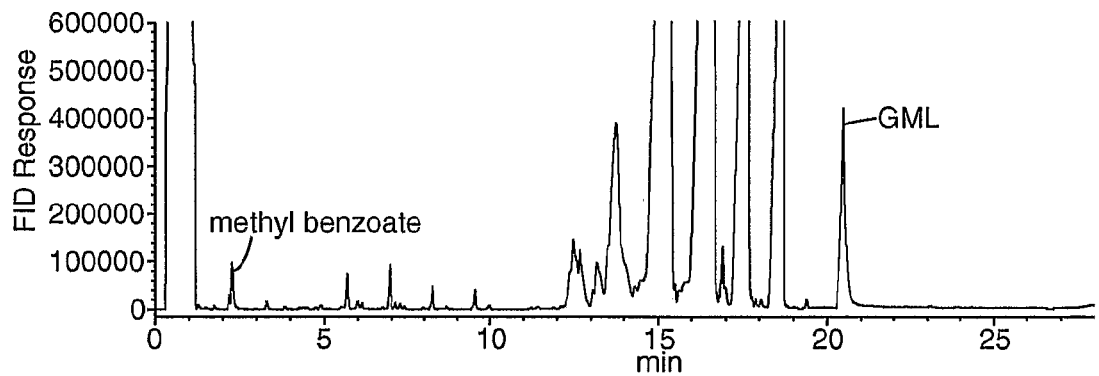
FIG. 1(a) is the GC chromatogram of material recovered from the Chinchilla's middle ear.

The antimicrobial compositions of the present invention provide a local treatment for otitis media with an antimicrobial composition that will effectively and rapidly alleviate the condition, not easily generate microbial resistance, with very low chance of allergic reaction. The antimicrobial composition is both antibacterial and antiviral, and additionally improves the patency of the Eustachian tube. The antimicrobial composition may also comprise active pharmaceutical ingredients to alleviate pain. Many of the compositions of the present invention may also be useful for treating otitis externa.

It should be noted that the use of antimicrobial compositions (e.g., antibiotics, antiseptics) plays an important part in current medical therapy. Treatment of otitis media by means of administration of anti-inflammatory agents, antibiotics, decongestants and/or antihistamines, or combinations thereof, is limited in effectiveness as, in the absence of perforation, there is presently no method for direct application of such drugs directly to target tissues of the eustachian tube and/or middle ear. Systemic applications of drugs via parenteral or oral routes, while eventually reaching the eustachian tube and middle ear, may have adverse systemic effects and, more importantly, are not especially effective at delivering a concentrated dose of the applicable drugs where they are truly needed, i.e., directly to the target tissues. The sealed chamber anatomy of the middle ear has, up until the present time, constituted a barrier to direct drug application.

Antibiotics are generally effective at very low levels and are often safe with very few, if any, side effects. Often antibiotics have little or no toxicity to mammalian cells. Thus, they may not retard, and can even enhance, wound healing. Antibiotics are generally of a narrow spectrum of antimicrobial activity. Furthermore, they often act on very specific sites in cell membranes or on very specific metabolic pathways. This can tend to make it relatively easy for bacteria to develop resistance to the antibiotic(s) (i.e., the genetically acquired ability to tolerate much higher concentrations of antibiotic) either through natural selection, transmission of plasmids encoding resistance, mutation, or by other means. Currently, the preferred method to treat both otitis media and otitis externa is the administration of systemic antibiotics.

The unresponsiveness of patients to antibiotics has progressively increased in recent years due to the emergence of antibiotic-resistant bacterial strains. Although amoxicillin, for example, is a preferred antibiotic used to treat otitis media, one-third of Haemophilis influenzae strains and at least three-quarters of *Moraxella catarhalis* strains are β-lactamase producers and are therefore inherently resistant to this antibacterial agent. In instances in which children are infected with such resistant strains, the administration of more potent antibiotics is required but these treatments often cause life-threatening responses. Despite the continued generation of new antibiotics, bacteria are certain to evolve resistance mechanisms to these novel antibiotics as well since antibiotics act on very specific metabolic routes or on specific physical structures. Bacteria have even been known to develop resistance to antibiotic cocktail mixtures.

In addition to the increased cost burden of unnecessary antibiotic treatment, the patients are exposed to the side effects of antibiotics and the attendant and significant risk of developing antibiotic resistance. Furthermore, antibiotics may also induce allergic reactions.

Antiseptics, on the other hand, tend to have broader spectrum of antimicrobial activity and often act by nonspecific means such as disruption of cell membranes, oxidation of cellular components, denaturation of proteins, etc. This nonspecific activity makes it difficult for resistance to develop to antiseptics. For example, there are very few reports of true resistance to antiseptics such as iodine, lower alcohols (ethanol, propanol, etc.), chlorhexidine, quaternary amine surfactants, and the like. These compounds, however, should be formulated to minimize or eliminate the potential for inactivation of the compounds or irritation of sensitive tissues, such as the middle ear, which can have a high level of microbial colonization during an episode of otitis media in certain otherwise healthy individuals, may be particularly sensitive to irritation.

The antimicrobial compositions are typically applied as a liquid (e.g., in the form of a drop deposited from, for example, a squeeze bottle with a dropper tip or a jar with screw in eye dropper (dropper bottle)) or are wicked into a support material and placed in contact with the TM. Once in contact, the composition in whole or part, traverses the TM and enters the middle ear. Alternatively, the compositions may be injected into the middle ear through the TM with an intact or ruptured TM. In yet another alternative, the antimicrobial compositions of the present invention may be instilled into the nasopharynx to contact the Eustachian tube or perhaps instilled directly into the Eustachian tube.

The compositions of this invention may provide effective reduction, prevention, or elimination of microbes, particularly bacteria, yeast and fungi, and in some cases viruses on the tissue to which it is applied and thereby help to prevent or eliminate infection of the internal spaces such as the middle ear and/or Eustachian tube as well as the external ear canal. Since the contaminating microbes may be of a relatively wide variety, the compositions of the present invention have a broad spectrum of activity.

Herein, to "kill or inactivate" means to render the microorganism ineffective by killing them (e.g., bacteria and fungi) or otherwise rendering them inactive (e.g., viruses). The present invention provides methods for killing bacteria such as *Staphylococcus* spp., *Streptococcus* spp., *Escherichia* spp., *Enterococcus* spp., *Pseudamonas* spp. *Streptococcus* spp., *Haemophilis* spp., or *Moraxella* spp. bacteria and combinations thereof, and more particularly *Staphylococcus aureus* (including antibiotic resistant strains such as methicillin resistant *Staphylococcus aureus*), *Staphylococcus epidermidis, Escherichia coli* (*E. coli*), *Pseudomonas aeruginosa* (*Pseudomonas ae.*), *Streptococcus pyogenes, Streptococcus pneumoniae, Haemophilis influenza*, or *Moraxella catarhalis* and combinations thereof which often are on or in the skin or mucosal tissue surround the exterior orifice of a subject. The method includes contacting the microorganism with an antimicrobial composition of the present invention in an amount effective to kill one or more microorganisms (e.g., bacteria and fungi) or inactivate one or more microorganisms (e.g., viruses, particularly herpes virus).

Significantly, certain embodiments of the present invention have a very low potential for generating microbial resistance. Thus, such compositions can be applied multiple times during a course of treatment to eradicate unwanted bacteria (such as, *Streptococcus pneumoniae, Haemophilis influenza, Moraxella catarhalis, Staphylococcus intermedius, Streptococcus* spp., *Pseudomonas* spp., *Proteus* spp., *Escherichia coli, Staphylococcus* sp., and the like). Furthermore, compositions of the present invention can be used for multiple treatment regimens on the same patient, in order to treat, for example, recurrent otitis media, without the fear of generating antimicrobial resistance. This can be particularly important for very young children who are prone to recurrent infection.

Also, preferred compositions described herein have a generally low irritation on the tissue to which it is applied. In particular the preferred compositions have low irritation and ototoxicity to middle ear tissue as described in the Examples. Also, certain preferred compositions described herein are substantive for relatively long periods of time to ensure adequate efficacy.

The methods of the present invention use antimicrobial (including, e.g., antiviral, antibacterial, and antifungal) compositions. These compositions include one or more antimicrobial components. In certain embodiments, the compositions also include one or more enhancers. Certain compositions also include one or more surfactants, one or more hydrophilic compounds, and/or one or more hydrophobic compounds. In certain embodiments, the hydrophobic component can be the same as the antimicrobial component, for example, when the antimicrobial component is an antimicrobial lipid. Some compositions are anhydrous or have very low water content. This may help chemical and/or physical stability of these compositions as well as to promote diffusion across the TM. Certain compositions of the present invention also comprise at least one penetration agent to facilitate diffusion into the middle ear and/or Eustachian tube when treating otitis media as well as penetrating cerumen in the outer ear canal when treating otitis externa.

The antimicrobial component(s) are preferably selected to ensure rapid broad spectrum activity without irritation, stinging, or burning. In certain embodiments, the antimicrobial component preferably has a solubility in water of at least 100 micrograms (μg) per 100 grams (g) deionized water and at most 1 g/100 g deionized water. In other embodiments the antimicrobial component is quite soluble in water having a solubility in excess of 1 g/100 g deionized water.

Preferably, the antimicrobial component is present in an amount of at least 0.05 wt-%, more preferably at least 0.1 wt-%. Unless otherwise specified, all weight percents are based on the total weight of a "ready to use" or "as used" composition.

The antimicrobial components can be antiseptics, antibiotics, or combinations thereof. Preferably, one or more antiseptics are used.

Herein, antiseptics are distinct from preservatives. Preservatives generally are used at very low levels since the purpose of these preservatives is to prevent bacterial growth in the composition, not to kill microbes on or in the tissue. They are typically added at levels of less than 1% and most often less than 0.1% by weight. Typical preservatives include parabens, formaldehyde donors, 2 phenoxyethanol, benzyl alcohol, quaternary ammonium surfactants such as benzalkonium chloride, and the like. When used on colonized or infected tissue at the industry standard concentrations they would not achieve adequate antimicrobial activity.

Suitable antiseptics include, for example antimicrobial lipids; phenolic antiseptics; or combinations thereof.

Certain compositions further include an enhancer component (i.e., an enhancer). Other components that can be included as well are surfactants, hydrophilic components, penetration agents and hydrophobic components. Compositions with hydrophobic components are typically used on mammalian tissues where visualization is not anticipated. Such components could interfere with vision when using fiber optic, otoscopic or other visualization techniques such as otoscopes inserted into the ear canal. Importantly, compositions described herein are capable of destroying microorganisms on or in mammalian tissue. Therefore, concentrations of components employed are generally greater than those that have been used to simply preserve certain topically applied compositions, i.e., prevent the growth of microorganism in topical compositions for purposes other than antisepsis. Depending on the application, many of these compounds at these concentrations can be irritating if delivered in simple aqueous or water soluble hydrophilic vehicle formulations. Many of the compositions described herein incorporate a substantial amount of a lipophilic or hydrophobic phase or water dispersible phase. The lipophilic phase is comprised of one or more water insoluble components. If delivered in a lipophilic phase, the irritation can be significantly reduced. The incorporation of the lipophilic phase may significantly improve the diffusion of the present compositions across the TM as well as reduce the irritation potential of the present compositions. Preferred lipophilic phase components have a solubility in water of less than 0.5% by weight and often less than 0.1% by weight. In addition, the antimicrobial lipid is preferably present at a concentration approaching or preferably exceeding the solubility limit of the lipophilic phase. Despite the presence of the hydrophobic phase, compositions described herein exhibit very effective and rapid antimicrobial activity. Preferred formulations incorporating lipophilic components can be easily dispersed in saline or water at 37° C. in order to allow the composition to be easily flushed from the tissue if irritation were to occur or if it became necessary to perform a scope procedure.

The relatively high viscosity of certain compositions described herein reduces migration that can be associated with other compositions, thus reducing irritation. Furthermore, the high viscosity allows the formulation to remain at the site of delivery. In addition, antimicrobial compositions that include hydrophilic components such as polyols (e.g., glycols including glycerin and polyethylene glycols) have little or no antimicrobial activity and can considerably enhance the antimicrobial activity of the compositions.

Importantly, certain compositions of the present invention have sufficient viscosity low enough to allow rapid entry into the ear canal if applied as an ear drop. Certain compositions may for example, melt, hydrate, disperse, or otherwise drop in viscosity when applied to the tissue. Preferred compositions intended to be delivered in a manner similar to an ear drop have a viscosity of less than 3000 cps, preferably less than 2000 cps, more preferably less than 1,000 cps, and most preferably less than 500 cps, e.g., less than 20 cps at 35° C. Importantly, the viscosity is sufficient and/or the composition wets and/or adheres to the tissue to prevent the composition from rapidly draining off the tissue once applied. Alternatively, the composition can be applied on a substrate that is placed in contact with the tissue (e.g., the external ear canal, the TM, etc.) or delivered as a salve. For these applications the viscosity at 23° C. and even at 35° C. can be much higher, as long as it is able to wet the tissue and deliver the antimicrobial component to the desired site (typically the external ear canal, tympanic membrane to be transported into the middle ear, middle ear, or Eustachian tube).

Preferred compositions wet and adhere well to bodily tissues (i.e., mammalian tissues such as the outer ear canal, middle ear, and the Eustachian tube tissue) and thus are very effective topically. These compositions are said to be "substantive." Similarly, preferred compositions also wet the Eustachian tube if instilled therein and may help Eustachian tube patency by lowering the surface tension of any fluid. As used herein a "patent" Eustachian tube is one that is at least partially functional and open to allow free equalization of air pressure. Typically, a normal appearing TM indicates a patent Eustachian tube. Thus, the present invention provides uses for the compositions.

For certain applications in which limited antimicrobial activity is desired, compositions containing antiseptics with limited spectrum of activity may be used. For example, in certain situations it may be desirable to kill or inactivate only one type or class of microorganism (e.g., Gram positive or Gram negative) as opposed to all the microorganisms present. In such situations, compositions described herein that contain an antimicrobial component without an enhancer component may be suitable.

For example, some of the antimicrobial components in the absence of an enhancer are only effective against Gram positive organisms. In most applications, broad spectrum antimicrobial activity is desired. Compositions containing a broad spectrum antiseptic such ascertain antimicrobial lipids, triclosan, as well as combinations thereof, optionally with an enhancer component are used in such situations.

Compositions described herein can be used to provide effective topical antimicrobial activity and thereby treat and/or prevent a wide variety of afflications. For example, they can be used in the treatment and/or prevention of afflictions that are caused, or aggravated by, microorganisms (e.g., Gram positive bacteria, Gram negative bacteria, fungi, protozoa, mycoplasma, yeast, viruses, and even lipid-enveloped viruses) entering a mammalian cavity or organ such as the bladder, upper sinuses, or peritoneal cavity.

Particularly relevant organisms that cause or aggravate such afflications include *Staphylococcus* spp., *Streptococcus* spp., *Pseudomonas* spp., *Enterococcus* spp., *Gardnerella* spp., *Corynebacterium* spp., *Bacteroides* spp., *Mobiluncus* spp., *Peptostreptococcus* spp., *Esherichia* spp., *Haemophilis* spp., and *Moraxella* spp. bacteria, as well as herpes virus, *Aspergillus* spp., *Fusarium* spp., *Candida* spp., as well as combinations thereof. Particularly virulent organisms include *Streptococcus pyogenes*, *Streptococcus pneumoniae*, *Haemophilis influenza*, *Moraxella catarhalis*, *Staphylococcus aureus* (including resistant strains such as *Methicillin Resistant Staphylococcus Aureus* (MRSA), *Staphylococcus epidermidis*, *Streptococcus pneumoniae*, *Enterococcus faecalis*, *Vancomycin Resistant Enterococcus* (VRE), *Pseudomonas auerginosa*, *Escherichia coli*, *Aspergillus niger*, *Aspergillus fumigatus*, *Aspergillus clavatus*, *Fusarium solani*, *Fusarium oxysporum*, *Fusarium chlamydosporum*, *Candida albicans*, *Candida glabrata*, *Candida krusei*, and combinations thereof.

Compositions described herein can be used for the prevention and/or treatment of one or more microorganism-caused infections or other afflictions. In particular, compositions described herein can be used for preventing and/or treating otitis media, otitis externa, and infections of the Eustachian tube. In sum, compositions described herein can be used for preventing and/or treating a wide variety of afflictions caused by microbial colonization and/or infection (e.g., fungi, viral, bacterial infections).

It should be understood that compositions described herein can be used in situations in which there are no clinical indications of an affliction. For example, compositions of the present invention can be used in methods of decolonizing at least a portion of the external ear canal, middle ear, Eustachian tube, and/or nasopharynx (i.e., the portion of the pharynx, i.e., throat, that lies above the point of food entry into the pharynx) of a subject of microorganisms.

Those of ordinary skill in the art will readily determine when a composition of the present invention provides antimicrobial activity using assay and bacterial screening methods well known in the art. One readily performed assay involves exposing selected known or readily available viable microorganism strains, such as *Enterococcus* spp., *Aspergillus* spp., *Escherichia* spp., *Staphylococcus* spp., *Streptococcus* spp., *Haemophilis* spp., or *Moraxella* spp., *Pseudomonas* spp., or *Salmonella* spp., to a test composition at a predetermined bacterial burden level in a culture media at an appropriate temperature. For the preferred compositions described herein this is most conveniently done by the Antimicrobial Kill Rate Test described in the Examples Section.

Briefly, after a sufficient contact time, an aliquot of a sample containing the exposed bacteria is collected, diluted, and plated out on agar. The plated sample of bacteria is incubated for forty-eight hours and the number of viable bacterial colonies growing on the plate is counted. Once colonies have been counted the reduction in the number of bacteria caused by the test composition is readily determined. Bacterial reduction is generally reported as $\log_{10}$ reduction determined by the difference between the $\log_{10}$ of the initial inoculum count and the $\log_{10}$ of the inoculum count after exposure. Preferred compositions described herein have an average of at least a 4 log reduction in test bacteria in 10 minutes.

Many of the preferred compositions were tested as described in the Examples Section for antimicrobial activity against MRSA (Gram positive, ATCC Number 16266), *E. coli* (Gram negative, ATCC Number 11229), and *Pseudomonas aeruginosa* (Gram negative, ATCC Number 15442). In general, the *Pseudomonas aeruginosa* is often the most difficult to kill. Preferred compositions described herein also exhibit very rapid antimicrobial activity. As shown in the Examples Section, preferred formulations are able to achieve an average log reduction of at least 4 log against these three organisms after a 10 minute exposure and preferably after a 5 minute exposure. More preferred compositions are able to achieve an average log reduction of at least 5 log, and even more preferably an average log reduction of at least 6 log, against these three organisms after a 10 minute exposure (and more preferably after 1 minute of exposure time) and preferably after a 5 minute exposure.

For residual antimicrobial efficacy, compositions described herein preferably maintain an average log reduction of at least 1 log, more preferably at least 1.5 log, and even more preferably at least 2 log, for at least 0.5 hour, more preferably at least 1 hour, and even more preferably at least 3 hours after application to an affected site. This is most conveniently tested by applying the composition on the forearm of a subject. To test this, a composition was applied to the forearm of a subject as a uniform wet coating in an amount of approximately 4 milligrams per square centimeter ($mg/cm^2$) to the forearm of a healthy subject and allowed to thoroughly dry (typically a minimum of 10 minutes) over an area of approximately 5×5 cm. The dried composition was gently washed with 23° C. normal saline (0.9% by weight sodium chloride). The saline washed site was exposed to a known quantity of bacteria in an innoculum of $10^6$ bacteria/mL (typically *Staphylococcus epidermidis* or *E. coli*) for 30 minutes. The bacteria were recovered and treated with an effective neutralizer and incubated to quantify the bacteria remaining. Particularly preferred compositions retain at least 1 log reduction and preferably at least 2 log reduction of bacteria after a gentle rinse with 500 mL saline poured over the site by placing the saline container as close to the site as possible so as to not have the saline fall onto the site.

Significantly, certain embodiments of the present invention have a very low potential for generating microbial resistance. For example, preferred compositions described herein have an increase in the ratio of final to initial MIC levels (i.e., minimum inhibitory concentration) of less than 16, more preferably less than 8, and even more preferably less than 4. Such an emergence of resistance assay should be carried out such that the microorganisms are subjected initially to sub MIC levels (e.g., ½ the MIC) of antimicrobial lipid and after 24 hours the microorganisms passed into broth containing twice the concentration of antimicrobial lipid. This is repeated for 8 days and each day microorganisms are removed to determine the new MIC. Thus, such compositions can be applied multiple times over one or more days to treat topical infections or to eradicate unwanted bacteria (such as nasal colonization of *Staphylococcus aureus*).

Preferred compositions of the present invention have a generally low irritation level for skin and mucosal membranes (including the external ear canal, middle ear, Eustachian tube and nasopharangyl cavity). For example, certain preferred compositions of the present invention are no more irritating than Cortisporin Otic Solution, Sterile, commercially available from Monarch Pharmaceuticals, Inc.

Preferred compositions described herein are substantive for relatively long periods of time to ensure adequate efficacy. For example, certain compositions described herein remain at the site of application with antimicrobial activity for at least 4 hours and more preferably at least 8 hours.

Preferred compositions described herein are physically stable. As defined herein "physically stable" compositions are those that do not significantly change due to substantial precipitation, crystallization, phase separation, and the like, from their original condition during storage at 23° C. for at least 3 months, preferably for at least 6 months, and more preferably for at least 2 years. Particularly preferred compositions are physically stable if a 10-milliliter (10-mL) sample of the composition when placed in a 15-mL conical-shaped graduated plastic centrifuge tube (Corning) and centrifuged at 500×g and preferably at 1000×g and most preferably at 2000×g have no visible phase separation in the bottom or top of the tube. Some of the compositions may be thickened using components which crystallize such as polyethylene glycols, petrolatum, microcrystalline wax, certain emulsifiers, and the like. These compositions are only presumed to be "unstable" if phase separation occurs. Alternatively, compositions having relatively low viscosity, e.g., less than 200 cps, preferably less than 100 cps, and more preferably less than 50 cps, and most preferably less than 20 cps may be shaken prior to use if they are not physically stable, e.g., emulsions or suspensions that have the tendency to form separate phases.

Note that the compositions are preferably free of air so that when applied to the tissue all of the tissue surfaces are adequately covered. Alternatively, foams may be used, however, these may require some tissue manipulation to ensure proper coverage.

Preferred compositions described herein exhibit good chemical stability. This can be especially a concern with some of the conventional antimicrobial components. The pH of any of the antimicrobial compositions is preferably greater than 2.5 and preferably greater than 3 to in order to avoid tissue irritation. Preferably for external ear applications the pH is kept less than 7 to mimic the natural tissue and avoid invasion by abnormal microbial flora. Preferably, compositions comprising antimicrobial lipid esters and water are buffered close to pH 7, e.g 5-9 and preferably 6-8 in order to reduce the possibility of hydrolysis. Alternatively or additionally, water soluble hydrophilic components may be added to reduce the activity of the water. Compositions comprising certain phenolic antiseptics such as triclosan, petrolatum and other light sensitive components additionally must be protected from Ultra Violet (UV) light to avoid chemical breakdown. This can be accomplished through the use of UV absorbers in the packaging or by packing the composition in a UV impermeable opque package. Antimicrobial fatty acid esters and fatty alcohol esters of hydroxy acids, and fatty acid esters of hydroxyacids can often undergo transesterification and hydrolysis. This can be prevented by formulating without potentially reactive excipients (e.g., those with free OH or COOH group) or by formulating with an excipients that if reaction occurred would yield the same compound (e.g., formulation of a glycerol monolaurate formulation with glycerin). Hydrolysis is most easily prevented by formulating in anhydrous or nearly anhydrous conditions.

Preferred compositions retain at least 85%, more preferably at least 90%, even more preferably at least 92%, and even more preferably at least 95%, of the antimicrobial component after aging for 4 weeks at 40° C. (an average of three samples) beyond the initial 5-day equilibration period at 23° C. The most preferred compositions retain an average of at least 97% of the antimicrobial component after aging for 4 weeks at 40° C. in a sealed container beyond the initial 5-day equilibration period at 23° C. The percent retention is understood to mean the weight percent of antimicrobial component retained. This is determined by comparing the amount remaining in a sample aged (i.e., aged beyond the initial 5-day equilibration period) in a sealed container that does not cause degradation, to the actual measured level in an identically prepared sample (preferably from the same batch) and allowed to sit at 23° C. for five days. The level of antimicrobial component is preferably determined using gas chromatography or other suitable sensitive analytical technique.

Generally, the compositions of this invention may be in one of the following forms:

A hydrophobic ointment: The compositions are formulated with a hydrophobic base (e.g., petrolatum, thickened or gelled water insoluble oils, and the like) and optionally having a minor amount of a water soluble phase.

An oil-in-water emulsion: The compositions may be formulations in which the antimicrobial component is emulsified into an emulsion comprising a discrete phase of a hydrophobic component and a continuous aqueous phase that includes water and optionally one or more polar hydrophilic carrier(s) as well as salts, surfactants, emulsifiers, and other components. These emulsions may include water-soluble or water-swellable polymers as well as one or more emulsifier(s) that help to stabilize the emulsion. These emulsions generally have higher conductivity values, as described in International Publication WO 2003/028767. The antimicrobial component(s) may be in one or both phases depending on the solubility.

A water-in-oil emulsion: The compositions may be formulations in which the antimicrobial component is incorporated into an emulsion that includes a continuous phase of a hydrophobic component and an aqueous phase that includes water and optionally one or more polar hydrophilic carrier(s) as well as salts or other components. These emulsions may include oil-soluble or oil-swellable polymers as well as one or more emulsifier(s) that help to stabilize the emulsion. The antimicrobial component(s) may be in one or both phases depending on the solubility.

Aqueous gels: These systems include an aqueous phase which has distributed therein the antimicrobial component. The antimicrobial may be part of a discrete phase such as an oil in water emulsion previously described or it may be solubilized through the use of hydrophilic components capable of dissolving the antimicrobial component. Typically these compositions may be thickened to achieve a slightly higher viscosity but generally have a viscosity of less than about 3000 cps if they are to be delivered to the ear canal as a drop. Much higher viscosities are acceptable if the composition is delivered as a salve with an appropriate applicator capable if getting the composition deep into the ear canal for treatment of otitis externa or in contact with the tympanic membrane and/or delivery directly to the middle ear for treatment of otitis media. For example, if impregnated into a porous substrate the viscosity may be low as previously described or much higher. Furthermore, some compositions may decrease in viscosity when warmed up upon contact with the tissue or after hydrating in the ear canal or in the nasopharynx. In these systems the viscosity at room temperature may be much higher, e.g., 50,000 cps, 100,000 cps or higher. Typically the viscosity at 35° C., however, is less than 15000 cps, more preferably less than 10,000 cps, even more preferably less than 1,000 cps, even more preferably less than 500 cps. The viscosity is determined using the Viscosity Test described herein.

Systems comprising water can be thickened by suitable natural, modified natural, or synthetic water soluble polymers as described below. Alternatively, the aqueous systems can be thickened using suitable emulsifiers such as polyethoxylated alkyl chain surfactants that effectively thicken the composition as well as other nonionic, cationic, or anionic emulsifier systems. Preferably, cationic or anionic emulsifier systems are chosen since some polyethoxylated emulsifiers can inactivate the antimicrobial lipids especially at higher concentrations. For certain embodiments, anionic emulsifier systems are used. Examples include the nonioinic systems such as POLAWAX, COSMOWAX, and CROTHIX systems as well as cationic (BEHENYL TMS) and anionic (CRODAPHOS CES) systems from Croda Inc. Systems comprising hydrophobic components as the continuous phase can be thickened using oil soluble polymers such as petroleum based products, polyacrylates, and the like. These may also be thickened using crystalline materials such as microcrystalline wax NF as well as certain emulsifiers such as those mentioned above which crystallize and resulting in thickening, and the like.

Hydrophilic gels and creams: These are systems in which the continuous phase includes at least one water soluble hydrophilic component other than water present in greatest amount. The formulations may optionally also contain water up to 20% by weight or more. Higher levels may be suitable in some compositions. Suitable hydrophilic components include one or more glycols such as polyhydric alcohols, propylene glycol, dipropylene glycol, polypropylene gycols having a molecular weight less than about 500 and preferably less than 450, butylene glycols, etc., polyethylene glycols (PEG), random or block copolymers of ethylene oxide, propylene oxide, and/or butylene oxide, polyalkoxylated surfactants having one or more hydrophobic moieties per molecule, silicone copolyols, as well as combinations thereof, and the like. One skilled in the art will recognize that the level of ethoxylation should be sufficient to render the hydrophilic component water at 23° C. These compositions may be thickened using conventional crystallizable polymers and emulsifiers such as polyethylene glycols and polyethoxylated alkyl ethers and esters. Alternatively, they may be thickened using one or more soluble or swellable polymers such as polyvinylpyrrolidone (povidone), polyvinylalcohol (PVA), copolymers of N-vinyl pyrrolidone, PVAs having vinyl acetate groups such as those made by partial hydrolysis of polyvinyl acetate, polyacrylates, as well as natural polymers and gums such as modified celluloses (e.g., hydroxypropylcellulose, carboxymethyl cellulose, hydroxyethyl cellulose, and the like), guar gum, alginates, xanthan gums, starches, and the like, as well as chemical modifications there of such as but not limited to cationic forms. In most embodiments, the water content is less than 20%, preferably less than 10%, and more preferably less than 5% by weight of the composition. These systems may optionally comprise an internal hydrophobic phase. The hydrophobic phase may further comprise a penetration agent.

Dispersible Gels and Creams: These are systems in which the continuous phase includes at least one water dispersible hydrophilic component in greatest amount. The water dispersible components are typically amphipathic compounds such as polyethoxylated ethers and esters. For example, particularly preferred components include PEG 4-PEG 50 glyceryl alkylates formed, for example, by making the alkyl esters of polyethoxylated glycerin, PEG 110-PEG 100 castor oil (or hydrogenated castor oil) such as PEG 30 castor oil and PEG 40 hydrogenated castor oil, PEG 3-PEG 40 esters or ethers of unsaturated lipids such as PEG 6 oleate, PEG 8 dioleate, oleth-6, and the like. In most embodiments, the water content is less than 20%, preferably less than 10%, and more preferably less than 5% by weight of the composition.

Antimicrobial Component

The antimicrobial component can include antiseptics, antibiotics, or combinations thereof. Typically, and preferably, the antimicrobial component includes antiseptics. The antimicrobial component is generally considered the main active component of the compositions described herein.

The antimicrobial component preferably includes an antiseptic selected from one of the following classes: an antimicrobial lipid; a phenolic antiseptic; a cationic antiseptic; or combinations thereof. Particularly preferred antimicrobial components include an antiseptic selected from an antimicrobial lipid; a phenolic antiseptic; or combinations thereof.

Antibiotics

Examples of preferred antibiotics include neomycin sulfate, bacitracin, mupirocin, polymyxin, gentamycin, nitrofurantoin, sulfamethoxazole trymethoprim, rifampin, tetracycline, lysostaphin, and combinations thereof. Suitable antibiotic agents include, but are not limited to, beta-lactam antibacterials such as natural and synthetic penicillin type agents including penam penicillins (such as benzyl penicillin, phenoxymethyl penicillin, coxacillin, nafcillin, methicillin, oxacillin, amoxycillin, temocillin, ticarcillin, and the like), penicillinase-stable penicillins, acylamino and carboxypenicillins (such as piperacillin, azlocillin, mezlocillin, carbenicillin, temocillin, ticarcillin, and the like), and broader spectrum penicillins (such as streptomycin, neomycin, framycetin, gentamicin, apramycin, amikacin, spectinomycin, amoxycillin, ampicillin, and the like), cephalosporins, macrolides (such as tylosin, tilmicosin, aivlosin, erythromycin, azithromycin, spiramycin, josamycin, kitasamycin, and the like), lincosamides (such as lincomycin, clindamycin, pirlimycin, and the like), pleuromutilins (such as tiamulin, valnemulin, and the like), polypeptides, glycopeptides (such as vancomycin, and the like), polymixins (such as polymixin B, polymixin E, and the like), sulfonamides (such as sulfamethazine, sulfadiazine, silver sulfadiazine, sulfatroxazole, sulfamethoxypyridazine, sulfanilamide, sulfamethoxazole, sulfisoxazole, sulfamethizole, mafenide, and the like, alone or in combination with trimethoprim), chloramphenicol, thiamphenicol, florfenicol, tetracycline type agents (such as tetracycline, chlortetracycline, oxytetracycline, domeclocycline, doxycycline, minocycline, and the like), quinolones and fluoroquinolones (such as ciprofloxacin, enoxacin, grepafloxacin, levofloxacin, lomefloxacin, norfloxacin, ofloxacin, sparfloxacin, trovafloxacin, cinocacin, nalidixic acid, and the like), tiamulin, colistin, meropenem, sulbactam, tazobactam, methacycline, pyrimethamine, sulfacetamide, oxazolidinones, e.g., eperezolid, linezolid, N-((5S)-3-(3-fluoro-4-(4-(2-fluoroethyl)-3-oxy-1-piperazinyl)phenyl-2-oxy-5-oxazolidinyl)methyl)acetamide, (S)—N-((3-(5-(3-pyridyl) thiophen-2-yl)-2-oxy-5-oxazolidinyl)methyl)acetamide, 2,2-difluoro-N-({(5S)-3-[3-fluoro-4-(4-glycoloylpiperazin-1-yl)pheny-l]-2-oxo-1,3-oxazolidin-5-yl}methyl)ethanethioamide, (S)—N-((3-(5-(4-pyridyl)pyrid-2-yl)-2-oxy-5-oxazolidinyl)methyl)acetamide hydrochloride, and the like, aminoglycosides (kanamycin, tobramycin, netilmicin, and the like), aminocyclitols, amphenicol, ansamycin, carbaphenern, cephamycin, rifampicin, monobactam, oxacephem, streptogramins (such as quinupristin, dalfopristin, and the like), cycloserines, mupirocin, urea hydroxamates, folic acid analogs (such as trimethoprim, and the like), antibiotic-type antineoplastic agents (such as aclarubicin, actinomycin D, actinoplanone, aeroplysinin derivative, Nippon Soda anisomycins, anthracycline, azinomicyin-A, busucaberin, bleomycin sulfate, bryostatin-1, calichemycin, chromoximycin, dactinomycin, daunorubicin, ditrisarubicin B, doxorubicin, doxorubicin-fibrinogen, elsamicin-A, epirubicin, erbstatin, esorubicin, esperamicin-Alb, fostriecin, glidobactin, gregatin-A, grincamycin, herbimycin, idarubicin, illudins, kazusamycin, kesarirhodins, menogaril, mitomycin, mitoxantorone, mutamycin, mycophenolate mofetil, neoenactin, oxalysine, oxaunomycin, peplomycin, pilatin, pirarubicin, porothramycin, pyrindamycin A, rapamycin, rhizoxin, rodorubicin, sibanomicin, siwenmycin, sorangicin-A, sparsomycin, steffimycin B, talisomycin, terpentecin, thrazine, tricrozarin A, zorubicin, systemic antibacterials (such as 2,4-diaminopyrimidine), nitrofuran sulfones, narbofloxacin, and the like, and combinations thereof.

The antibiotics used in compositions of the present invention are typically used in combination with an antiseptic. Preferred compositions, however, are free of antibiotics due to the chance of resistance formation.

Antimicrobial Lipids

The antimicrobial lipid component is that component of the composition comprising at least one branched or straight chain alkyl or alkylene of at least 6 carbon atoms, preferably at least 7 carbon atoms and preferably at least 8 carbon atoms that provides at least part of the antimicrobial activity. That is, the antimicrobial lipid component has at least some antimicrobial activity for at least one microorganism.

In certain embodiments, the antimicrobial lipid preferably has a solubility in water of no greater than 1.0 gram per 100 grams (1.0 g/100 g) deionized water. More preferred antimicrobial lipids have a solubility in water of no greater than 0.5 g/100 g deionized water, even more preferably, no greater than 0.25 g/100 g deionized water, and even more preferably, no greater than 0.10 g/100 g deionized water. Preferred antimicrobial lipids have a solubility in deionized water of at least 100 micrograms (μg) per 100 grams deionized water, more preferably, at least 500 μg/100 g deionized water, and even more preferably, at least 1000 μg/100 g deionized water.

The antimicrobial lipids preferably have a hydrophile/lipophile balance (HLB) of at most 6.2, more preferably at most 5.8, and even more preferably at most 5.5. The antimicrobial lipids preferably have an HLB of at least 3, preferably at least 3.2, and even more preferably at least 3.4.

Preferred antimicrobial lipids are uncharged and have an alkyl or alkenyl hydrocarbon chain containing at least 7 carbon atoms.

In certain embodiments, the antimicrobial lipid component preferably includes one or more fatty acid esters of a polyhydric alcohol, fatty ethers of a polyhydric alcohol, or alkoxylated derivatives thereof (of either or both of the ester and ether), or combinations thereof. More specifically and preferably, the antimicrobial component is selected from the group consisting of a (C7-C14)saturated fatty acid ester of a polyhydric alcohol (preferably, a (C7-C12)saturated fatty acid ester of a polyhydric alcohol, more preferably, a (C8-C12)saturated fatty acid ester of a polyhydric alcohol), a (C8-C22)unsaturated fatty acid ester of a polyhydric alcohol (preferably, a (C12-C22)unsaturated fatty acid ester of a polyhydric alcohol), a (C7-C14)saturated fatty ether of a polyhydric alcohol (preferably, a (C8-C12)saturated fatty ether of a polyhydric alcohol, more preferably, a (C8-C12)saturated fatty ether of a polyhydric alcohol), a (C8-C22)unsaturated fatty ether of a polyhydric alcohol (preferably, a (C12-C22) unsaturated fatty ether of a polyhydric alcohol), an alkoxylated derivative thereof, and combinations thereof. Preferably, the esters and ethers are monoesters and monoethers, unless they are esters and ethers of sucrose in which case they can be monoesters, diesters, monoethers, or mono ethers. Various combinations of monoesters, diesters, monoethers, and diethers can be used in a composition of the present invention.

A fatty acid ester of a polyhydric alcohol is preferably of the formula $(R^1—C(O)—O)_n—R^2$, wherein $R^1$ is the residue of a (C7-C14)saturated fatty acid (preferably, a (C7-C12) saturated fatty acid, more preferably, a (C8-C12)saturated fatty acid), or a (C8-C22)unsaturated fatty acid (preferably, a C12-C22)unsaturated, including polyunsaturated, fatty acid), $R^2$ is the residue of a polyhydric alcohol (typically and preferably, glycerin, propylene glycol, and sucrose, although a wide variety of others can be used including pentaerythritol, sorbitol, mannitol, xylitol, etc.), and n=1 or 2. The $R^2$ group includes at least one free hydroxyl group (preferably, residues of glycerin, propylene glycol, or sucrose). Preferred fatty acid esters of polyhydric alcohols are esters derived from C7, C8, C9, C10, C11, and C12 saturated fatty acids. For embodiments in which the polyhydric alcohol is glycerin or propylene glycol, n=1, although when it is sucrose, n=1 or 2.

Exemplary fatty acid monoesters include, but are not limited to, glycerol monoesters of lauric (mono laurin), caprylic (mono caprylin), and capric (mono caprin) acid, and propylene glycol monoesters of lauric, caprylic, and capric acid, as well as lauric, caprylic, and capric acid monoesters of sucrose. Other fatty acid monoesters include glycerin and propylene glycol monoesters of oleic (18:1), linoleic (18:2), linolenic (18:3), and arachonic (20:4) unsaturated (including polyunsaturated) fatty acids. As is generally known, 18:1, for example, means the compound has 18 carbon atoms and 1 carbon-carbon double bond. Preferred unsaturated chains have at least one unsaturated group in the cis isomer form. In certain preferred embodiments, the fatty acid monoesters that are suitable for use in the present composition include known monoesters of lauric, caprylic, and capric acid, such as that known as GML or the trade designation LAURICIDIN (the glycerol monoester of lauric acid commonly referred to as monolaurin or glycerol monolaurate), glycerol monocaprate, glycerol monocaprylate, propylene glycol monolaurate, propylene glycol monocaprate, propylene glycol monocaprylate, and combinations thereof.

Exemplary fatty acid diesters of sucrose include, but are not limited to, lauric, caprylic, and capric diesters of sucrose as well as combinations thereof.

A fatty ether of a polyhydric alcohol is preferably of the formula $(R^3-O)_n-R^4$, wherein $R^3$ is a (C7-C14)saturated aliphatic group (preferably, a (C7-C12)saturated aliphatic group, more preferably, a (C8-C12)saturated aliphatic group), or a (C8-C22)unsaturated aliphatic group (preferably, a (C12-C22)unsaturated, including polyunsaturated, aliphatic group), $R^4$ is the residue of glycerin, sucrose, or propylene glycol, and n=1 or 2. For glycerin and propylene glycol n=1, and for sucrose n=1 or 2. Preferred fatty ethers are monoethers comprising (C7-C14)alkyl groups (more preferably (C7-C12)alkyl groups, and even more preferably, (C8-C12)alkyl groups).

Exemplary fatty monoethers include, but are not limited to, laurylglyceryl ether, caprylglycerylether, caprylylglyceryl ether, laurylpropylene glycol ether, caprylpropyleneglycol ether, and caprylylpropyleneglycol ether. Other fatty monoethers include glycerin and propylene glycol monoethers of oleyl (18:1), linoleyl (18:2), linolenyl (18:3), and arachonyl (20:4) unsaturated and polyunsaturated fatty alcohols. In certain preferred embodiments, the fatty monoethers that are suitable for use in the present composition include laurylglyceryl ether, caprylglycerylether, caprylyl glyceryl ether, laurylpropylene glycol ether, caprylpropyleneglycol ether, caprylylpropyleneglycol ether, and combinations thereof. Unsaturated chains preferably have at least one unsaturated bond in the cis isomer form.

Alternatively, the antimicrobial lipid can be a (C7-C14) fatty alcohol ester (preferably a (C8-C12)fatty alcohol ester) of a (C2-C8)hydroxycarboxylic acid (also often referred to as a (C7-C14) or (C2-C8)hydroxycarboxylic acid ester of a (C8-C12)fatty alcohol), a (C8-C22)mono- or poly-unsaturated fatty alcohol ester of a (C2-C8)hydroxycarboxylic acid (also often referred to as a (C2-C8)hydroxycarboxylic acid ester of a (C8-C22)mono- or poly-unsaturated fatty alcohol)), or alkoxylated derivatives thereof. The hydroxycarboxylic acid moiety can include aliphatic and/or aromatic groups. For example, fatty alcohol esters of salicylic acid are possible.

For some embodiments, the antimicrobial lipid is a (C7-C14)fatty alcohol ester (preferably a monoester) of a (C2-C8) hydroxycarboxylic acid (preferably a (C7-C12)fatty alcohol ester (preferably a monoester) of a (C2-C8)hydroxycarboxylic acid, and more preferably a (C8-C12)fatty alcohol ester (preferably a monoester) of a (C2-C8)hydroxycarboxylic acid, a (C8-C22)mono- or poly-unsaturated fatty alcohol ester of a (C2-C8)hydroxycarboxylic acid, or combinations thereof. Herein, a "monoester" is that there is only 1 alkyl or aralkyl group and thus a free hydroxyl group.

The hydroxyacids typically have one hydroxyl group and one carboxylic acid group. They are preferably selected from alpha- and beta-hydroxyacids described below. The fatty alcohols are most preferably straight or branched alkyl alcohols having 7-14 carbon atoms, and most preferably 7-12 carbon atoms, or a (C8-C22)unsaturated fatty alcohol (preferably, a C12-C22)unsaturated, including polyunsaturated, fatty alcohol).

A fatty alcohol ester of a hydroxyl functional carboxylic acid preferably has the formula:

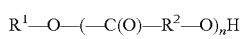

wherein: $R^1$ is the residue of a (C7-C14)saturated alkyl alcohol (preferably, a (C7-C12)saturated alkyl alcohol, more preferably, a (C8-C12)saturated alkyl alcohol), or a (C8-C22) unsaturated alcohol (including polyunsaturated alcohol); $R^2$ is the residue of a hydroxycarboxylic acid wherein the hydroxycarboxylic acid has the following formula:

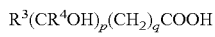

wherein: $R^3$ and $R^4$ are each independently H or a (C1-C8) saturated straight, branched, or cyclic alkyl group, a (C6-C12)aryl group, a (C6-C12)aralkyl or (C6-C12)alkaryl group (wherein the alkyl groups of the aralkyl and alkaryl groups are saturated straight, branched, or cyclic), wherein $R^3$ and $R^4$ may be optionally substituted with one or more carboxylic acid groups; p=1 or 2; and q=0-3; and n=1, 2, or 3. The $R^3$ group may include one or more free hydroxyl groups, but preferably is free of hydroxyl groups. Preferred fatty alcohol esters of hydroxycarboxylic acids are esters derived from branched or straight chain C8, C9, C10, C11, and C12 alkyl alcohols. Preferred hydroxyacids typically have one hydroxyl group and one carboxylic acid group.

Exemplary fatty alcohol esters of hydroxycarboxylic acids include, but are not limited to, (C7-C14), and preferably (C8-C12), fatty alcohol esters of lactic acid such as octyl lactate, 2-ethylhexyl lactate (PURASOLV EHL from Purac, Lincolnshire, Ill.), lauryl lactate (CHRYSTAPHYL 98 from Chemic Laboratories, Canton, Mass.), lauryl lactyl lacate, 2-ethylhexyl lactyl lactate; (C7-C14), and preferably (C8-C12), fatty alcohol esters of 3-hydroxybutanoic acid, mandelic acid, gluconic acid, tartaric acid, and salicylic acid.

The fatty acid esters and fatty ethers of polyhydric alcohols and/or hydroxycarboxylic esters of fatty alcohols can be alkoxylated, preferably ethoxylated and/or propoxylated, by conventional techniques. The alkoxylated derivatives have less than 5 moles of alkoxide per mole of polyhydric alcohol or hydroxyl acid. Alkoxylating compounds are preferably selected from the group consisting of ethylene oxide, propylene oxide, and mixtures thereof, and similar oxirane compounds. The alkoxylated derivatives of the aforementioned fatty acid esters, fatty ethers, and hydroxycarboxylic esters of fatty alcohols (e.g., one which is ethoxylated and/or propoxylated on the remaining alcohol group(s)) also have antimicrobial activity as long as the total alkoxylate is kept relatively low. In the case where the antimicrobial lipid esters and ethers having at least one free —OH group are ethoxylated, the total moles of ethylene oxide is preferably less than 5, and more preferably less than 2.

Alternatively, other antimicrobial lipids include (C6-C14) alkyl carboxylic acids, and (C8-C22)mono- or poly-unsaturated carboxylic acids. These antimicrobial lipids include (C6-C14), preferably (C7-C12), and more preferably (C8-C12)

straight chain or branched chain alkyl carboxylic acids, such as heptanoic, carpic, caprylic, undecylenic, 2-ethylhexanoic, and lauric acids. These are often referred to as fatty acids. As used herein the term "fatty" includes both even and odd number of carbon atoms in alkyl and alkenyl acids which may be linear or branched. Also included are (C8-C22)mono- or poly-unsaturated fatty acids (i.e., carboxylic acids). Examples include oleic, linoleic, linolenic, and arachidonic acids. Other antimicrobial lipids include esters of these carboxylic acids with hydroxyfunctional alkyl acids (alkyl carboxylate esters of carboxylic acids) such as lauroyl lactylate, capryloyl lactylate, or caproyl lactylate. A fatty acid ester of a hydroxyl functional carboxylic acid (i.e., alkyl carboxylate ester carboxylic acid) preferably has the formula:

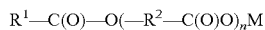

$$R^1-C(O)-O(-R^2-C(O)O)_nM$$

wherein $R^1$ is the residue of a (C6-C14)saturated alkyl carboxylic acid (preferably, a (C7-C12)saturated alkyl carboxylic acid, more preferably, a (C8-C12)saturated allyl carboxylic acid) or a (C8-C22)unsaturated alkylene carboxylic acid (including polyunsaturated carboxylic acid), $R^2$ is the residue of a hydroxycarboxylic acid wherein the hydroxycarboxylic acid has the following formula:

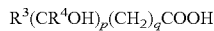

$$R^3(CR^4OH)_p(CH_2)_qCOOH$$

wherein: $R^3$ and $R^4$ are each independently H or a (C1-C8) saturated straight, branched, or cyclic allyl group, a (C6-C12) aryl group, or a (C6-C12)aralkyl or (C6-C12)alkaryl group (wherein the alkyl groups of the aralkyl and alkaryl groups are saturated straight, branched, or cyclic groups), wherein $R^3$ and $R^4$ may be optionally substituted with one or more carboxylic acid groups; p=1 or 2; and q=0-3; and n=1, 2, or 3. The $R^3$ group may include one or more free hydroxyl groups. Preferred fatty acid esters of hydroxycarboxylic acids are esters derived from branched or straight chain C8, C9, C10, C11, and C12 alkyl carboxylic acids. M is a cationic counterion such as H, Na, K, Li, ammonium, or a protonated tertiary amine such as triethanolamine or a quaternary ammonium group. M also may be polyvalent metals such as Ca, Mg, Fe, and the like in which case there would need to be a stoichiometric ratio of lipid ester carboxylate to metal ion.

The fatty acid esters of hydroxyl carboxylic acids are preferably formed by esterification of a (C6-C14)saturated linear or branched alkylcarboxylic acid or a (C8-C22)mono- or poly-unsaturated fatty acid with a hydroxyfunctional alkyl carboxylic acid. Preferred such antimicrobial lipids include a (C8-C12)fatty acid ester of a (C2-C8)hydroxycarboxylic acid, a (C8-C22)mono- or poly-unsaturated fatty acid ester of a (C2-C8)hydroxycarboxylic acid, or combinations thereof.

A commercially available example of an alkyl carboxylate ester of an alkyl carboxylic acid is PATIONIC 122A (caproyl lactyl lactate) available from RITA Corp. Other preferred compounds of this class are 2-ethylhexoyl lactate, lauroyl lactylate and lauroyl lactyl lactate. It is preferred to formulate these antiseptics in the presence of a hydrophobic component and/or an emulsifier/surfactant.

At least a portion of the carboxylic acid preferably is present in the acid or protonated form. This form has significantly greater activity than the neutralized salt form. Since these acids can also be relatively irritating they are preferably formulated in compositions based on hydrophobic vehicles such as emollient oils or petrolatum which may optionally contain a hydrophilic component. The pH of aqueous compositions (or the aqueous phase of the compositions) formulated with these antiseptics typically range from 3 to 8 and most preferably from 3 to 6.

The compositions described herein include one or more antimicrobial lipids at a suitable level to produce the desired result. Such compositions preferably include a total amount of such material of at least 0.01 percent by weight (wt-%), more preferably at least 0.1 wt-%, even more preferably at least 0.25 wt-%, even more preferably at least 0.5 wt-%, and even more preferably at least 1 wt-%, based on the total weight of the "ready to use" or "as used" composition. In a preferred embodiment, they are present in a total amount of up to 99% by weight if they are used at the antimicrobial component as well as the vehicle. Generally, they are used at no greater than 60 wt-%, more preferably no greater than 50 wt-%, even more preferably no greater than 30 wt-%, even more preferably no greater than 20 wt-%, and even more preferably no greater than 10 wt-%, based on the "ready to use" or "as used" composition.

Many antimicrobial lipids are effective at levels of less than 5% by weight of composition. Certain compositions may be higher in concentration if they are intended to be diluted prior to use or if the antimicrobial lipid is used as the vehicle. For example, certain antimicrobial lipids that are liquid at room temperature can be used as the antimicrobial component and the vehicle and thus may be present in concentrations as high as 90% or more.

Preferred compositions described herein that include one or more fatty acid monoesters, fatty monoethers, or alkoxylated derivatives thereof can also include a small amount of a di- or tri-fatty acid ester (i.e., a fatty acid di- or tri-ester), a di- or tri-fatty ether (i.e., a fatty di- or tri-ether), or alkoxylated derivative thereof. Preferably, such components are present in an amount of no more than 50 wt-%, more preferably no more than 40 wt-%, even more preferably no more than 25 wt-%, even more preferably no more than 15 wt-%, even more preferably no more than 10 wt-%, even more preferably no more than 7 wt-%, even more preferably no more than 6 wt-%, and even more preferably no more than 5 wt-%, based on the total weight of the antimicrobial lipid component. For example, for monoesters, monoethers, or alkoxylated derivatives of glycerin, preferably there is no more than 15 wt-%, more preferably no more than 10 wt-%, even more preferably no more than 7 wt-%, even more preferably no more than 6 wt-%, and even more preferably no more than 5 wt-% of a diester, diether, triester, triether, or alkoxylated derivatives thereof present, based on the total weight of the antimicrobial lipid components present in the composition. However, as will be explained in greater detail below, higher concentrations of di- and tri-esters may be tolerated in the raw material if the formulation initially includes free glycerin because of transesterification reactions.

Although in some situations it is desirable to avoid di- or tri-esters as a component of the starting materials, it is possible to use relatively pure tri-esters in the preparation of certain compositions described herein (for example, as a hydrophobic component) and have effective antimicrobial activity.

In certain embodiments, the most preferred antimicrobial lipid components include glycerol monolaurate, glycerol monocaprate, glycerol monocaprylate, propylene glycol monolaurate, propylene glycol monocaprate, propylene glycol monocaprylate, 2-ethylhexyl laurate, caprylyl lactate, capryl lactate, lauryl lactate, and combinations thereof.

To achieve rapid antimicrobial activity, formulations may incorporate one or more antimicrobial lipids in the composition approaching, or preferably exceeding, the solubility limit in the hydrophobic phase. While not intended to be bound by theory, it appears that antimicrobial lipids that preferably partition into the hydrophobic component are not readily available to kill microorganisms which are in or associated with an aqueous phase in or on the tissue. In most compositions, the antimicrobial lipid is preferably incorporated in at least 60%, preferably, at least 75%, more preferably, at least 100%, and most preferably, at least 120%, of the solubility limit of the hydrophobic component at 23° C. This in conveniently determined by making the formulation without the antimicrobial lipid, separating the phases (e.g., by centrifugation or other suitable separation technique) and determining the solubility limit by addition of progressively greater levels of the antimicrobial lipid until precipitation occurs. One skilled in the art will realize that creation of supersaturated solutions must be avoided for an accurate determination. In hydrophilic gels and creams the hydrophilic component is preferably selected to have an antimicrobial lipid solubility greater than that of water. In this manner, the vehicle component can promote the diffusion of the antimicrobial lipid on and into the tissue and any biofilm that may be present on the tissue.

Phenolic Antiseptics

The phenolic antiseptic component includes an effective amount of one or more antiseptics selected from the group consisting of diphenyl ethers, phenolics (including halogenated phenolics), bisphenolics, resorcinols, anilides, and compatible combinations thereof.

Phenolic antiseptics suitable for use in the antimicrobial compositions include, but are not limited to, diphenyl ethers, such as the polyhalogenated hydroxy diphenyl ethers, more specifically those containing multiple halogen substituents; phenolics including simple phenolics, such as phenol, cresol, o-phenylphenol, and halogenated phenolics, such as p-chlorometa-xylenol, dichlorometa-xylenol, o-benzyl p-chlorophenol and p-isoamylphenol; bisphenolics, such as 2,2'-methylene bis(3,4,6-trichlorophenol), 2,2'-methylene bis(4,6-dichlorophenol), 2,2'-methylene bis(4-chlorophenol), 2,2'-thio bis(4,6-dichlorophenol); resorcinols; and anilides, salicylanilide, monohalogenated salicylanilide, and polyhalogenated salicylanilide. The following classes are used in most embodiments:

1. Diphenyl ethers. Diphenyl ethers such as polyhalogenated hydroxyl diphenyl ethers, more specifically those containing multiple halogen substituents, such as triclosan (2',4,4'-trichloro-2-hydroxy-diphenyl ether or 3-chloro-2-(2,4 dichlorophenoxy)phenol), and the like. These compounds can be represented by the following chemical structure:

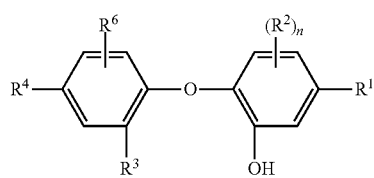

wherein $R^1$ and $R^3$ can be chlorine, bromine, or hydrogen, $R^2$ is chlorine or bromine; $R^4$ can be chlorine, bromine, an alkyl having 1 to 3 carbon atoms, $CH_3O—$, $CN—$, and $NH_2—$, $R^6$ can be hydrogen, chlorine, bromine, methyl, trichloromethyl, $CH_3O—$, $CN—$, and $NH_2—$; and n is 1 or 2.

2. Phenolics. Phenolics include phenol and derivatives thereof, including both simple phenolics, such as phenol, cresol, o-phenylphenol, and halogenated phenolics, such as p-chlorometa-xylenol, dichlorometa-xylenol, and p-isoarnylphenol. Other phenolics include mono- and poly-alkyl and aromatic halophenols (e.g., methyl-p-chlorophenol, n-butyl-p-chlorophenol, o-chlorophenol, o-benzyl-p-chlorophenol, o-phenylethyl-m-methyl-p-chlorophenol, 6-iso-propyl-2-ethyl-3-methyl-p-chlorophenol, methyl-p-bromophenol, tert-amyl-o-bromophenol, 3,4,5,6-terabromo-2-methylphenol. A preferred antiseptic of this class is p-chloro-m-xylenol (PCMX).

3. Resorcinols. Resorcinols include resorcinol and its derivatives. Examples of such compounds include methyl-resorcinol, ethyl-resorcinol, n-propyl-resorcinol, n-butyl-resorcinol, n-amyl-resorcinol, n-hexyl-resorcinol, 4-hexyl-resorcinol, n-heptyl-resorcinol, n-octyl-resorcinol, n-nonyl-resorcinol, phenyl-resorcinol, benzyl-resorcinol, phenylethyl-resorcinol, phenylpropyl-resorcinol, p-chlorobenzyl-resorcinol, 5-chloro-2,4-dihydroxydiphenyl methane, 4'-chloro-2,4-dihydroxydiphenyl methane, 5-bromo-2,4-dihydroxydiphenyl methane, 4'-bromo-2,4-dihydroxydiphenyl methane, and thymol enjenol.

4. Bisphenolics. Bisphenolics include 2,2'-methylene bis(4-chlorophenol), 2,2'-methylene bis(3,4,6-trichlorophenol), 2,2'-methylene bis(4-chloro-6-bromophenol), bis(2-hydroxy-3,5-dichlorophenyl) sulfide, and bis(2-hydroxy-5-chlorobenzyl) sulfide.

5. Anilides. Anilides include salicylanilides and carbanilides such as those discussed in *Disinfection, Sterilization, and Preservation*, $2^{nd}$ Ed. Edited by Seymour S. Block, Chapter 14, Lea & Febiger, Philadelphia, Pa., 1977; halogenated carbanilide compounds as described in U.S. Pat. No. 2,818,390, and halogenated salicylanilides including monohalogenated salicylanilide and polyhalogenated salicylanilide. Particularly preferred carbanilide compounds are 3,4,4'-trichloro-carbanilide (triclocarban); 3,4',5-tribromosalicylanilide; 4,4'-dichloro-3'-(trifluoromethyl) carbanilide. Other anilides may be useful including, but not limited to, salicylanilide, monohalogenated salicylanilide, and polyhalogenated salicylanilide such as those disclosed in U.S. Pat. Nos. 4,010,252 and 4,894,220.

These compounds may be relatively water insoluble and thus it is preferred to formulate these compounds in the presence of a hydrophobic component and/or an emulsifier/surfactant, in an emulsion (water-in-oil or oil-in-water), or in a hydrophilic vehicle. These compounds are typically added to the formulations in amounts of 0.5% by weight, and preferably 1% by weight. In most embodiments, the compounds are added in amounts of no greater than 20 wt-%, preferably no more than 12 wt-%, more preferably no more than 8 wt-%, and even more preferably no greater than 6 wt-%.

Cationic Antispetics

Cationic antiseptics suitable for use in the present invention include, for example: biguanides and bisbiguanides, such as chlorhexidine and its various salts, including but not limited to, the digluconate, diacetate, dimethosulfate, and dilactate salts, as well as combinations thereof; polymeric quaternary ammonium compounds, such as polyhexamethylenebiguanide; silver and various silver complexes; small molecule quaternary ammonium compounds, such as benzalkoium chloride and alkyl substituted derivatives, di-long chain alkyl (i.e., C8-C18) quaternary ammonium compounds, cetylpyridinium halides and their derivatives, benzethonium chloride and its alkyl substituted derivatives, octenidine, and compatible combinations thereof.

The compositions described herein include one or more antimicrobials (preferably, antiseptics) at a suitable level to produce the desired result. Such compositions preferably include a total amount of antimicrobial (preferably, antiseptic) of at least 0.2 percent by weight (wt-%), more preferably at least 0.25 wt-%, even more preferably at least 0.35 wt-%, even more preferably at least 0.5 wt-%, and even more preferably at least 1, at least 2, or even at least 3 wt-%, based on the total weight of the "ready to use" or "as used" composition. In a preferred embodiment, the antimicrobial(s) are present in a total amount of no greater than 40 wt-%, preferably no greater than 30 wt-%, more preferably no greater than 15 wt-%, even more preferably no greater than 10 wt-%, and even more preferably no greater than 6 wt-%, based on the "ready to use" or "as used" composition. Antimicrobials that are liquids at room temperature, however, may be used as the vehicle and thus present in amounts up to about 99%. For example, many of the antimicrobial lipids which are liquids are room temperature are non-irritating to skin and mucosal tissue and thus may be used as the vehicle. For example, the C8-C12 fatty acid esters of propylene glycol, 2-ethyl-hexyl glyceryl ether, C8-C12 branched and straight chain alkyl alcohol esters of lactic acid are all liquids that are potentially useful in high concentrations. Certain of the antimicrobial lipids that are solids at room temperature can also be used in higher concentrations if mixed with a component that prevents or minimizes crystallization. These "crystallization inhibitors" may include esters, ethers, and glycols that are liquid at room temperature. In other instances, the compositions may include higher concentrations of the antimicrobial agents if they are intended to be diluted prior to use.

The antimicrobials (preferably, antiseptics) of this invention may be used alone or in combination in order to effectively kill microorganisms on tissue. Certain combinations of antimicrobials (preferably, antiseptics) may be particularly useful while others may result in unstable formulations or inactivation of the antimicrobial activity. On the other hand, other antimicrobial combinations may produce an enhancement or synergistic effect.

Certain combinations of antimicrobials may be particularly useful while others may result in unstable formulations or inactivation of the antimicrobial activity. For example, C6 and higher fatty acids may enhance the activity of the fatty acid monoglycerides antiseptics described below.

Penetration Agent

A penetration agent may also be used to facilitate the diffusion of the composition in whole or in part but preferably at least the antimicrobial lipid, and preferably the enhancer, if present, and secondary active, if present, and surfactant, if present, are able to diffuse through the tympanic membrane into the middle and inner ear in order to kill or inactivate microorganisms and reduce inflammation of ear tissues. A penetration agent is a compound that enhances the antiseptic diffusion into the middle ear by increasing the permeability of the tympanic membrane and/or surrounding tissue to the antimicrobial component and pharmacologically active agent, if present, to increase the rate at which the drug diffuses through the tympanic membrane and enters the tissues and fluid within the middle ear. It should be noted that the middle ear is normally free of liquid but during otitis media the chamber can be come partially or entirely filled with fluid due in large part to an inflammatory response. Preferably the antimicrobial component is able to diffuse into this fluid and kill or inactivate the microorganisms. Furthermore, preferably the antimicrobial component and/or surfactant component are able to reduce the surface tension of the fluid in the middle ear to facilitate drainage. A penetration agent increases permeability by reversibly damaging or by altering the physiochemical nature of the TM to reduce its diffusional resistance. This process may be similar to that reported for skin. (Osborne D W, Henke J J, Pharmaceutical Technology, November 1997, pp 58-86).

Preferred penetration agents are non-toxic, non-irritating, non-sensitizing and non-comedogenic, readily emulsifiable in water, good solvents to solubilize the formulation components such as the antimicrobial lipid, enhancer, and surfactant components (if present), has a high positive spreading coefficient, is a good wetting agent for dry and wet tissue and is stable to hydrolysis within pH range of about 3-8. Preferred penetration agents are water insoluble. The penetration enhancing component may be used in concentrations of 0-99%. In some preferred embodiments the penetration agent is the vehicle. In other embodiments, the penetration agent is present in an amount of at least 2% by weight, more preferably 4% by weight, and most preferably 8% by weight. In other embodiments, the total concentration of the penetration enhancer combined with the antimicrobial lipid component is present in an amount of at least 2% by weight, more preferably 4% by weight, and most preferably 8% by weight.

Examples of penetration agents include without limitation: lower alcohols (C1-C4 alkyl alcohols), such as ethanol and isopropanol; polyols, such as polyethylene glycol, polypropylene glycol, polybutylene glycol as well as glycols formed from more than one alkyl epoxide including both block and random copolymers, limonene, terpenes, dioxolane; glycols, preferably having 2-6 hydroxyl groups, such as propylene glycol, dipropyelne glycol, butylene glycol, and glycerol; sulfoxides, such as dimethylsulfoxide (DMSO) and methyl dodecyl sulfoxide; amides such as dimethylformamide and dimethylacetamide; ketones; oleates, such as triolein and polyethylene glycol oleates such as PEG-5 oleate; various alkanoic acids, such as caprylic acid; lactam compounds, such as azone and N-methylpyrrolidone; long chain branched or straight chain saturated or unsaturated alcohols having 8-22 carbon atoms, such as oleyl alcohol, linoleyl alcohol, erucyl alcohol, octanol, dodecyl alcohol and polyethoxylated derivatives thereof typically having 2-40 moles of ethylene oxide units per mole of long chain alcohol; dialkylamino acetates, and admixtures thereof. The use of such penetration agents is disclosed, for example, in U.S. Pat. No. 6,093,417, hereby incorporated by reference. Preferred delivery enhancing components include lauryl alcohol, lauramide DEA, lauryl pyrrolidone-5-carboxylate; ascorbyl palmitate; glycerol; tetraglycol (.alpha.-[(tetrahydro-2-furanyl)methyl]-.omega.-hydroxy-poly(oxy-1,2-ethan ediyl)), lauryl glycol (i.e. 1,2-dodecanediol) and mixtures thereof. Particularly preferred penetration agents are alkyl esters, aralkyl esters and alkaryl esters such as short chain alkyl or aryl esters (C1-C6) of long chain straight or branched chain alkyl or alkenyl alcohols or acids (C8-C36) and their polyethoxylated derivatives (a particularly preferred subclass are benzoic acid esters of alkyl alcohols such as C12-C15 alkyl benzoate which is commercially available as FINSOLV TN, Finetex Inc., Elmwood Park, N.J.); short chain alkyl or aryl esters (C1-C6) of C4-C12 diacids or diols optionally substituted in available positions by —OH; alkyl or aryl C1-C9 esters of glycerol, pentaerythritol, ethylene glycol, propylene glycol, as well as polyethoxylated derivatives of these and polyethylene glycol; C12-C22 alkyl esters or ethers of polypropylene glycol; C12-C22 alkyl esters or ethers of polypropylene glycol/polyethylene glycol copolymer; and polyether polysiloxane copolymers.

It is noted that many of the surfactants disclosed herein may also significantly improve penetration of the antimicrobial composition or its components. For example, many sulfonated surfactants are well known to disrupt the stratum corneum and help enhance penetration of active ingredients into and through skin. For the purposes of this invention these components are still considered surfactants. Compositions comprising a surfactant may not require an additional penetration agent. Similarly some of the hydrophobic and/or hydrophilic components disclosed herein may also significantly improve penetration of the antimicrobial composition or its components.

It is also noted that many of the antimicrobial lipids are themselves amphipathic and may improve penetration through the TM. Therefore, compositions high in the antimicrobial lipid may not require an additional penetration agent.

Enhancer Component

Compositions described herein preferably include an enhancer (preferably a synergist) to enhance the antimicrobial activity especially against Gram negative bacteria, such as E. coli and Psuedomonas sp. The chosen enhancer preferably affects the cell envelope of the bacteria. While not bound by theory, it is presently believed that the enhancer functions by allowing the antimicrobial component to more easily enter the cell cytoplasm and/or by facilitating disruption of the cell envelope. The enhancer component may include an alpha-hydroxy acid, a beta-hydroxy acid, other carboxylic acids, a phenolic compound (such as certain antioxidants but other than parabens), a monohydroxy alcohol, a chelating agent (other than EDTA), a glycol ether (i.e., ether glycol), or a sugar and/or sugar alcohol. Various combinations of enhancers can be used if desired.

The alpha-hydroxy acid, beta-hydroxy acid, and other carboxylic acid enhancers are preferably present in their protonated, free acid form. It is not necessary for all of the acidic enhancers to be present in the free acid form; however, the preferred concentrations listed below refer to the amount present in the free acid form. Additional, non-alpha hydroxy acid, betahydroxy acid or other carboxylic acid enhancers, may be added in order to acidify the formulation or buffer it at a pH to maintain antimicrobial activity. Furthermore, the chelator enhancers that include carboxylic acid groups are preferably present with at least one, and more preferably at least two, carboxylic acid groups in their free acid form. The concentrations given below assume this to be the case.

One or more enhancers may be used in the compositions described herein at a suitable level to produce the desired result. In a preferred embodiment, they are present in a total amount greater than 0.01 wt-%, more preferably in an amount greater than 0.1 wt-%, even more preferably in an amount greater than 0.2 wt-%, even more preferably in an amount greater than 0.25 wt-%, and most preferably in an amount greater than 0.4 wt-% based on the total weight of the ready to use composition. In a preferred embodiment, they are present in a total amount of no greater than 20 wt-%, based on the total weight of the ready to use composition. Such concentrations typically apply to alpha-hydroxy acids, beta-hydroxy acids, other carboxylic acids, chelating agents, phenolics, ether glycols, and (C5-C10)monohydroxy alcohols. Generally, higher concentrations are needed for (C1-C4)monohydroxy alcohols, as described in greater detail below.

The alpha-hydroxy acid, beta-hydroxy acid, and other carboxylic acid enhancers, as well as chelators that include carboxylic acid groups, are preferably present in a concentration of no greater than 100 milliMoles per 100 grams of formulated composition. In most embodiments, alpha-hydroxy acid, beta-hydroxy acid, and other carboxylic acid enhancers, as well as chelators that include carboxylic acid groups, are preferably present in a concentration of no greater than 75 milliMoles per 100 grams, more preferably no greater than 50 milliMoles per 100 grams, and most preferably no greater than 25 milliMoles per 100 grams of formulated composition.

The total concentration of the enhancer component relative to the total concentration of the antimicrobial lipid component is preferably within a range of 10:1 to 1:300, and more preferably 5:1 to 1:10, on a weight basis.

An additional consideration when using an enhancer is the solubility and physical stability in the compositions. Many of the enhancers discussed herein are insoluble in preferred hydrophobic components such as petrolatum. It has been found that the addition of a minor amount (typically less than 30 wt-%, preferably less than 20 wt-%, and more preferably less than 12 wt-%) of a hydrophilic component not only helps dissolve and physically stabilize the composition but improves the antimicrobial activity as well. These hydrophilic components are described below.

Alternatively, the enhancer component may be present in excess of the solubility limit provided that the composition is physically stable. This may be achieved by utilizing a sufficiently viscous composition that stratification (e.g., settling or creaming) of the antimicrobial lipid does not appreciably occur.

Alpha-Hydroxy Acids

An alpha-hydroxy acid is typically a compound represented by the formula:

$$R^5(CR^6OH)_n COOH$$

wherein: $R^5$ and $R^6$ are each independently H, a (C1-C8)alkyl group (straight, branched, or cyclic group), a (C6-C12)aryl group, a (C6-C12)aralkyl group, or a (C6-C12)alkaryl group (wherein the alkyl group of the aralkyl or alkaryl is straight, branched, or cyclic), wherein $R^5$ and $R^6$ may be optionally substituted with one or more carboxylic acid groups; and n=1-3, preferably, n=1-2.

Exemplary alpha-hydroxy acids include, but are not limited to, lactic acid, malic acid, citric acid, 2-hydroxybutanoic acid, mandelic acid, gluconic acid, glycolic acid (i.e., alpha-hydroxyethanoic acid), tartaric acid, ascorbic acid, alpha-hydroxyoctanoic acid, alpha-hydroxycaprylic acid, and salicylic acid, as well as derivatives thereof (e.g., compounds substituted with hydroxyls, phenyl groups, hydroxyphenyl groups, alkyl groups, halogens, as well as combinations thereof). Preferred alpha-hydroxy acids include lactic acid, malic acid, and mandelic acid. These acids may be in D, L, or DL form and may be present as free acid, lactone, or partial salts thereof. All such forms are encompassed by the term "acid." Preferably, the acids are present in the free acid form. In certain preferred embodiments, the alpha-hydroxy acids useful in the compositions described herein are selected from the group consisting of lactic acid, mandelic acid, and malic acid, and mixtures thereof. Other suitable alpha-hydroxy acids are described in U.S. Pat. No. 5,665,776 (Yu).

One or more alpha-hydroxy acids may be used in the compositions described herein at a suitable level to produce the desired result. In a preferred embodiment, they are present in a total amount of at least 0.25 wt-%, more preferably, at least 0.5 wt-%, and even more preferably, at least 1 wt-%, based on the total weight of the ready to use composition. In a preferred embodiment, they are present in a total amount of no greater than 10 wt-%, more preferably, no greater than 5 wt-%, and even more preferably, no greater than 3 wt-%, based on the total weight of the ready to use composition. Higher concentrations may become irritating.

The ratio of alpha-hydroxy acid enhancer to total antimicrobial component is preferably at most 10:1, more preferably at most 5:1, and even more preferably at most 1:1. The ratio of alpha-hydroxy acid enhancer to total antimicrobial component is preferably at least 1:20, more preferably at least 1:12, and even more preferably at least 1:5. Preferably the ratio of alpha-hydroxy acid enhancer to total antimicrobial component is within a range of 1:12 to 1:1.

Beta-Hydroxy Acids

A beta-hydroxy acid is typically a compound represented by the formula:

or

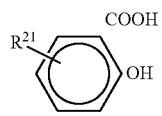

wherein: $R^7$, $R^8$, and $R^9$ are each independently H, a (C1-C8) alkyl group (saturated straight, branched, or cyclic group), a (C6-C12)aryl group, a (C6-C12)aralkyl group, or a (C6-C12) alkaryl group (wherein the alkyl group of the alkaryl or aralkyl is straight, branched, or cyclic), wherein $R^7$ and $R^8$ may be optionally substituted with one or more carboxylic acid groups; m=0 or 1; n=1-3 (preferably, n=1-2); and $R^{21}$ is H, (C1-C4)alkyl or a halogen.

Exemplary beta-hydroxy acids include, but are not limited to, salicylic acid, beta-hydroxybutanoic acid, tropic acid, 4-aminosalyclic acid, and trethocanic acid. In certain preferred embodiments, the beta-hydroxy acids useful in the compositions described herein are selected from the group consisting of salicylic acid, beta-hydroxybutanoic acid, and mixtures thereof. Other suitable beta-hydroxy acids are described in U.S. Pat. No. 5,665,776 (Yu).

One or more beta-hydroxy acids may be used in the compositions described herein at a suitable level to produce the desired result. In a preferred embodiment, they are present in a total amount of at least 0.1 wt-%, more preferably at least 0.25 wt-%, and even more preferably at least 0.5 wt-%, based on the total weight of the ready to use composition. In a preferred embodiment, they are present in a total amount of no greater than 10 wt-%, more preferably no greater than 5 wt-%, and even more preferably no greater than 3 wt-%, based on the total weight of the ready to use composition. Higher concentrations may become irritating.

The ratio of beta-hydroxy acid enhancer to total antimicrobial component is preferably at most 10:1, more preferably at most 5:1, and even more preferably at most 1:1. The ratio of beta-hydroxy acid enhancer to total antimicrobial component is preferably at least 1:20, more preferably at least 1:15, and even more preferably at least 1:10. Preferably the ratio of beta-hydroxy acid enhancer to total antimicrobial component is within a range of 1:15 to 1:1.

In systems with low concentrations of water, or that are essentially free of water, transesterification or esterification may be the principle route of loss of carboxylic acid containing enhancers. Thus, certain alpha-hydroxy acids (AHA) and beta-hydroxy acids (BHA) are particularly preferred since these are believed to be less likely to transesterify or esterify with other components in the composition such as, for example, an ester antimicrobial lipid or other ester, by reaction of the hydroxyl group of the AHA or BHA. For example, salicylic acid may be particularly preferred in certain formulations since the phenolic hydroxyl group is a much more acidic alcohol and thus much less likely to react than an aliphatic hydroxyl group. Other particularly preferred compounds in anhydrous or low-water content formulations include lactic, mandelic, malic, citric, tartaric, and glycolic acid. Benzoic acid and substituted benzoic acids that do not include a hydroxyl group, while not hydroxyl acids, are also preferred due to a reduced tendency to form ester groups.

Other Carboxylic Acids

Carboxylic acids other than alpha- and beta-carboxylic acids are suitable for use in the enhancer component. These include alkyl, aryl, aralkyl, or alkaryl carboxylic acids typically having equal to or less than 16, and often equal to or less than 12, carbon atoms. A preferred class of these can be represented by the following formula:

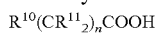

wherein: $R^{10}$ and $R^{11}$ are each independently H or a (C1-C4) alkyl group (which can be a straight, branched, or cyclic group), a (C6-C12)aryl group, a (C6-C16) group containing both aryl groups and alkyl groups (which can be a straight, branched, or cyclic group), wherein $R^{10}$ and $R^{11}$ may be optionally substituted with one or more carboxylic acid groups; and n=0-3, preferably, n=0-2. Preferably, the carboxylic acid is a (C1-C4)alkyl carboxylic acid, a (C6-C16) aralkyl carboxylic acid, or a (C6-C16)alkaryl carboxylic acid. Exemplary acids include, but are not limited to, acetic acid, propionic acid, benzoic acid, benzylic acid, nonylbenzoic acid, p-hydroxybenzoic acid, retinoic acid, and the like. Particularly preferred is benzoic acid.

One or more carboxylic acids (other than alpha- or beta-hydroxy acids) may be used in the compositions described herein at a suitable level to produce the desired result. In a preferred embodiment, they are present in a total amount of at least 0.1 wt-%, more preferably at least 0.25 wt-%, even more preferably at least 0.5 wt-%, and most preferably at least 1 wt-%, based on the ready to use concentration composition. In a preferred embodiment, they are present in a total amount of no greater than 10 wt-%, more preferably no greater than 5 wt-%, and even more preferably no greater than 3 wt-%, based on the ready to use composition.

The ratio of the total concentration of carboxylic acids (other than alpha- or beta-hydroxy acids) to the total concentration of the antimicrobial component is preferably within a range of 10:1 to 1:100, and more preferably 2:1 to 1:10, on a weight basis.

Chelators

A chelating agent (i.e., chelator) is typically an organic compound capable of multiple coordination sites with a metal ion in solution. Typically these chelating agents are polyanionic compounds and coordinate best with polyvalent metal ions. Exemplary chelating agents include, but are not limited to, ethylene diamine tetraacetic acid (EDTA), free of antibiotics and salts thereof (e.g., EDTA(Na)$_2$, EDTA(Na)$_4$, EDTA (Ca), EDTA(K)$_2$), sodium acid pyrophosphate, acidic sodium hexametaphosphate, adipic acid, succinic acid, polyphosphoric acid, sodium acid pyrophosphate, sodium hexametaphosphate, acidified sodium hexametaphosphate, nitrilotris(methylenephosphonic acid), diethylenetriaminepentaacetic acid, ethylenebis(oxyethylenenitrilo)tetraacetic acid, glycolether diaminetetraacetic acid, ethyleneglycol-O,O'bis(2-aminoethyl)-N,N,N',N'-tetraacetic acid (EGTA), N-(2-hydroxyethyl) ethylenediamine-N,N',N'-triacetic acid trisodium salt (HETA), polyethylene glycol diaminetetraacetic acid, 1-hydroxyethylene, 1,1-diphosphonic acid (HEDP), and diethylenetriaminepenta-(methylenephosphonic acid). Any of these chelating agents may also be used in their partial or complete salt form. Certain carboxylic acids, particularly the alpha-hydroxy acids and beta-hydroxy acids, can also function as chelators, e.g., malic acid, citric, and tartaric acid.

Also included as chelators are compounds highly specific for binding ferrous and/or ferric ion such as siderophores, and iron binding proteins. Iron binding proteins include, for example, lactoferrin, and transferrin. Siderophores include, for example, enterochlin, enterobactin, vibriobactin, anguibactin, pyochelin, pyoverdin, and aerobactin.

In certain preferred embodiments, the chelating agents useful in the compositions described herein include those selected from the group consisting of ethylenediaminetetraacetic acid, and salts thereof, succinic acid, tartaric acid and mixtures thereof.

One or more chelating agents may be used in the compositions described herein at a suitable level to produce the desired result. In a preferred embodiment, they are present in a total amount of at least 0.01 wt-%, more preferably at least 0.05 wt-%, even more preferably at least 0.1 wt-%, and even more preferably at least 1 wt-%, based on the weight of the ready to use composition. In a preferred embodiment, they are present in a total amount of no greater than 10 wt-%, more preferably no greater than 5 wt-%, and even more preferably no greater than 1 wt-%, based on the weight of the ready to use composition.

The ratio of the total concentration of chelating agents (other than alpha- or beta-hydroxy acids) to the total concentration of the antimicrobial component is preferably within a range of 10:1 to 1:100, and more preferably 1:1 to 1:10, on a weight basis.

Phenolic Enhancer Compounds

A phenolic compound (i.e. a phenol or phenol derivative) enhancer is typically a compound having the following general structure:

wherein: m is 0 to 3 (especially 1 to 3), n is 1 to 3 (especially 1 to 2), each $R^{12}$ independently is alkyl or alkenyl of up to 12 carbon atoms (especially up to 8 carbon atoms) optionally substituted with 0 in or on the chain (e.g., as a carbonyl group) or OH on the chain, and each $R^{13}$ independently is H or alkyl or alkenyl of up to 8 carbon atoms (especially up to 6 carbon atoms) optionally substituted with 0 in or on the chain (e.g., as a carbonyl group) or OH on the chain, but where $R^{13}$ is H, n preferably is 1 or 2.

Examples of phenolic enhancers include, but are not limited to, butylated hydroxy anisole, e.g., 3(2)-tert-butyl-4-methoxyphenol (BHA), 2,6-di-tert-butyl-4-methylphenol (BHT), 3,5-di-tert-butyl-4-hydroxybenzylphenol, 2,6-di-tert-4-hexylphenol, 2,6-di-tert-4-octylphenol, 2,6-di-tert-4-decylphenol, 2,6-di-tert-butyl-4-ethylphenol, 2,6-di-tert-4-butylphenol, 2,5-di-tert-butylphenol, 3,5-di-tert-butylphenol, 4,6-di-tert-butyl-resorcinol, methyl paraben (4-hydroxybenzoic acid methyl ester), ethyl paraben, propyl paraben, butyl paraben, as well as combinations thereof. A preferred group of the phenolic compounds is the phenol species having the general structure shown above where $R^{13}$=H and where $R^{12}$ is alkyl or alkenyl of up to 8 carbon atoms, and n is 1, 2, or 3, especially where at least one $R^{12}$ is butyl and particularly tert-butyl, and especially the non-toxic members thereof. Some of the preferred phenolic enhancers are BHA, are BHT.

One or more phenolic compounds may be used in the compositions described herein at a suitable level to produce the desired result. The concentrations of the phenolic compounds in medical-grade compositions may vary widely, but as little as 0.001 wt-%, based on the total weight of the composition, can be effective when the above-described esters are present within the above-noted ranges. In a preferred embodiment, they are present in a total amount of at least 0.01 wt-%, more preferably at least 0.10 wt-%, and even more preferably at least 0.25 wt-%, based on the ready to use composition. In a preferred embodiment, they are present in a total amount of no greater than 8 wt-%, more preferably no greater than 4 wt-%, and even more preferably no greater than 2 wt-%, based on the ready to use composition.

It is preferred that the ratio of the total phenolic concentration to the total concentration of the antimicrobial component be within a range of 10:1 to 1:300, and more preferably within a range of 1:1 to 1:10, on a weight basis.

The above-noted concentrations of the phenolics are normally observed unless concentrated formulations for subsequent dilution are intended. On the other hand, the minimum concentration of the phenolics and the antimicrobial components to provide an antimicrobial effect will vary with the particular application.

Monohydroxy Alcohols

An additional enhancer class includes monohydroxy alcohols having 1-10 carbon atoms. This includes the lower (i.e., C1-C4) monohydroxy alcohols (e.g., methanol, ethanol, isopropanol, and butanol) as well as longer chain (i.e., C5-C10) monohydroxy alcohols (e.g., isobutanol, t-butanol, octanol, and decanol). Other useful alcohols include benzyl alcohol, and menthol. In certain preferred embodiments, the alcohols useful in the compositions described herein are selected from the group consisting of methanol, ethanol, isopropyl alcohol, and mixtures thereof.

One or more alcohols may be used in the compositions described herein at a suitable level to produce the desired result. In a preferred embodiment, the short chain (i.e., C1-C4) alcohols are present in a total amount of at least 10 wt-%, even more preferably at least 15 wt-%, even more preferably at least 20 wt-%, and even more preferably at least 25 wt-%, based on the total weight of the ready to use composition.

In a preferred embodiment, the (C1-C4)alcohols are present in a total amount of no greater than 90 wt-%, more preferably no greater than 70 wt-%, even more preferably no greater than 60 wt-%, and even more preferably no greater than 50 wt-%, based on the total weight of the ready to use composition.

For certain applications, lower alcohols may not be preferred due to the strong odor and potential for stinging and irritation. This can occur especially at higher levels. In applications where stinging or burning is a concern, the concentration of (C1-C4)alcohols is preferably less than 20 wt-%, more preferably less than 15 wt-%.

In another preferred embodiment, longer chain (i.e., C5-C10)alcohols are present in a total amount of at least 0.1 wt-%, more preferably at least 0.25 wt-%, and even more preferably at least 0.5 wt-%, and most preferably at least 1.0%, based on the ready to use composition. In a preferred embodiment, the (C5-C10)alcohols are present in a total amount of no greater than 10 wt-%, more preferably no greater than 5 wt-%, and even more preferably no greater than 2 wt-%, based on the total weight of the ready to use composition.

Ether Glycols

An additional enhancer class includes ether glycols (also referred to as glycol ethers). Exemplary ether glycols include those of the formula:

wherein R'=H, a (C1-C8)alkyl, a (C6-C12)aryl group, a (C6-C12)aralkyl group, or a (C6-C12)alkaryl group; and each R" is independently =H, methyl, or ethyl; and n=0-5, preferably 1-3. Examples include 2-phenoxyethanol, dipropylene glycol, triethylene glycol, the line of products available under the trade designation DOWANOL DB (di(ethylene glycol) butyl ether), DOWANOL DPM (di(propylene glycol) monomethyl ether), and DOWANOL TPNB (tri(propylene glycol) monobutyl ether), as well as many others available from Dow Chemical, Midland, Mich.

One or more ether glycols may be used in the compositions described herein at a suitable level to produce the desired result. In a preferred embodiment, they are present in a total amount of at least 0.01 wt-%, based on the total weight of the ready to use composition. In a preferred embodiment, they are present in a total amount of no greater than 20 wt-%, based on the total weight of the ready to use composition.

Sugars and Sugar Alcohols

Suitable sugars can include both monosaccharides and disaccharides. Suitable monosaccharides include, but are not limited to, mannose, xylose, maltose, sorbose, and their corresponding sugar alcohols mannitol, xylitol, maltitol, and sorbitol. In certain preferred embodiments, the sugar is selected from the group consisting of mannose, xylose, mannitol, xylitol, and combinations thereof. In certain embodiments, the sugar is a disaccharide of xylitol and glucose. For disaccharides, at least one of the sugars is preferably one of the suitable monosaccharides listed herein. The second sugar unit may be selected from any suitable sugar commonly used in food products, such as but not limited to, glucose, fructose, mannose, xylose, galacose, sorbose, and sorbitol.

One or more sugars or sugar alcohols may be used in the compositions described herein at a suitable level to produce the desired result. In a preferred embodiment, they are present in a total amount of at least 0.5 wt-% and preferably at least 1.0% based on the total weight of the ready to use composition. In a preferred embodiment, they are present in a total amount of no greater than 20 wt-%, based on the total weight of the ready to use composition.

Surfactant Component

Compositions described herein can optionally include at least one surfactant (i.e., a surfactant component) to emulsify the composition and to help wet the surface and/or to aid in contacting the microorganisms. The surface to be wetting may be the tissue and/or an instrument to be inserted into the body. As used herein the term "surfactant" means an amphiphile (a molecule possessing both polar and nonpolar regions which are covalently bound) capable of reducing the surface tension of water and/or the interfacial tension between water and an immiscible liquid. The term is meant to include soaps, detergents, emulsifiers, surface active agents, and the like. The surfactant can be cationic, anionic, nonionic, or amphoteric. This includes a wide variety of conventional surfactants. Combinations of various surfactants can be used if desired.

Certain ethoxylated surfactants can reduce or eliminate the antimicrobial efficacy of at least some antimicrobial lipid components. For example, some antimicrobial lipid components may be inactivated by certain polyethoxylated surfactants. The exact mechanism of this is not known and not all ethoxylated surfactants display this negative effect. For example, poloxamer (polyethylene oxide/polypropylene oxide) surfactants have been shown to be compatible with the antimicrobial lipid component, but ethoxylated sorbitan fatty acid esters such as those sold under the trade name TWEEN by ICI have not been compatible. It should be noted that these are broad generalizations and the activity could be formulation dependent. One skilled in the art can easily determine compatibility of a surfactant by making the formulation and testing for antimicrobial activity as described in the Examples Section.

It should be noted that certain antimicrobials are amphiphiles and may be surface active. For example, certain antimicrobial alkyl monoglycerides described herein are surface active. For certain embodiments of the invention, the antimicrobial component is considered distinct from a "surfactant" component. Furthermore, certain iodophors may be produced by complexing iodine with a surfactant such as a polyethoxylated surfactant, e.g., polyethoxylated nonylphenol. For the purposes of this invention, the surfactant incorporated into the iodophor is not considered a surfactant but is part of the antimicrobial component.

Preferred non-ionic polyethoxylated surfactants having an alkyl, aralkyl or alarly group are those that have an HLB (i.e., hydrophile to lipophile balance) of at least 4 and more preferably at least 8. Even more preferred surfactants have an HLB of at least 12. Most preferred polyethoxylated surfactants have an HLB of at least 15; however, lower and higher HLB surfactants are still useful in compositions described herein.

Preferred surfactants also have a critical micelle concentration great than $0.5 \times 10^{-3}$ moles/liter, preferably greater than $1 \times 10^{-3}$ moles/liter and most preferably greater than $2 \times 10^{-3}$ moles/liter. Other preferred surfactants do not form micelles such as the POLOXAMER surfactants.

Examples of the various classes of surfactants are described below. In certain preferred embodiments, the surfactants useful in the compositions described herein are selected from the group consisting of sulfonate surfactants, sulfate surfactants, phosphonate surfactants, phosphate surfactants, poloxamer (polyethylene oxide/polypropylene oxide block copolymers) surfactants, cationic surfactants, and mixtures thereof. In certain more preferred embodiments, the surfactants useful in the compositions described herein are selected from the group consisting of sulfonates, sulfates, phosphates, and mixtures thereof.

One or more surfactants may be used in the compositions described herein at a suitable level to produce the desired result. In a preferred embodiment, they are present in a total amount of at least 0.1 wt-%, more preferably at least 0.5 wt-%, and even more preferably at least 1.0 wt-%, based on the total weight of the ready to use composition. Many of the compositions described herein are intended to be left on tissue for the desired indication, e.g., decolonizing urethral tissue. Therefore, in order to avoid irritation in a preferred embodiment, they are present in a total amount of no greater than 10 wt-%, more preferably no greater than 5 wt-%, even more preferably no greater than 3 wt-%, and even more preferably no greater than 2 wt-%, based on the total weight of the ready to use composition. The ratio of the total concentration of surfactant to the total concentration of the antimicrobial component is preferably within a range of 5:1 to 1:100, more preferably 3:1 to 1:10, and most preferably 2:1 to 1:3, on a weight basis.

Cationic Surfactants

Exemplary cationic surfactants include, but are not limited to, salts of optionally polyoxyalkylenated primary, secondary, or tertiary fatty amines; quaternary ammonium salts such as tetraalkylammonium, alkylamidoalkyltrialkylammonium, trialkylbenzylammonium, trialkylhydroxyalkylammonium, or alkylpyridinium halides (preferably chlorides or bromides) as well as other anionic counterions, such as but not limited to, alkyl sulfates, such as but not limited to, methosulfate and ethosulfate; imidazoline derivatives; amine oxides of a cationic nature (e.g., at an acidic pH).

In certain preferred embodiments, the cationic surfactants useful in the compositions described herein are selected from the group consisting of tetralkyl ammonium, trialkylbenzylammonium, and alkylpyridinium halides as well as other anionic counterions, such as but not limited to, C1-C4 alkyl sulfates, such as but not limited to, methosulfate and ethosulfate, and mixtures thereof.

Amine Oxide Surfactants

Also particularly preferred are amine oxide surfactants, which can be cationic at lower pH or nonionic at higher pH, including alkyl and alkylamidoalkyldialkylamine oxides of the following formula:

$$(R^{14})_3—N{\rightarrow}O$$

wherein $R^{14}$ is a (C1-C30)alkyl group (preferably a (C1-C14) alkyl group) or a (C6-C18)aralklyl or alkaryl group, wherein any of these groups can be optionally substituted in or on the chain by N—, O—, or S-containing groups such as amide, ester, hydroxyl, and the like. Each $R^{14}$ may be the same or different provided at least one $R^{14}$ group includes at least eight carbons. Optionally, the $R^{14}$ groups can be joined to form a heterocyclic ring with the nitrogen to form surfactants such as amine oxides of alkyl morpholine, alkyl piperazine, and the like. Preferably two $R^{14}$ groups are methyl and one $R^{14}$ group is a (C12-C16)alkyl or alkylamidopropyl group. Examples of amine oxide surfactants include those commercially available under the trade designations AMMONYX LO, LMDO, and CO, which are lauryldimethylamine oxide, laurylamidopropyldimethylamine oxide, and cetyl amine oxide, all from Stepan Company. Note that the amine oxide surfactants behave as cationic surfactants at lower pH values where they become protonated. The amine oxide surfactants may be used in their protonated or unprotonated form.

Anionic Surfactants

Exemplary anionic surfactants include, but are not limited to, sarcosinates, glutamates, alkyl sulfates, sodium or potassium alkyleth sulfates, ammonium alkyleth sulfates, ammonium laureth-n-sulfates, laureth-n-sulfates, isethionates, glycerylether sulfonates, sulfosuccinates, alkylglyceryl ether sulfonates, alkyl phosphates, aralkyl phosphates, alkylphosphonates, and aralkylphosphonates. These anionic surfactants may have a metal or organic ammonium counterion. In certain preferred embodiments, the anionic surfactants useful in the compositions described herein are selected from the group consisting of:

I. Sulfonates and Sulfates. Suitable anionic surfactants include sulfonates and sulfates such as alkyl sulfates, alkylether sulfates, alkyl sulfonates, alkylether sulfonates, alkylbenzene sulfonates, alkylbenzene ether sulfates, alkylsulfoacetates, secondary alkane sulfonates, secondary alkylsulfates, and the like. Many of these can be represented by the formulas:

$$R^{14}—(OCH_2CH_2)_n(OCH(CH_3)CH_2)_p—(Ph)_a-(OCH_2CH_2)_m—(O)_b—SO_3^-M^+$$

and $$R^{14}—CH[SO_3\text{-}M^+]\text{-}R^{15}$$

wherein: a and b=0 or 1; n, p, and m=0-100 (preferably 0-20, and more preferably 0-10); $R^{14}$ is defined as above provided at least one $R^{14}$ or $R^{15}$ is at least C8; $R^{15}$ is a (C1-C12)alkyl group (saturated straight, branched, or cyclic group) that may be optionally substituted by N, O, or S atoms or hydroxyl, carboxyl, amide, or amine groups; Ph=phenyl; and M is a cationic counterion such as H, Na, K, Li, ammonium, or a protonated tertiary amine such as triethanolamine or a quaternary ammonium group.

In the formula above, the ethylene oxide groups (i.e., the "n" and "m" groups) and propylene oxide groups (i.e., the "p" groups) can occur in reverse order as well as in a random, sequential, or block arrangement. Preferably for this class, $R^{14}$ includes an alkylamide group such as $R^{16}—C(O)N(CH_3)CH_2CH_2—$ as well as ester groups such as $—OC(O)—CH_2—$ wherein $R^{16}$ is a (C8-C22)alkyl group (branched, straight, or cyclic group). Examples include, but are not limited to: alkyl ether sulfonates such as lauryl ether sulfates such as POLYSTEP B12 (n=3-4, M=sodium) and B22 (n=12, M=ammonium) available from Stepan Company, Northfield, Ill. and sodium methyl taurate (available under the trade designation NIKKOL CMT30 from Nikko Chemicals Co., Tokyo, Japan); secondary alkane sulfonates such as Hostapur SAS which is a Sodium (C14-C17)secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo (C12-C16)fatty acid available from Stepan Company under the trade designation ALPHASTEP PC-48; alkylsulfoacetates and alkylsulfosuccinates available as sodium laurylsulfoacetate (under the trade designation LANTHANOL LAL) and disodiumlaurethsulfosuccinate (STEPANMILD SL3), both from Stepan Company; alkylsulfates such as ammoniumlauryl sulfate commercially available under the trade designation STEPANOL AM from Stepan Company; dialkylsulfosuccinates such as dioctylsodiumsulfosuccinate available as Aerosol OT from Cytec Industries. Hydrotropes such as DOWFAX hydrotrope from Dow chemical or other diphenyl oxide surfactants may also be used.

2. Phosphates and Phosphonates. Suitable anionic surfactants also include phosphates such as alkyl phosphates, alkylether phosphates, aralkylphosphates, and aralkylether phosphates. Many may be represented by the formula:

$$[R^{14}—(Ph)_a\text{-}O(CH_2CH_2O)_n(CH_2CH(CH_3)O)_p]_q—P(O)[O^-M^+]_r$$

wherein: Ph, $R^{14}$, a, n, p, and M are defined above; r is 0-2; and q=1-3; with the proviso that when q=1, r=2, and when q=2, r=1, and when q=3, r=0. As above, the ethylene oxide groups (i.e., the "n" groups) and propylene oxide groups (i.e., the "p" groups) can occur in reverse order as well as in a random, sequential, or block arrangement. Examples include a mixture of mono-, di- and tri-(alkyltetraglycolether)-o-phosphoric acid esters generally referred to as trilaureth-4-phosphate commercially available under the trade designation HOSTAPHAT 340KL from Clariant Corp., as well as PPG-5 ceteth 10 phosphate available under the trade designation CRODAPHOS SG from Croda Inc., Parsipanny, N.J., and mixtures thereof.

Amphoteric Surfactants

Surfactants of the amphoteric type include surfactants having tertiary amine groups, which may be protonated, as well as quaternary amine containing zwitterionic surfactants. Those that have been particularly useful include:

1. Ammonium Carboxylate Amphoterics. This class of surfactants can be represented by the following formula:

$$R^{17}—(C(O)—NH)_a—R^{18}—N^+(R^{19})_2—R^{20}—COO^-$$

wherein: a=0 or 1; $R^{17}$ is a (C7-C21)alkyl group (saturated straight, branched, or cyclic group), a (C6-C22)aryl group, or a (C6-C22)aralkyl or alkaryl group (saturated straight, branched, or cyclic alkyl group), wherein $R^{17}$ may be optionally substituted with one or more N, O, or S atoms, or one or more hydroxyl, carboxyl, amide, or amine groups; $R^{19}$ is H or a (C1-C8)alkyl group (saturated straight, branched, or cyclic group), wherein $R^{19}$ may be optionally substituted with one or more N, O, or S atoms, or one or more hydroxyl, carboxyl, amine groups, a (C6-C9)aryl group, or a (C6-C9)aralkyl or alkaryl group; and $R^{18}$ and $R^{20}$ are each independently a (C1-C10)alkylene group that may be the same or different and may be optionally substituted with one or more N, O, or S atoms, or one or more hydroxyl or amine groups.

More preferably, in the formula above, $R^{17}$ is a (C1-C18) alkyl group, $R^{19}$ is a (C1-C2)alkyl group preferably substituted with a methyl or benzyl group and most preferably with a methyl group. When $R^{19}$ is H it is understood that the surfactant at higher pH values could exist as a tertiary amine with a cationic counterion such as Na, K, Li, or a quaternary amine group.

Examples of such amphoteric surfactants include, but are not limited to: certain betaines such as cocobetaine and cocamidopropyl betaine (commercially available under the trade designations MACKAM CB-35 and MACKAM L from McIntyre Group Ltd., University Park, Ill.); monoacetates such as sodium lauroamphoacetate; diacetates such as disodium lauroamphoacetate; amino- and alkylamino-propionates such as lauraminopropionic acid (commercially available under the trade designations MACKAM 1L, MACKAM 2L, and MACKAM 151L, respectively, from McIntyre Group Ltd.).

2. Ammonium Sulfonate Amphoterics. This class of amphoteric surfactants are often referred to as "sultaines" or "sulfobetaines" and can be represented by the following formula

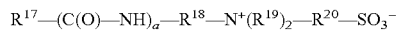

$$R^{17}-(C(O)-NH)_a-R^{18}-N^+(R^{19})_2-R^{20}-SO_3^-$$

wherein $R^{17}$-$R^{20}$ and "a" are defined above. Examples include cocamidopropylhydroxysultaine (commercially available as MACKAM 50-SB from McIntyre Group Ltd.). The sulfoamphoterics may be preferred over the carboxylate amphoterics since the sulfonate group will remain ionized at much lower pH values.

Nonionic Surfactants

Exemplary nonionic surfactants include, but are not limited to, alkyl glucosides, alkyl polyglucosides, polyhydroxy fatty acid amides, sucrose esters, esters of fatty acids and polyhydric alcohols, fatty acid alkanolamides, ethoxylated fatty acids, ethoxylated aliphatic acids, ethoxylated fatty alcohols (e.g., octyl phenoxy polyethoxyethanol available under the trade name TRITON X-100 and nonyl phenoxy poly(ethyleneoxy)ethanol available under the trade name NONIDET P-40, both from Sigma, St. Louis, Mo.), ethoxylated and/or propoxylated aliphatic alcohols (e.g., that available under the trade name BRIJ from ICI, Wilmington, Del.), ethoxylated glycerides, ethoxylated/propoxylated block copolymers such as PLURONIC and TETRONIC surfactants available from BASF, ethoxylated cyclic ether adducts, ethoxylated amide and imidazoline adducts, ethoxylated amine adducts, ethoxylated mercaptan adducts, ethoxylated condensates with alkyl phenols, ethoxylated nitrogen-based hydrophobes, ethoxylated polyoxypropylenes, polymeric silicones, fluorinated surfactants (e.g., those available under the trade names FLUORAD-FS 300 from 3M Company, St. Paul, Minn., and ZONYL from Dupont de Nemours Co., Wilmington, Del.), and polymerizable (reactive) surfactants (e.g., SAM 211 (alkylene polyalkoxy sulfate) surfactant available under the trade name MAZON from PPG Industries, Inc., Pittsburgh, Pa.). In certain preferred embodiments, the nonionic surfactants useful in the compositions described herein are selected from the group consisting of Poloxamers such as PLURONIC from BASF, sorbitan fatty acid esters, and mixtures thereof.

Hydrophilic Component

Compositions described herein can include a hydrophilic or water-soluble component to help solubilize and/or physically stabilize the enhancer component in the composition and/or to enhance the antimicrobial efficacy and/or the speed of antimicrobial efficacy. Incorporation of a sufficient amount of hydrophilic component in hydrophobic ointments can increase the antimicrobial activity both in terms of speed of kill and extent of kill. While not intended to be bound by theory, the incorporation of the hydrophilic component may allow more of the antimicrobial component to be available at the surface or to more rapidly diffuse through the tymphanic membrane during use. This is especially true for antimicrobials that are at least partially soluble in the hydrophilic component. The hydrophilic component may also help the diffusion of antimicrobials with poor water solubility into the tissue. This may help eradicate microorganisms from tissue that is heavily colonized or colonized with biofilm and/or microorganisms harboring beneath the surface of the tissue or even within mammalian cells.

In general, the ratio of total hydrophilic component to total hydrophobic component (water insoluble ingredients) is at least 5:95 weight ratio (wt/wt), preferably at least 10:90 wt/wt, more preferably at least 15:85 wt/wt, and even more preferably at least 20:80 wt/wt. Levels as high as 30:70, 40:60, and 50:50 wt/wt of total hydrophilic component to total hydrophobic component (water insoluble ingredients) or higher may be appropriate for certain compositions.

Certain compositions may be solutions, emulsions (one liquid/gel/paste dispersed in another liquid/gel/paste), dispersions (solid in liquid/paste/gel), or combinations thereof.

A hydrophilic material is typically a compound that has a solubility in water of at least 7 wt-%, preferably at least 10 wt-%, more preferably at least 20 wt-%, even more preferably at least 25 wt-%, and even more preferably at least 40 wt-%, at 23° C. Most preferably, a hydrophilic component is infinitely miscible with water at 23° C.

Exemplary hydrophilic components include, but are not limited to, water, polyhydric alcohols, lower alkyl ethers (i.e., having a sufficiently small number of carbon atoms to meet the solubility limit above), N-methylpyrrolidone, alkyl esters (i.e., having a sufficiently small number of carbon atoms to meet the solubility limit above), and the lower monohydroxy alcohols discussed above as enhancers, as well as combinations thereof. Thus, a lower monohydroxy alcohol can function as both a hydrophilic compound and an enhancer. Preferably, the hydrophilic components include polyhydric alcohols, lower alkyl ethers, and water soluble or water dispersible esters. More preferably, the hydrophilic components include polyhydric alcohols.

Suitable polyhydric alcohols (i.e., organic compounds having more than one hydroxyl group) have a molecular weight of less than 500, preferably less than 400, and more preferably less than 200. Examples of polyhydric alcohols include, but are not limited to, glycerol, propylene glycol, dipropylene glycol, tripropylene glycol, polypropylene glycol, polyethylene glycol, diethylene glycol, pentaerythritol, trimethylolpropane, trimethylolethane, trimethylolbutane, sorbitol, mannitol, xylitol, pantothenol, ethylene glycol adducts of polyhydric alcohol, propylene oxide adducts of polyhydric alcohol, 1,3-butanediol, dipropylene glycol, diglycerine, polyglycerine, erythritol, sorbitan, sugars (e.g., sucrose, glucose, fructose, mannose, xylose, saccharose, trehalose), sugar alcohols, and the like. Certain preferred polyhydric alcohols include glycols (i.e., those containing two hydroxyl groups), glycerin, and propylene glycol. Certain other preferred polyhydric alcohols include sucrose, xylitol, mannitol, and sorbitol.

Ethers include materials such as dimethylisosorbide, polyethylene glycol and methoxypolyethylene glycols, block and random copolymers of ethylene oxide and propylene oxide, and laureth-4. Alkyl esters include triacetin, methyl acetate, methyl lactate, ethyl lactate esters, esters of polyethoxylated glycols, and combinations thereof.

Water dispersible hydrophilic components include compounds that are solid, liquid, gel, or wax-like at room temperature but, in particular, those water dispersible hydrophilic vehicles that are liquids, gels, or ointments at room temperature are particularly preferred. Preferred dispersible vehicles include typically amphipathic compounds such as polyalkoxylated ethers and esters. For example, particularly preferred components include, polyethoxylated castor oil (or hydrogenated castor oil), polyethoxylated esters or ethers of saturated or unsaturated fatty alcohols such as PEG 6 oleate (oleth-6), PEG 8 dioleate, and the like. Also included in this group are mixed alkoxylated polymers. For example, water dispersible poloxamers, reverse poloxamers, random and block copolymers of ethylene oxide and propylene oxide initiated onto any glycol having 2-6 alcohol groups, polyurethane polymers of polypropylene glycol or polyethylene glycol (PEG), PEG esters of fatty acids, polyethoxylated polyhydroxyfunctional glycol esters such as polyethoxylated glycerin mono-, di-, and tri-esters, sorbitan mono-, di-, and tri-esters, and polyglycerin fatty acid esters. In some embodiments the dispersible vehicle may be the antimicrobial component. For example, a PEG 3 monoglyceride or PEG 5 propylene glycol fatty acid ester may have antimicrobial activity and can also function as the vehicle. In most embodiments, the water content is less than 20%, preferably less than 10%, and more preferably less than 5% by weight of the composition.

In certain preferred embodiments, the hydrophilic components useful in the compositions described herein include those selected from the group consisting of polyhrydric alcohols, and in particular glycerin and propylene glycol, and mixtures thereof. Most preferably, the hydrophilic component is selected to match the polyhydric alcohol portion of any fatty acid monoester of a polyhydric alcohol antimicrobial present. For example, if the antimicrobial agent was glycerolmonolaurate (monolaurin) the most preferred hydrophilic component is glycerin. In this manner, any transesterification reaction that may occur with the carrier solvent does not produce an undesirable by-product. If there are other components in the composition that may esterify with hydroxylfunctional hydrophilic components, conditions are selected to minimize this occurrence. For example, the components are not heated together for extended periods of time, and/or the pH is close to neutral if possible, etc.

One or more hydrophilic materials may be used in the compositions described herein at a suitable level to produce the desired result. In certain preferred embodiments that also include the hydrophobic component as the primary component (i.e., the component used in the greatest amount and referred to as a "vehicle"), the hydrophilic component is present in a total amount of at least 0.1%, preferably at least 1 wt-%, more preferably at least 4 wt-%, and even more preferably at least 8 wt-%, based on the weight of the ready to use composition. In certain embodiments, for example, when faster rate of kill is desired, higher levels of hydrophilic component may be employed. In these cases the hydrophilic component is present in a total amount of at least 10 wt-%, more preferably at least 20 wt-%, and even more preferably at least 25 wt-%.

In a preferred embodiment, the hydrophilic component is present in a total amount of no greater than 70 wt-%, preferably no greater than 60 wt-%, more preferably no greater than 40 wt-%, even more preferably no greater than 30 wt-%, based on the ready to use composition. When the hydrophilic component is present in the greatest amount it is referred to as a "vehicle."

For certain applications, it may be desirable to formulate the antimicrobial component in compositions including a hydrophilic component vehicle that is thickened with soluble, swellable, or insoluble (preferably, insoluble) organic polymeric thickeners or inorganic thickeners such as silica, fumed silica, precipitated silica, silica aerogel and carbon black, and the like; other particle fillers such as calcium carbonate, magnesium carbonate, kaolin, talc, titanium dioxide, aluminum silicate, diatomaceous earth, ferric oxide and zinc oxide, clays, and the like; ceramic microspheres or glass microbubbles; ceramic microspheres suc as those available under the tradenames ZEOSPHERES or Z-LIGHT from 3M Company, St. Paul, Minn. The above fillers can be used alone or in combination.

If water is used in certain embodiments, it is preferably present in an amount of less than 20%, preferably less than 10 wt-%, more preferably less than 5 wt-%, even more preferably less than 2 wt-%, and even more preferably less than 1 wt-%, based on the ready to use composition. This helps the physical stability of the compositions and may reduce irritation. For certain other embodiments, water can be used in a much greater amount, and can even be the primary components. Preferably, such highly viscous compositions have a viscosity of at least 500 centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). The viscosity can be measured as described below in the Viscosity Test. Most preferred compositions meet these viscosity values even after heating to 32° C. or even 35° C. or as high as 37° C. to ensure when in contact with mammalian tissue the compositions remain substantive.

In some embodiments of the present invention, the compositions have a viscosity of at least 20 cps, preferably at least 100 cps, when measured by the Viscosity Test described herein. Higher viscosities are preferred to reduce migration as well as to provide substantivity (resistance to removal by fluids) to ensure long-term antimicrobial activity.

Hydrophobic Component

Certain preferred compositions described herein also include one or more hydrophobic materials. In certain embodiments, the hydrophobic component can be the same as the antimicrobial component. For example, when the antimicrobial component is an antimicrobial lipid this component may also serve as a hydrophobic component. A hydrophobic material is typically an organic compound, which at 23° C. is a liquid, gelatinous, semisolid or solid and has a solubility in water of less than 5% by weight, preferably less than 1% by weight, more preferably less than 0.5% by weight, and even more preferably less than 0.1% by weight. These materials include compounds typically considered emollients in the cosmetic art.

Examples of general emollients include, but are not limited to, short chain (i.e., C1-C6) alkyl or (C6-C12)aryl esters of long (i.e., C8-C36) straight or branched chain alkyl or alkenyl alcohols or acids and polyethoxylated derivatives of the alcohols; short chain (i.e., C1-C6) alkyl or (C6-C12)aryl esters of (C4-C12)diacids or (C4-C12)diols optionally substituted in available positions by —OH; (C2-C18)alkyl or (C6-C12)aryl esters of glycerol, pentaerythritol, ethylene glycol, propylene glycol, as well as polyethoxylated derivatives of these; (C12-C22)alkyl esters or (C12-C22)ethers of polypropylene glycol; (C12-C22)alkyl esters or (C12-C22)ethers of polypropylene glycol/polyethylene glycol copolymer; and polyether polysiloxane copolymers. Additional examples of hydrophobic components include cyclic dimethicones, including volatile cyclic silicones such as D3 and D4, polydialkylsiloxanes, polyaryl/alkylsiloxanes, silicone copolyols, long chain (i.e., C8-C36) alkyl and alkenyl esters of long (i.e., C8-C18) straight or branched chain alkyl or alkenyl alcohols or acids, long chain (i.e., C8-C36) alkyl and alkenyl amides of long straight or branched chain (i.e., C8-C36) alkyl or alkenyl amines or acids; hydrocarbons including straight and branched chain alkanes and alkenes such as isoparafins (e.g., isooctane, isododecane, isooctadecane, etc.), squalene, and mineral oil, polysiloxane polyalkylene copolymers, dialkoxy dimethyl polysiloxanes; (C12-C22)alkyl and (C12-C22)alkenyl alcohols, and petroleum derived alkanes such as isoparafins, petrolatum, petrolatum USP, as well as refined natural oils (especially NF or USP grades) such as olive oil NF, cotton seed oil, peanut oil, corn oil, castor oil, sesame oil, safflower oil, soybean oil, and the like, and blends thereof. In certain preferred embodiments, the hydrophobic components useful in the compositions described herein include those selected from the group consisting of petrolatum USP and short chain (i.e., C1-C6)alkyl or (C6-C12)aryl esters of long (i.e., C8-C36) straight or branched chain alkyl or alkenyl alcohols or acids and polyethoxylated derivatives of the alcohols; short chain (i.e., C1-C6)alkyl or (C6-C12)aryl esters of (C4-C12) diacids or (C4-C12)diols optionally substituted in available positions by —OH (such as diisopropyladipate, diisopropylsebacate); (C1-C9)alkyl or (C6-C12)aryl esters of glycerol, pentaerythritol, ethylene glycol, propylene glycol (such as glyceryl tricaprylate/caprate); and mixtures thereof. Other useful emollients include (C12-C15)alkyl esters of benzoic acid, fatty alcohols such as stearyl or cetyl alcohol, and lanolin USP or lanolin derivatives. For certain particularly preferred embodiments, the hydrophobic component is petrolatum.

One or more hydrophobic materials may be used in the compositions described herein at a suitable level to produce the desired result. In a preferred embodiment (in which the compositions include very little or no water), the hydrophobic component is present in a total amount of at least 50 wt-%, more preferably at least 70 wt-%, and even more preferably at least 80 wt-%, based on the ready to use composition. In a preferred embodiment, the hydrophobic component is present in a total amount of no greater than 99 wt-%, more preferably no greater than 95 wt-%, and even more preferably no greater than 92 wt-%, based on the ready to use composition. When the hydrophobic component is present in the greatest amount it is referred to as a "vehicle." In those formulations where the hydrophobic component(s) and the hydrophilic component(s) are present at the same concentrations, the continuous phase is considered the "vehicle."

Optional Additives

Compositions of the present invention may additionally employ adjunct components conventionally found in pharmaceutical compositions in their art-established fashion and at their art-established levels. Thus, for example, the compositions may contain additional compatible pharmaceutically active materials for combination therapy (such as supplementary antimicrobials, anti-parasitic agents, antipruritics, antipyretics, astringents, local anaesthetics, analgesics, steroids, non-steroidal anti-inflammatory agents, or other anti-inflammatory agents, sodium channel blockers, and the like), or may contain materials useful in physically formulating various dosage forms of the present invention, such as excipients, dyes, perfumes, lubricants, thickening agents, stabilizers, skin penetration agents, preservatives, or antioxidants. In certain preferred embodiments, compositions of the present invention include an anaesthetic or an analgesic.

A particularly preferred class of pharmaceutically active materials are anti-inflammatory agents. These may be selected from any of those listed in published US Pat. Application Publication No. 2004/0126414. Preferred anaesthetics include, for example, benzocaine, butamben picrate, tetracaine, dibucaine, prilocalne, etidocaine, mepivacaine, bupivicaine, and lidocaine. Preferred non-steroidal anti-inflammatory agents include, for example, detoprofen, diclofenac, diflunisal, etodolac, fenoprofen, flurbiprofen, indomethacin, ketoprofen, mechlofenameate, mefenamic acid, meloxicam, nabumeone, naproxen sodium, oxaprozin, piroxicam, sulindac, tolmeting, celecoxib, rofecoxib, choline salicylate, salsate, sodium salicylate, magnesium salicylate, aspirin, ibuprofen, paracetamol, acetaminophen, and pseudoephedrine. Preferred steroids include, for example, hydrocortisone, prednisone, fluprednisolone, triamcinolone, dexamethasone, betamethasone, cortisone, prednilosone, methylprednisolone, fluocinolone acetonide, flurandrenolone acetonide, and fluorometholone.

It will be appreciated by the skilled artisan that the levels or ranges selected for the required or optional components described herein will depend upon whether one is formulating a composition for direct use, or a concentrate for dilution prior to use, as well as the specific component selected, the ultimate end-use of the composition, and other factors well known to the skilled artisan.

It will also be appreciated that additional antiseptics, disinfectants, or antibiotics may be included and are contemplated. These include, for example, "azole" antifungal agents including clortrimazole, miconazole, econazole, ketoconazole, triclosan, and salts thereof; and the like. Preferred compositions, however, are free of antibiotics and antigens due to the chance of resistance formation.

In certain embodiments, compositions of the present invention include a second active agent that includes a local anesthetic, analgesic, anti-inflammatory agent, an antipyretic, or combinations thereof.

Formulations and Methods of Preparation

Many of the compositions of the present invention have exceptional broad spectrum antimicrobial activity and thus are generally not terminally sterilized but if necessary may be sterilized by a variety of industry standard techniques. For example, it may be preferred to sterilize the compositions in their final packaged form using electron beam. It may also be possible to sterilize the sample by gamma radiation or heat. Other forms of sterilization may be acceptable. While not generally required it may also be suitable to include preservatives in the formulation to prevent growth of certain organisms. Suitable preservatives include industry standard compounds such as parabens (methyl, ethyl, propyl, isopropyl, isobutyl, etc), 2 bromo-2 nitro-1,3 diol; 5 bromo-5-nitro-1,3 dioxane, chlorbutanol, diazolidinyl urea; iodopropylnyl butylcarbamate, phenoxyethanol, benzyl alcohol, benzalkonium chloride and other quaternary amine surfactant antimicrobials, halogenated cresols, methylchloroisothiazolinone and the like, as well as combinations of these compounds.

The compositions of the present invention preferably adhere well to mammalian tissues (particularly, skin, mucosal tissue, and wounds), in order to deliver the antimicrobial to the intended site over a prolonged period even in the presence of hydration, drainage (e.g., inflammatory and cerumen secretions), or mild lavage. The component in the greatest amount (i.e., the vehicle) in the formulations of the invention may be any conventional vehicle commonly used for topical treatment of human or animal skin. The formulations are typically selected from one of the following types: (1) anhydrous or nearly anhydrous formulations with a hydrophobic vehicle (i.e., the hydrophobic component, which can include one or more hydrophobic compounds, is present in the greatest amount); (2) anhydrous or nearly anhydrous formulations with a hydrophilic vehicle (i.e., the hydrophilic component, which can include one or more hydrophilic compounds, is present in the greatest amount) or a dispersible vehicle (i.e the dispersible amphipathic component is present in greatest amount); (3) aqueous-based formulations; and (4) neat compositions. These are discussed below.

(1) Anhydrous or Nearly Anhydrous Formulations with a Hydrophobic Vehicle. In certain preferred embodiments of the present invention, the compositions include an antimicrobial component in a hydrophobic vehicle optionally in combination with surfactant(s), an enhancer component, and a hydrophilic component. In many instances the enhancers are not soluble in the hydrophobic component at room temperature although they may be at elevated temperatures. It may be convenient to choose an enhancer that is soluble in order to ensure physical stability. In many instances a hydrophilic component may be generally present in a sufficient amount to stabilize (preferably to solubilize) the enhancer(s) in the composition. For example, when formulating with organic acid enhancers or certain solid surfactants in petrolatum many enhancers and surfactants will dissolve into the petrolatum at temperatures above 85° C.; however, upon cooling, the enhancer and/or surfactant crystals or precipitates back out of solution making it difficult to produce a uniform formulation. If at least 0.1%, and preferably at least 1.0%, more preferably at least 5%, and most preferably at least 10 wt-%, of a hydrophilic compound (e.g., a glycol) is added, a stable formulation can be obtained. It is believed that these formulations produce an emulsion or suspension (or both) in which the enhancer and/or surfactant is dissolved, emulsified, or dispersed in the hydrophilic component which is emulsified into the hydrophobic component(s). These compositions are stable upon cooling and centrifuging. In more viscous systems it may be acceptable to suspend insoluble components in the vehicle.

The hydrophilic component also helps to stabilize many of the surfactants used in preferred formulations. For example, dioctylsulfosuccinate sodium salt (DOSS) dissolves in glycerin at elevated temperatures and helps keep the DOSS physically stable in the composition. Furthermore, it is believed that incorporation of the hydrophilic component in the formulation improves the antimicrobial activity. The mechanism for this is unknown; however, it may speed the release of the enhancer component and/or the antimicrobial component.

The water content of these formulations is preferably less than 20%, preferably less than 10 wt-%, more preferably less than 5 wt-%, and even more preferably less than 2 wt-%, in order to minimize hydrolysis of any ester and/or antimicrobial present.

Furthermore, it has been found that it is particularly desirable where the antimicrobial component is an antimicrobial lipid based on the ester of glycerin or propylene glycol includes an ester to use either glycerin or propylene glycol in the hydrophilic component. It is most preferred to use a hydrophilic compound that is identical to the glycol portion of the antimicrobial lipid, e.g., propylene glycol with the propylene glycol esters and glycerin with the glycerin esters. In this manner, transesterification of the antimicrobial lipid ester with the hydrophilic compound will not result in additional chemical species present. In fact, there is some evidence to show that use of glycerolmonolaurate, which is 95% pure, when formulated with glycerin as a hydrophilic compound results in formation of additional glycerol monolaurate due to transesterification of the diester with the glycerin to produce two moles of the monoester. For this reason, it may be possible to initially formulate with lower grade glycerin ester that contains considerable levels of diester present, as long as it transesterifies during manufacture and/or storage to produce a formulation that includes less than 15% diester and preferably less than 5% diester based on the total weight of antimicrobial lipid present.

These formulations can be relatively easily manufactured by first heating the hydrophobic component to 85° C. (if necessary), adding in the surfactant, hydrophilic component, and enhancer component, cooling to 65° C., and adding the antimicrobial component above its melting point (if applicable and less than a temperature which would result in significant degradation of the components). Alternatively, the enhancer component can be predissolved in the hydrophilic component (optionally along with the surfactant) and added to the hydrophobic component either before or after addition of the antimicrobial component. If either the antimicrobial component or the hydrophobic component are solids at room temperature this is done at the minimum temperature necessary to melt, or dissolve all components. If the antimicrobial component does not dissolve it may be sufficient to simply ensure a uniform and stable dispersion. Exposure of ester containing components (e.g., an oil or antimicrobial lipid) to components that include either acid or hydroxyl groups (e.g., enhancers) to elevated temperatures for extended periods of time should be avoided to prevent transesterification reactions (unless this is deliberate in the case of utilizing lower purity fatty acid esters in combination with glycol hydrophilic components to produce the monoesters as discussed above).

Thus, the present invention provides methods of manufacture. One preferred method involves: dissolving or dispersing the enhancer component in the hydrophilic component; combining the hydrophobic vehicle and the hydrophilic component with the enhancer component dissolved or dispersed therein with mixing to form a mixture; optionally heating the hydrophobic vehicle to a temperature sufficient to form a pourable liquid (which for many hydrophobic vehicles this is above its melting point) before or after combining it with the hydrophilic component and enhancer component; adding the antimicrobial component to the mixture; and cooling the mixture before or after adding the antimicrobial component.

The hydrophilic component may or may not be present in the formulations that include a hydrophobic vehicle. Thus, another preferred method of manufacture involves: combining the enhancer component and the hydrophobic vehicle with mixing to form a mixture; optionally heating the hydrophobic vehicle to a temperature sufficient to form a pourable liquid (which for many hydrophobic vehicles is above its melting point) before or after combining it with the enhancer component; adding the antimicrobial component to the mixture with mixing; and cooling the mixture before or after adding the antimicrobial component.

It should be noted that the hydrophilic component can be replaced in part or completely with a dispersible amphipathic component in any of the previous discussion concerning Anhydrous or Nearly Anhydrous Formulations with a Hydrophobic Vehicle.

Surprisingly, it has been found that these compositions are significantly less irritating than formulations using completely hydrophilic components. In blind human trials, participants were asked to instill 0.5 gram (g) of ointments based on hydrophobic components (e.g., petrolatum) into their anterior nares that include an AHA enhancer, surfactant, and 10% hydrophilic component (e.g., glycerin) as well as ointments based on hydrophilic components (e.g., PEG 400/PEG 1450) using the same enhancer and surfactant. Surprisingly, the ointments based on the hydrophobic component were preferred by 100% of the participants.

Most preferably, the formulations intended for use in the ear where drainage would be a concern may be formulated to be gelatinous at room temperature, having a significant yield point such that they do not flow readily at temperatures below 35° C. The viscosity is measured using the viscosity test described herein. Certain gelatinous vehicles may also have a characteristic temperature at which they "melt" or begin to dramatically lose viscosity. Preferably this is higher than body temperature also to ensure that excess drainage of the composition of the treatment site does not occur. Therefore, the melting point of the composition is preferably greater than 32° C., more preferably greater than 35° C., and even more preferably greater than 37° C. The melting point is taken as the lowest temperature at which the viscosity becomes dramatically less. In most situations the composition will be applied as an ear drop in a liquid relatively low viscosity form, e.g., having a viscosity of less than about 500 cps and typically less than about 200 cps.

Similarly, if desired, the viscosity and/or melt temperature can be enhanced by either incorporating a crystalline or semi-crystalline hydrophobic carrier such as a higher melting petrolatum or microcrystalline waxes, and crystialline or semi-crylastalline emulsifiers, addition of an insoluble filler/thixotrope, or by addition of a polymeric thickener (e.g., a polyethylene wax in a petrolatum vehicle). Polymeric thickeners may be linear, branched, or slightly crosslinked. It is important for comfort that the formulations are relatively soft and that they spread easily to allow easy application since the tissue may be inflamed with significant preexisting pain for the patient. A particularly preferred vehicle in areas such as these where high viscosity is desirable is white petrolatum USP having a melting point greater than 30° C., and preferably greater than 35° C. Mineral jelly may also be suitable.

(2) Water in Oil Emulsions. Antimicrobial components of this invention can be formulated into water-in-oil emulsions in combination with enhancer(s) and surfactant(s). Particularly preferred compositions comprise at least 35%, preferably at least 40%, more preferably at least 45%, and most preferably at least 50%, by weight oil phase. As used herein the oil phase includes all components which are either not soluble in water or preferentially soluble in the oil(s) present at 23° C. One method of preparing these emulsions is described in International Publication No. WO 2003/028767. Generally speaking, the hydrophobic component (oil) is mixed in Container A along with any emulsifier(s) optionally including polymeric emulsifiers and heated to a temperature sufficient to ensure a homogenous composition and subsequent stable emulsion. The temperature is typically raised to at least 60° C., preferably to at least 80° C., and more preferably to 100° C. or more. In a separate Container B, the hydrophilic ingredients are mixed, including one or more of the following: water, hydrophilic component, enhancer(s), surfactant(s), and acids/bases to adjust the pH of the final composition. The contents of container B are heated to a temperature sufficient to ensure a stable final emulsion composition without significantly degrading any of the components, typically to a temperature greater than 40° C., preferably greater than 50° C., and more preferably greater than 60° C. While hot, container B is added to container A using a high shear mixer. The composition may be continuously mixed until cool (e.g., to a temperature of less than 40° C.) or it can be allowed to sit as long as the contents remain uniformly mixed. If the antimicrobial is heat sensitive, it is added with mixing during the cooling down period. If it is not heat sensitive, it may be added to either container A or container B. The viscosity of these compositions may be adjusted by altering the levels of emulsifier; changing the ratio of water to oil phase; selection of the oil phase (e.g., select from an oil (hydrophobic component), which is more or less viscous); incorporation of a polymeric or particulate thickener, etc.

(3) Hydrophilic Vehicle or a Dispersible Vehicle. Antimicrobial components of this invention can be formulated into a hydrophilic component such as that based on the hydrophilic compounds (discussed above) or into a dispersible amphipathic vehicle optionally in combination with the enhancer(s) and surfactant(s). Particularly preferred are polyethylene glycols (PEGs), including blends of different molecular weight PEGs, optionally containing one or more glycols. When using a hydrophilic component as the vehicle (i.e., the component used in the greatest amount, which can include one or more hydrophilic compounds), it should be preferably selected to maintain viscosity and melt temperature characteristics similar to those stated above for the anhydrous or nearly anhydrous formulations using a hydrophobic vehicle.

Similarly the viscosity can be enhanced by either incorporating a crystalline or semicrystalline hydrophilic compound such as a PEG of sufficient molecular weight, addition of an insoluble filler/thixotrope, or by addition of a polymeric thickener. Polymeric thickeners may be linear, branched, or slightly crosslinked. It is desirable for comfort that the formulations are relatively soft and that they spread easily to allow easy application, especially in the urethra or colonized/infected area. For this reason, a particularly preferred vehicle is based on a blend of a liquid or semi-solid PEG (PEG 400-1000) with a more crystalline PEG (PEG 1000-2000). Particularly preferred is a blend of PEG 400 with PEG 1450 in a ratio of 4:1.

In certain preferred embodiments of the present invention, the compositions are in the form of an ointment or cream. That is, the compositions are in the form of a relatively viscous state such that they are suitable for application to nasal passageways. These hydrophilic or dispersible creams may hydrate rapidly and/or melt or otherwise loose viscosity to rapidly wet the ear canal and/or tympanic membrane and/or Eustachian tube. Preferably, such compositions have a viscosity of at least 500 Centipoise (cps), more preferably at least 1,000 cps, even more preferably at least 10,000 cps, even more preferably at least 20,000 cps, even more preferably at least 30,000 cps, even more preferably at least 50,000 cps. Some compositions could have viscosities exceeding 100,000 cps. The viscosity can be measured as described below in the Viscosity Test. Preferred formulations have high viscosity at room temperature but drop in viscosity significantly after application to mammalian tissue at 32-37° C. due to temperature, hydration, other factors or combinations thereof.

For many applications where the composition will be applied as an ear drop in a liquid relatively low viscosity form, e.g., having a viscosity of less than about 500 cps and typically less than about 200 cps. In these compositions thickeners may not be necessary.

(4) Water-based Formulations. Aqueous compositions of the present invention are those in which water is present in the greatest amount, thereby forming the "vehicle." For these systems it is particularly important that a relatively high viscosity be imparted to the composition to ensure that the antimicrobial composition is not rapidly dispersed off the afflicted area. These formulations also adhere well to tissue and thus deliver the antimicrobial to the intended site over a prolonged period even in the presence of hydration, drainage (e.g., inflammatory and cerumen secretions), or mild lavage. Such a formulation may be enhanced by a thickener system. The thickener system of the invention is compatible with the antimicrobial composition described above in order to provide suitable antimicrobial efficacy, chemical and physical stability, acceptable cosmetic properties, and appropriate viscosity for retention in the afflicted area.

When applied as an ear drop the compositions of the present invention preferably have a viscosity greater than water in order to help retain the composition on the tissue. Preferably, ear drop type compositions of this invention have a viscosity of at least 5 Centipoise (cps), more preferably at least 10 cps, even more preferably at least 25 cps, even more preferably at least 50 cps, even more preferably at least 100 cps, even more preferably at least 500 cps, even more preferably at least 1000 cps. The viscosity can be measured as described below in the Viscosity Test. Preferred formulations have viscosity greater than 5 cps even after application to mammalian tissue at 32-37° C. Because certain optional ingredients, such as enhancers, hydrophilic compounds, hydrophobic compounds, and the like, may effect the viscosity (either positively or negatively), the measured viscosity is that of the final composition.

Preferred thickener systems used in the compositions of the present invention are capable of producing viscoelastic compositions that are very stable. By varying the amount and type of thickener, the degree of elasticity can be adjusted from almost a purely viscous composition to a highly elastic and even gel-like composition. If emollients are added, increasing the elasticity and/or yield stress of the system imparts added stability to prevent separation of immiscible emollients. Excessive elasticity, however, is not preferred because an excessively elastic composition usually does not provide a cosmetically appealing product.

Thickener systems used in the present invention are capable of achieving high viscosities at relatively low total concentrations. The total concentration of the thickener system is preferably less than 8 wt-%, more preferably less than 5 wt-%, and most preferably less than 3 wt-%, based on the total weight of the ready to use composition. Preferably, the total concentration of the thickener system can be as little as 0.5 wt-%, based on the total weight of the composition. For certain embodiments, however, the total concentration of thickener system is greater than 1 wt-%, based on the total weight of the ready to use composition.

The thickener system can include organic polymers or inorganic thixotropes such as silica gel, clays (such as betonite, laponite, hectorite, montmorrillonite, and the like), as well as organically modified inorganic particulates materials, and the like. As used herein, an organic polymer is considered part of the thickener system if its presence in the composition results in an increase in the viscosity of the composition. Certain polymers that do not have these characteristics may also be present in the composition but do not contribute significantly to the viscosity of the composition. For purposes of this invention, they are not considered part of the thickener system. For example, certain nonionic polymers such as lower molecular weight polyethylene glycols (e.g., those having a molecular weight of less than 20,000) do not increase the viscosity of the composition significantly. These are considered part of the hydrophilic component, for example, rather than part of the thickener system.

The thickener system can be prepared from one or more nonionic, cationic, anionic, zwitterionic, or associative polymers as long as they are compatible with the antimicrobial lipid and enhancer components of the composition. For example, certain acidic enhancers such as those that include carboxylic acid groups are most effective in their protonated form. This requires that the composition has an acidic pH. For this reason, many anionic thickeners based on neutralized carboxylic acid groups would not be suitable. For example, Carbopol-type thickeners based on polyacrylic acid salts do not typically thicken well at pH values of less than 5 and certainly less than a pH of 4.5. Therefore, at lower pH values (i.e., when acidic enhancers are present) if the aqueous compositions are thickened with anionic polymers, the polymers are preferably based on sulfonic acid, sulfate, phosphonic acid, or phosphate groups. These polymers are able to thicken at much lower pH values due to the lower pKa of these acid groups. Preferred polymers of this class include ARISTOFLEX HMB (ammonium acryloyldimethyltaurate/beheneth-25 methacrylate crosspolymer) and ARISTOFLEX ASV (ammonium acryloyldimethyltaurate/NVP copolymer) from Clariant Corporation. Other preferred sulfonic acid polymers are those described in U.S. Pat. No. 5,318,955.

Preferably, the compositions that include an acidic enhancer component are thickened using cationic or nonionic thickeners since these perform well at low pH. In addition, many of the nonionic and cationic polymers can tolerate higher levels of salts and other additives and still maintain high viscosity. Thickeners having sulfonic acids or phosphonic acids groups may also be suitable if the pH of the composition is greater than the pKa of the acid group such that it is at least partially ionized.

A preferred group of nonionic polymeric thickeners include modified celluloses, guar, xanthan gum and other natural polymers such as polysaccharides and proteins, associative polymers based on nonionic ethylenically unsaturated monomers wherein at least one comonomer has at least 16 carbon atoms, and polymers based on ethylenically unsaturated monomers selected from the group consisting of acrylates, acrylamides, vinyl lactams, vinyl acetate and its hydrolyzed derivatives, methyl vinyl ethers, styrene, and acrylonitrile.

A preferred group of cationic polymeric thickeners include cationically modified celluloses, quaternized natural aminofunctional polymers, and polymers based on ethylenically unsaturated monomers selected from the group consisting of acrylates, acrylamides, vinyl lactams, vinyl acetates, methyl vinyl ethers, styrene, and acrylonitrile.

Cationic polymers for use in the compositions of this invention can be selected from both permanently charged quaternary polymers (those polymers with quaternary amines such as Polyquatemium 4, 10, 24, 32, and 37, described below) as well as protonated primary, secondary, and tertiary amine functional polymers that have been protonated with a suitable protonic acid. Preferred protonated cationic polymers are based on tertiary amines. The protonated cationic polymers are preferably protonated with suitable acids that will not result in undue skin irritation. These include, for example, (C1-C10)alkylcarboxylic acids optionally substituted by oxygen (e.g., acetic acid, alpha-hydroxy acids such as lactic acid, gluconic acid, benzoic acid, mandelic acid, and the like), (C1-C10)alkylsulfonic acids (e.g., methylsulfonic acid and ethylsulfonic acid), (C1-C10)alkylhydrogensulfates (e.g., methylhydrogensulfate) and mineral acids (e.g., hydrochloric acid, hydrobromic acid, sulfuric acid, phosphoric acid, and the like).

The charge on protonated cationic polymers is pH dependent. For this reason, in order to ensure the polymer is sufficiently protonated, the pH is adjusted appropriately and should be in the range of preferably 2-9.5, more preferably 2-8, and most preferably 2.5-7.5. The pH of preferred compositions that include acidic enhancers should be lower and is typically 2-5, and preferably 2-4. It should be noted that it is not necessary to have all of the amines on a particular polymer protonated. The level of protonation will to a certain extent be pH dependent. With certain polymers in order to obtain optimum thickening with low skin irritation it may be beneficial to only protonate a small percentage of the available amine groups while with other polymers it may be beneficial to protonate substantially all of the amine groups. This will be easily determined by one skilled in the art.

The quaternary, tertiary, secondary, and primary amine functional polymers may be chosen from natural polymers, modified natural polymers, as well as synthetic polymers. These polymers may be soluble or swellable in the aqueous solvent. Furthermore, these polymers may also possess hydrophobic side chains and thus be associative polymers.

Polymers can be classified as soluble, swellable, or associative in the aqueous compositions. Some polymers may fall into one or more of these classes. For example, certain associative polymers can be soluble in the aqeuous system. Whether they are considered soluble, swellable, or associative in the aqueous system, suitable polymers for use in the compositions of the present invention may be film forming or not. Film forming polymers may retain the active antimicrobial component at the afflicted site for longer periods of time. This may be desirable for certain applications. For example, some film forming polymers may produce compositions that could not be easily washed off with water after being applied and dried.

As used herein, a soluble polymer is one that in dilute solution (i.e., 0.01-0.1 wt-% in the desired aqueous solvent system defined as containing water and any other hydrophilic compounds), after heating for a sufficient time to ensure solubilization of any potentially soluble components, has no significant observable particles of greater than 1 micron in particle size, as determined by light scattering measurements using, for example, Malvern Masterisizer E Laser Particle Size Analyzer available from Malvern Co., Boston, Mass.

As used herein, a swellable polymer is one that in dilute solution (i.e., 0.01-0.1 wt-% in the desired aqueous solvent system), after heating for a sufficient time to ensure solubilization of any potentially soluble components, has a significant (i.e., detectable) number of observable particles of greater than 1 micron in particle size, as determined by light scattering measurements using, for example, Malvern Masterisizer E Laser Particle Size Analyzer.

As used herein, an associative polymer is one that has greater than 2 hydrophobic chains per polymer molecule of greater than 16 carbon atoms. Examples of such polymers are as follows.

Soluble Polymers—Cationic Natural Polymer Derivatives. Cationic modified cellulosic polymers are reported in the literature to be soluble in water. Such polymers have been found to be useful in the present invention. The most preferred modified cellulose products are sold under the trade names CELQUAT (National Starch and Chemicals Corp., Bridgewater, N.J.) and UCARE (Amerchol Corporation, Edison, N.J.). CELQUAT is a copolymer of a polyethoxylated cellulose and dimethyldiallyl ammonium chloride and has the Cosmetic, Toiletry and Fragrance Association (CTFA) designation Polyquatemium-4.

An alkyl modified quaternary ammonium salt of hydroxyethyl cellulose and a trimethyl ammonium chloride substituted epoxide can also be used. The polymer conforms to the CTFA designation Polyquatemium 24 and is commercially available as QUATRISOFT LM-200 from Amerchol Corp., Edison, N.J.

A particularly suitable type of cationic polysaccharide polymer that can be used is a cationic guar gum derivative, such as guar hydroxypropyltrimonium chloride (Commercially available from Rhone-Poulenc under the trade designation JAGUAR).

Soluble Polymers—Cationic Synthetic Polymers. Synthetic cationic linear polymers useful in the present invention are preferably quite high in cationic charge density—generally having greater than 10 wt-% cationic monomer, preferably greater than 25 wt-%, and more preferably greater than 50 wt-%. This ensures a good cosmetic feel and may actually improve water solubility. In general, the polymers useful in the present invention have sufficient molecular weight to achieve thickening at generally less than 5 wt-% polymer, but not too high that the lotion/cream/ointment feels slimy and stringy. While the composition of the polymer will dramatically affect the molecular weight at which sufficient thickening will occur, the polymers preferably have a molecular weight of at least 250,000 daltons, and more preferably at least 500,000 daltons. The polymers preferably have a molecular weight of no greater than 3,000,000 daltons, and more preferably no greater than 1,000,000 daltons. The homopolymers are preferably prepared from methacryloyloxyalkyl trialkyl ammonium salt, acryloyloxyalkyl trialkyl ammonium salt, and/or quaternized dialkylaminoalkylacrylamidine salt. Preferably the polymers are copolymers of at least two monomers selected from the group consisting of trialkylaminoalkyl acrylate and methacrylate salts, dialkyldiallyl ammonium salts, acrylamidoalkyltrialkyl salts, methacrylamidoalkyltrialkyl salts, and alkyl imidazolinium salts, N-vinyl pyrrolidinone, N-vinyl caprolactam, methyl vinyl ether, acrylates, methacrylates, styrene, acrylonitrile, and combinations thereof. Typically, for the salts the counterions are preferably $F^-$, $Cl^-$, $Br^-$, and $CH_3(CH_2)_nSO_4^-$ where n=0-4.

A variety of quaternary copolymers of varying quaternization, can be synthesized based on homo or copolymers of amino acrylates with methyl, ethyl, or propyl side chains. These monomers could also be copolymerized with other nonionic monomers including quaternary acrylic homopolymers, such as homopolymers of 2-methacryloxyethyl trimethylammonium chloride and 2-methacryloxyethyl methyl diethyl ammonium bromide; and copolymers of quaternary acrylate monomers with a water-soluble monomers, such as Petrolite Product No. Q-0043, a proprietary copolymer of a linear quaternary acrylate and acrylamide at high molecular weight (4-5 million MW).

Another useful soluble cationic polymer is N,N-dimethylaminopropyl-N-acrylamidine (which is quaternized with diethylsulfate) bound to a block of polyacrylonitrile. This block copolymer is available under the trade designation Hypan QT-100 from Lipo Chemicals Inc., Paterson, N.J. It is quite effective at thickening aqueous systems and has a good cosmetic feel. This polymer as received, however, has an objectionable amine odor. The odor could probably be masked with the proper fragrance, but is preferably removed prior to formulation (e.g., with a solvent cleaning process) so that the formulation can be supplied without fragrance. Preferred compositions are free of fragrances and colorants.

Suitable cationic polymers include, for example, copolymers of 1-vinyl-2-pyrrolidine and 1-vinyl-3-methyl-imidazolium salt (e.g., chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate, referred to in the industry (CTFA) as Polyquaternium-11. This material is available commercially from ICI Corp., Wayne, N.J., under the trade designation GAFQUAT; cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively.

Soluble Polymers-Nonionic. A variety of cellulosic ethers are reported in the literature to be soluble in water. Materials in this class that are nonionic and have been shown to be useful include: methylhydroxypropylcellulose, available as BENECEL MP 943 from Aqualon, Wilmington, Del.; hydroxypropylcellulose, available as KLUCEL (LF, GF, MF, HF) from Aqualon; hydroxybutylmethylcellulose (3.5% hydroxybutyl and 30% methoxyl) from Scientific Polymer Products, Ontario, N.Y.; and hydroxyethylcelluloses, available under the trade designation NATROSOL from Aqualon. Xanthan gum, guar, locust bean gum, and other polysaccharides may also be suitable. These polymers may be produced from plant sources or can be produced through microbial cell culture. Polyvinyl alcohol (PVA) also may be suitable. For example, PVA made from polyvinyl acetate which has been hydrolyzed to 87% is highly water soluble at room temperature. Those with higher percent hydrolysis become progressively more crystalline and may need to be heated to get into solution. Protein thickeners such as gelatin and pectin may also be useful.

Amine oxide polymers such as those described in U.S. Pat. No. 6,123,933 (Hayama) and those commercially available under the trade designation DIAFORMER Z-711, Z-712, Z-731, and Z-751 from Clariant Corp. are useful. Additionally, zwitterionic polymers, such as methacryloyl ethyl betaine/acrylate copolymer that are commercially available under the trade designation DIAFORMER Z-400 from Clariant Corp. can also be used. Zwitterionic polymers described in U.S. Pat. No. 6,590,051 may also be useful.

Carboxylic acid functional polymers including naturally occurring carboxylic acid functional polymers such as hyaluronic acid and derivatives of natural polymers such as carboxymethylcellulose, alginic acid and other alginate polymers, Fucogel (a polysaccharide consisting of three monosaccharides, fucose, galactose, and galacturonic acid), hyaluronic acid, and the like, also may be useful. Synthetic polymers may also be useful, such as those based on carboxylic acid, phosphonic acid, or sulfonic acid functional monomers, including but not limited to, polymers derived from acrylic acid, methacrylic acid, maleic anhydride, itaconic anhydride, sodium AMPS (the sodium salt of 2-acrylamido-2-methylpropane sulfonic acid), sulfopropyl acrylate or methacrylate, sulphomethylated acrylamide, allyl sulphonate, sodium vinyl sulphonate, combinations thereof, or other water-soluble forms of these or other polymerizable carboxylic or sulphonic acids.

Swellable Polymers. Many swellable polymers, which are slightly crosslinked, function as viscosifiers in aqueous solvent systems. In general, these swellable polymers are preferred because they tend to be far less "slimy" when applied and when the hands perspire and are exposed to water after treatment. Excessive crosslinking will result in polymers that do not swell sufficiently to increase the viscosity of the composition. In order to ensure adequate swelling, if a chemical crosslinker is used, the concentration of crosslinker is quite low, e.g., less than 1000 parts per million (ppm), and preferably less than 500 ppm, based on the weight of the dry polymer.

A class of crosslinked polymers suitable for use in the compositions of the present invention include acrylamide and at least one other quaternary monomer selected from the group consisting of trialkylaminoalkylacrylate and methacrylate salts, dialkyldiallyl ammonium salts, acrylamidoalkyltrialkyl ammonium salts, methacrylamidoalkyltrialkyl ammonium salts, and monomers that include imidazolinium salts. The counterions are preferably $F^-$, $Cl^-$, $Br^-$, and $CH_3(CH_2)_nSO_4^-$ where n=0-4. Other comonomers may also be added including N-vinyl pyrrolidone, N-vinyl caprolactam, methyl vinyl ether, acrylates, methacrylates, styrene, and the like. A particularly preferred polymer is a poly(2-methacryloxyethyl trimethyl ammonium chloride) polydimethylaminoethyl methacrylate, which conforms to the CTFA designation Polyquaternium 37. Another preferred polymer includes acrylamide and methacryloyloxyethyl trimethyl ammonium chloride, which conforms to the CTFA designation Polyquaternium 32. These are commercially available from Allied Colloids Inc. of Suffolk, Va. as SALCARE SC95, SC96, and SC92.

Other swellable polymers (i.e., slightly crosslinked polymers) can be prepared using ionizing radiation to crosslink. For example, polymers of N-vinyl lactams, such as N-vinyl pyrrolidone, when exposed to gamma radiation increase in molecular weight and may actually crosslink. This crosslinking allows for more efficient thickening (less polymer required to achieve a certain viscosity) and an improved cosmetic feel. Other polymers that when exposed to gamma radiation result in crosslinking, include polymers such as LUVIQUAT HM 552 (copolymers of vinylimidazolium methochloride and vinylpyrrolidone, which conforms to the CTFA designation Polyquaternium-16), and GAFQUAT HS-100 (vinylpyrrolidone/methacrylamidopropyltrimethylammonium chloride copolymer which conforms to the CTFA designation Polyquaternium-28).

Chemical crosslinking using polyunsaturated monomers such as diallyl maleate may also prove useful. Other suitable crosslinkers are multi-ethylenically unsaturated compounds wherein the ethylenic groups are vinyl groups (including substituted vinyl groups, such as isopropenyl groups), allyl groups, and/or methallyl groups, which groups are bonded to nitrogen or oxygen atoms. Vinyl, allyl, and methallyl groups, as used herein, include substituted derivatives. Exemplary compounds include divinyl, diallyl, or dimethallyl esters, ethers, amides, or ureas. Specific examples are disclosed in U.S. Pat. No. 5,225,473 (Duan) and U.S. Pat. No. 4,931,282 (Asmus et al.).

A range of crosslinked polyvinylpyrrolidone (PVP) materials have been prepared via covalent crosslinking with diallyl maleate or by radiation crosslinking of linear PVP powders. Crosslinked PVP prepared under these techniques can produce colloidal particles which are highly swellable in aqueous solutions and thereby produce viscous solutions. The polymers are also nonionic and have excellent compatibility with cationic excipients.

Anionic swellable polymeric thickeners may also be useful. As described above preferred anionic polymers for use with antimicrobial compositions which include carboxylic acid functional enhancers (and are thus formulated at lower pH) are polymers having sulfonic acid, sulfonate, phosphonic acid, or phosphate groups. Carrageenan is a particularly preferred polymer having sulfonic acid groups.

Associative Polymers. Associative polymers can be used to thicken the compositions of the present invention as well. Such polymers thicken as a result of hydrophobic or Van de Waals association of hydrophobic side chains. Such associative polymers can form viscous to gelled aqueous solutions despite their relatively low molecular weights. Polymers that are alcoholic soluble can be modified by the addition of a long chain hydrophobic group. A preferred class of such associative polymers are based on nonionic ethylenically unsaturated monomers wherein at least one comonomer has at least 16 carbon atoms.

An example is cetyl hydroxyethylcellulose, available as NATROSOL PLUS from Aqualon, which utilizes an associative mechanism to enhance the viscosity it produces. Grafted side chains of cetyl alkyl groups can associate with neighboring alkyl hydrophobes. These interpolymer associations can dramatically increase the viscosification efficiency of the polymer. Longer chain alklyl, alkenyl, and aralkyl groups may also be suitable. For example, another preferred associative polymer is Arsitoflex HMB, which is ammonium acryloyldimethyltaurate/beheneth-25 methacrylate crosspolymer and is available from Clariant Corp.

(5) Neat Compositions. The compositions of the present invention also may be delivered to the treatment site in a neat form or in a volatile solvent that rapidly evaporates to leave behind a neat composition. This may be particularly suitable for delivery to the Eustachian tube but could also be utilized for delivery into the ear canal or to the surface of the tympanic membrane. Such compositions may be solid, semi-solid, or liquid. In the case where the compositions are solid, the antimicrobial and/or the enhancer and/or the surfactant may optionally be microencapsulated to either sustain the delivery or facilitate manufacturing a powder, which is easily delivered. Alternatively, the composition can be micronized into a fine powder without the addition of other components or it may optionally contain fillers and other ingredients that facilitate powder manufacture. Suitable powders include, but are not limited to, calcium carbonate, calcium phosphate, various sugars, starches, cellulose derivatives, gelatin, and polymers such as polyethylene glycols.

When hydrophobic antimicrobial lipids are used, a method for micronizing a hydrophobic agent may be used wherein the hydrophobic agent is dissolved in an effective amount of a first solvent that is free of polymer (such as the method described in U.S. Pat. No. 6,746,635). The hydrophobic agent and the solvent form a mixture having a continuous phase. A second solvent and then an aqueous solution are introduced into the mixture. The introduction of the aqueous solution causes precipitation of the hydrophobic agent and produces a composition of micronized hydrophobic agent having an average particle size of 1 micron or less. The particle size for use in delivery to the nose or other tissue may be significantly larger to direct delivery to the proper site. For example, to deliver the antimicrobial powder to the nose, nasal cavities, and/or throat without passing into the lungs, larger particles may be required.

Bioadhesive polymers optionally may be added to neat compositions as well as the other physical forms. Numerous suitable bioadhesive polymers are discussed in International Publication No. WO 93/21906. Representative bioadhesive polymers of particular interest include bioerodible hydrogels described by H. S. Sawhney et al., in Macromolecules, 26:581-587 (1993), including polyhyaluronic acids, casein, gelatin, glutin, polyanhydrides, polyacrylic acid, alginate, chitosan, poly(methyl methacrylates), poly(ethyl methacrylates), poly butylmethacrylate), poly(isobutylmethacrylate), poly(hexlmethacrylate), poly(isodecl methacrylate), poly (lauryl methacrylate), poly(phenyl methacrylate), poly(methyl acrylate), poly(isopropyl acrylate), poly(isobutyl acrylate), and poly(octadecl acrylate). Preferred polymers are polyacrylic acid (e.g., CARBOMER polymers) and poly(fumaric-co-sebacic)acid. Other bioadhesive and bioerodible polymers are described in U.S. Pat. No. 6,746,635. Particularly preferred are slightly crosslinked polyacrylic acids such as those sold under the CARBOPOL brand by BF Goodrich.

The antimicrobial compositions also may include suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

The neat compositions according to the present invention may be conveniently delivered in the form of an aerosol spray or foam presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. Those of skill in the art can readily determine the various parameters and conditions for producing aerosols without resort to undue experimentation. Devices similar to metered dose inhalers (MDI), dry powder inhaler (DPI), spacer/holding chambers in combination with MDI, and nebulizers can be used to deliver compositions to the Eustachian tube or into the ear canal. Techniques for preparing aerosol delivery systems are well known to those of skill in the art. Generally, such systems should utilize components which will not significantly impair the biological properties of the agent (see, for example, Sciarra and Cutie, "Aerosols," in Remington's Pharmaceutical Sciences, 18th edition, 1694-1712 (1990)).

The compounds may also be formulated in rectal or vaginal compositions such as suppositories or retention enemas, e.g., containing conventional suppository bases such as cocoa butter, other glycerides, oils, and the like.

Viscosity

In one embodiment the compositions of the present invention are delivered to the ear canal as a simple "drop" such as typical ear drop medications having a dispenser that the is squeezed to deliver a known number of "drops" of composition as a means of controlling dosage. In these compositions it is important for the composition to be able to flow into the ear when treating both otitis externa and otitis media. Furthermore, it compositions that are instilled directly into the middle ear via a ruptured ear drum (tympanic membrane) the viscosity is preferably relatively low to facilitate rapid distribution within the middle ear. In these applications the compositions should have a viscosity of less than about 20,000 cps, preferably less than about 15,000 cps, more preferably less than about 10,000 cps, even more preferably less than about 5000 cps and most preferably less than about 2000 cps to facilitate passage into the ear canal. To ensure the composition does not drain out immediately and is more substantive to the tissue to be treated the compositions preferably have a viscosity of at least 5 Centipoise (cps), more preferably at least 10 cps, even more preferably at least 25 cps, even more preferably at least 50 cps, even more preferably at least 100 cps, even more preferably at least 500 cps, even more preferably at least 1000 cps. The viscosity can be measured as described below in the Viscosity Test. Preferred formulations have viscosity greater than 5 cps even after application to mammalian tissue at 32-37° C. Because certain optional ingredients, such as enhancers, hydrophilic compounds, hydrophobic compounds, and the like, may effect the viscosity (either positively or negatively), the measured viscosity is that of the final composition. These low viscosity compositions can optionally be delivered in or on a substrate such as a cotton or rayon swab or other non-woven that is left in the ear canal for a period of time.

As previously described certain compositions can be delivered on or in a substrate or as a salve/cream/ointment. In these applications it may be preferable to have certain preferred compositions of the present invention have a viscosity of at least 500 cps for ease of application topically. More preferably at least 1,000 cps, even more preferably at least 10,000 cps, even more preferably at least 20,000 cps, even more preferably at least 30,000 cps, even more preferably at least 50,000 cps. Some compositions could have viscosities exceeding 100,000 cps. Compositions delivered on or in a porous substrate may be very low in viscosity, e.g less than 20 cps or even as low as 5 cps or lower. The viscosity can be measured as described below in the Viscosity Test. Preferred formulations have high viscosity at room temperature but drop in viscosity significantly after application to mammalian tissue at 32-37° C. due to temperature, hydration, other factors or combinations thereof.

Importantly for some applications, the composition should not obstruct the function of the instrument inserted. For example, in the case of an antimicrobial composition inserted into the ear canal the composition preferably does not obstruct vision excessively by an otoscope. Therefore, certain compositions will melt, dissolve, or disperse readily in contact with tissue and/or fluid. In some cases temporary "obstruction" could be present if the viscosity of an ointment is too high on the tissue. This could cause the clinician to have to lavage the ear prior to otoscopic examination.

Some compositions may exhibit thermal induced gelation. That is, when cold the viscosity is low allowing the composition to flow into the ear. When warmed by the body, however, a significant rise in viscosity occurs dramatically increasing the ability of the composition to remain on the affected tissue and not drain back out of the ear. For example, if a composition of the present invention includes certain poloxamer block copolymers of ethylene oxide and propylene oxide generally having greater than 60 mol-% polyethylene oxide and preferably greater than 65 mol % ethylene oxide and generally having less than about 90 mol % and preferably less than 85 mol % ethylene oxide (such as those available under the trade names PLURONIC F127 and F108 from BASF Corp.), as well as certain modified cellulose polymers, and is applied topically, for example, thermally induced gelation can occur. Some modified cellulose polymers, polyacryaltes, and other polymers such as copolymers of polye(thylene glycol) methacryalte and isopropylacylamide as well as block copolymers of methylvinyl ether with isobutylvinyl ether are also known to exhibit this phenomenon. Thus, various components can be selected for use in compositions of the present invention to produce a desired application effect.

Delivery Methods and Devices

Antimicrobial compositions of the present invention can be provided to a medical professional in a single composite formulation or in multiple parts. For example, a composition can be provided in two parts (e.g., in two separate containers or two separate compartments of the same container), one part containing the antimicrobial component and one part containing the enhancer. Other components of the composition can be combined with either one of the two parts. Alternatively, the other components can be included in a third part.

In other embodiments, a composition can be provided in two parts and the antimicrobial lipid component can be made in situ. For example, a monoglyceride could be formed in-situ from a di- or tri-glyceride in the presence of a lipase such as a mammalian or bacterially derived lipase. This may occur on the tissue or prior to application to the tissue.

Topical treatment regimens according to the practice of this invention include applying a safe and effective amount of the compositions described herein directly to the colonized or infected tissue or mucous membrane; particularly, the external ear canal, tympanic membrane, middle ear, and Eustachian tube tissues, and the like, that are particularly susceptible to microbial contamination.

Compositions of the present invention can be delivered using a variety of techniques. Typically, the compositions are delivered to the mammalian tissue in a manner that allows them to spread and perhaps penetrate into the tissue, as opposed to through the tissue into the blood stream. This concentrates the compositions locally at the site in need of treatment. It should be noted, however, that we believe the bulk of the compositions diffuse into the middle ear through the tympanic membrane, diffusion of the composition from the external ear into the middle ear through the tissue surrounding the TM could also be important. This delivery can be accomplished by applying, spraying, squirting, dipping, wiping, dropping, pouring, toweling, nebulizing, or the like, onto the area to be treated.

In the methods of the present invention, the compositions may be provided as a formulation suitable for delivery to mammalian ear tissue (e.g., external ear canal, middle ear, and Eustachian tube tissues). Suitable formulations can include, but are not limited to, creams, gels, foams, ointments, lotions, balms, waxes, salves, solutions, suspensions, dispersions, water in oil or oil in water emulsions, microemulsions, pastes, powders, oils, lozenges, boluses, and sprays, and the like.

The compositions may be sprayed from a pressurized container. The pressure may be supplied by an external means such as squeezing the container, through the use of a mechanical pump, or with the use of a propellant. Suitable propellants include chlorofluorocarbons (CFCs), hydrochlorofluorocarbons (HCFCs), hydrofluorocarbons (HFCs), hydrofluoroethers (HFEs), perfluorinated alkanes, and (C1-C5)alkanes, such as propane and butane, as well as nitrous oxide and dimethyl ether. Preferred propellants are lower alkanes such as propane, butane, isobutene, as well as HCFCs.

If delivered as a foam, the composition may be dispensed from an aerating dispenser such as the F2 Finger Pump Foamer available from Air Spray International Pompano Beach, Fla. Alternatively, the foam may be generated using a suitable propellant such as those described above.

Ideally a dispenser can deliver the antimicrobial composition into the external ear canal and/or TM as well as the surrounding tissue. For example, a dispenser could deliver the antimicrobial composition into the external ear canal onto the TM and tissue surrounding the TM. This can be accomplished, for example, by packaging the composition in a container that has a small tip capable of dispensing composition into the ear canal. For example, a syringe, tube, packet or other package that has a smooth small tip that can be inserted into the ear canal (e.g., an external diameter less than about 7 mm and preferably less than about 5 mm can be used to dispense antimicrobial composition into the ear canal. Alternatively the composition can be packaged in a simple bottle with dropper tip or in a bottle with a separate "eye dropper" and applied as an ear drop that is dropped into the ear with the patient (human or other mammal) in a position to allow the composition to flow toward the TM under the force of gravity. Optionally, antimicrobial composition could simply be expelled onto a pad such as a foam, knit, woven or nonwoven pad or be prepackaged in one of these forms and applied into the ear canal. This delivery may be preferred for compositions which viscosity decreases by melting when in contact with the tissue.

Alternatively, the compositions may be applied directly to the tissue from a collapsible container such as a flexible tube, blow/fill/seal container, pouch, capsule, etc. In this embodiment, the primary container itself is used to dispense the composition directly onto the tissue or it can be used to dispense the composition onto a separate applicator. For example, for delivery to the TM or deep into the external ear canal tissue, the composition could be dispensed directly from a tube and spread by a number of means including squeezing the outside of the ear together repeatedly and/or wiping with a separate device such as a spatula, cotton, rayon, or other natural or synthetic based fiber swab.

Other application devices may also be suitable including applicators with foam tips, brushes, and the like. Importantly, the applicator must be able to deliver the requisite amount of composition to the tissue. These applicators may even be used within the orifice and may be beneficial toward disrupting the bacterial flora and making it easier more susceptible to the antiseptic. Therefore, in most instances applicator devices such as webs and swabs are coated on the applicator web at greater than 50% by weight of the dry web and preferably in excess of 100% by weight of the dry web. On a swab, this would include the weight only of the web and not the applicator stick.

For application to skin or mucosal tissue, for example, the compositions may be applied directly to the tissue from a collapsible container such as a flexible tube, blow/fill/seal container, pouch, capsule, etc. The collapsible containers may be made in a number of single layer, laminate, or coextruded constructions. Materials of construction may include polyolefins such as low, medium, or high density polyethylene including low and linear low density polyethylene, polypropylene, as well as copolymers of ethylene and/or propylene with other polar or non-polar comonomers; polyamides such as nylons; polyesters such as polyethylene terephalate, polybutyleneterephalate, polyethylenenaphthalate; polyurethanes; polyacrylates; and the like. In some constructions it may be desirable to include a barrier material to prevent evaporation of one or more components of the formulation. Suitable barrier materials include polyesters (e.g., polyethylene terephthalate, polyethylene naphthalate, polybutylene terephalate, and the like), fluorinated layers such as polytetrafluoroethylene (PTFE, e.g., TEFLON), polyamides (e.g., nylon), chlorotrifluoroethylene (ACLAR), polyvinylidene fluoride, as well as copolymers of perflourinated monomers with partially fluorinated monomers such as copolymers of tetrafluoroethylene/hexafluoropropylene/vinylidene fluoride (THV Fluorothermoplastic from Dyneon Company), polyvinylchloride, polyvinylidene chloride (PVDC, e.g., SARAN HB), ethylene vinyl alcohol (EVOH), polyolefins (e.g., polyethylene, high density polyethylene, polypropylene, and combinations thereof). Oriented and biaxially oriented polymers may be particularly preferred.

Particularly preferred barrier constructions include metallic foil barriers such as aluminum foil laminates, HDPE, PET, PETG, PEN laminates of polyester and polyolefin (in particular PET/HDPE or HDPE/PET/HDPE), laminates of PET and EVOH, biaxially oriented nylon, PVDC, Nylon/EVOH/Nylon (OXYSHIELD OUB-R), chlorotrifluoroethylene and laminates thereof, ceramic layer including silicon oxide ($SiO_x$ where x=0.5-2 and preferably 1-2) coated thermoplastics, and ceramic coated PET (CERAMIS available from CCL Container/Tube Division, Oak Ridge, N.J.).

In some embodiments, an applicator may be used to place the device and/or antimicrobial composition in the proper location, for example, on the TM.

Also, compositions of the present invention can be coated onto medical devices that contact the affected tissue such as ear tubes (myringotomy tubes) and other devices.

Antimicrobial compositions of the present invention can be formulated for additional controlled release (beyond that provided by the compositions previously discussed) if desired. For example, the antimicrobial and/or enhancer component may be formulated into compatible liposomes, microcapsules, microglobules, microbeads, and/or microspheres such as those made from natural polymers including, but not limited to, polysaccharides, agar, starch and starch derivatives, cellulose and cellulose derivatives, and synthetic polymers such as polyolefins (e.g., polyethylene and polypropylene), polystyrene, polyacrylates, and the like, as well as inorganic materials such as clays and zeolites. The antimicrobial and/or enhancer component may also be formulated into multiple emulsions such as oil-in-water-in-oil emulsions or water-in-oil-in-water emulsions where the oil is an organic oil or a silicone base oil. In addition, water soluble or swellable polymers can be combined with the antimicrobial lipid in a soluble or swollen state, dried, and added to the various compositions to further sustain release. If a prolonged release of the antimicrobial and/or enhancer component is desired it also may be useful to incorporate a hydrophobic component in which the antimicrobial component is soluble.

The dose and frequency of application will depend on many factors including the condition to be treated, the concentration of antimicrobial and enhancer, the microbe to be killed, etc. Typically, the compositions will be delivered in dosages of at least 10 milligrams per square centimeter (mg/$cm^2$) of tissue, preferably at least 20 mg/$cm^2$ of tissue, more preferably at least 30 mg/$cm^2$ of tissue, and most preferably at least 50 mg/$cm^2$ of tissue, for most external applications. In tubular channels such as the external ear or Eustachian tube the passage is preferably filled or sufficient spreading occurs such that complete contact with the colonized tissue is ensured. Application can be made once, or several (e.g., 2-4) times per day for one or more days. Preferred compositions work with a single dose per day over one or more days.

Objects and advantages of this invention are further illustrated by the following examples, but the particular materials and amounts thereof recited in these examples, as well as other conditions and details, should not be construed to unduly limit this invention.

Test Protocols

Antimicrobial Kill Rate Test

Antimicrobial compositions were challenged with test cultures of Methicillin Resistant *Staphyloccus aureus* (MRSA) #MS16266 and *Staphylococcus aureus* (*S. aureus*), ATCC #25923 (commercially available from American Type Culture Collection, Rockville, Md.), *Escherichia coli* (*E. coli*), ATCC #11229, and *Pseudomonas aeruginosa* (*Pseudomonas ae.*), ATCC No. 15442.

Bacteria Culture Preparation:

Bacteria were grown in Tryptic Soy Broth (TSB) (commercially available from Difco, Detroit, Mich.) at 35° C. for 18-24 hours (hrs). A 0.3-milliliter (mL) culture suspension was spread on the surface of a Tryptic Soy Agar plate that was incubated at 35° C. for 18-24 hrs. Bacterial cells were harvested from the agar plate with a glass L-rod by adding 3 mL of TSB and were transferred into a snap cap 5 mL polypropylene culture tube. The resulting cell suspension was called the working culture.

Ointment Test Procedure:

A 50-mL centrifuge tube was filled with 10 mL of each ointment antimicrobial composition. The tube was placed in a temperature controlled water bath equipped with stirring capability. The temperature of the composition was adjusted to 40° C.+/−2° C. where most of the compositions became softened and could be easily mixed. Other compositions may require higher or lower temperatures. Importantly, the temperature should not be increased above about 45° C. at which point the bacteria will perish from temperature effects. It should be confirmed that the temperature did not kill the bacteria in the absence of the antimicrobial composition.

Liquid Test Procedure:

A 25-mL Erlenmeyer flask containing a magnetic stirring bar was filled with 20.0 mL of a liquid antimicrobial composition. The flask was placed in a temperature controlled water bath equipped with stirring capability. The magnetic stirrer was turned on and temperature of the composition was adjusted to 23° C.+/−2° C.

Exposure of Bacteria to the Compositions:

At the start of each exposure time, 0.1 mL of Methicillin Resistant *Staphyloccus aureus, Staphylococus aureus, Escherichia coli,* or *Pseudomonas aeruginosa* working culture was added to the antimicrobial composition. The exposure times were 2 minutes, 5 minutes and 10 minutes. At the end of each exposure time, 1 mL of suspension was transferred to a test tube containing 9 mL Letheen broth (VWR Scientific, Batavia, Ill.) at 23° C. or 40° C. ($10^{-1}$ cell suspension). After vortexing, the neutralized $10^-$ cell suspension was further diluted to $10^{-2}$ by transferring 1 mL into 9 mL Letheen broth tubes. From each of the two dilutions, 0.1 mL volume was plated onto a TSA plate and spread with the L-rod producing $10^{-2}$ and $10^{-3}$ dilutions. The plates were incubated at 35° C.±2° C. for 48 hours (hrs) and colony-forming units (CFU) were counted and recorded. The procedure was repeated using three to five replicate samples of each composition. The diluted bacterial suspensions were plated in duplicate.

Data Analysis:

Microbial kill rate was reported as a $\log_{10}$ reduction which was determined by calculating the difference between the $\log_{10}$ of the initial inoculum count and the $\log_{10}$ of the inoculum count after exposure to compositions or components of the composition for 2-minute ($T_2$), 5-minute ($T_5$), and 10-minute ($T_{10}$) intervals.

The two duplicate plates at the selected dilution level were averaged and the initial inoculum count was calculated using the following formula: Initial Inoculum Count=$T_0$=Ave. CFU of 3 replicates×1/dilution level×0.005

Where the sample inoculums were diluted (0.1 mL in 10 mL of the compositions, the initial inoculum were reduced by 0.1 mL/10 mL, which equals 0.010).

For the test plates of each organism at each time period, the CFU's on all the $10^{-2}$ and $10^{-3}$ plates were counted. The dilution level that had counts between 25 and 250 was determined. The two duplicate plates at the selected dilution level were averaged and the test plate count at the given time was calculated using the following formula:

$T_2$, $T_5$, and $T_{10}$=CFU of 3 replicates×1/dilution level where the plate count of 3 replicates are at 2 minute, 5 minute, and 10 minute intervals, respectively.

For the compositions the log reduction was determined by taking the logarithm to the base 10 of $T_0$, $T_2$, $T_5$, and $T_{10}$ and using the following formulas:

Log reduction at 2 minutes=$\log_{10}T_0 - \log_{10}T_2$

Log reduction at 5 minutes=$\log_{10}T_0 - \log_{10}T_5$

Log reduction at 10 minutes=$\log_{10}T_0 - \log_{10}T_{10}$

The average of the replicates was calculated by averaging the log reductions at each time period.

EXAMPLES

Objects and advantages of this invention are further illustrated by the following examples, but the particular materials and amounts thereof recited in these examples, as well as other conditions and details, should not be construed to unduly limit this invention.

GLOSSARY OF COMPONENTS

| Acronym | Trade Name | Description | Source/Address |
| --- | --- | --- | --- |
| GML | LAURICIDIN | Glycerol monolaurate | MedChem Laboratories, Inc./Galena, IL |
| | PURAC HIPURE 88 | Lactic Acid (88%) | Purac America/ Lincolnshire, IL |
| | | Mandelic Acid | Sigma-Aldrich/St. Louis, MO |
| | | Benzoic acid | Mallinckrodt Baker Inc./ Paris, KY |
| | | Salicylic acid | Mallinckrodt Baker Inc. |
| | SENSIVA 50 | 2-ethylhexyl glycerin ether | Schulke & Mayi Gmbh, Germany |
| PG monocaprate | | Propylene glycol monocaprate | Uniquema/Wilmington, DE |
| DOSS 100% | COMPLEMIX | Dioctylsulfosuccinate, sodium salt | Cytec Ind. West Paterson, NJ |
| DOSS 50% | 50% DOSS | 50% Dioctyl Sodium Sulfosuccinate in PEG-400 | Cytec Industries/West Paterson, NJ |
| SLS | POLYSTEP B12 | Sodium laureth-4 sulfate | Stepan Company/ Northfield, IL |
| PEG-400 | CARBOWAX 400 | Polyethylene glycol, MW = 400 | Dow Chemical Co., Midland, MI |
| | | Glycerin USP | Mallinkrodt Baker Inc. |
| | FINSOLV TN | $C_{12}$-$C_{15}$ benzoate ester | Finetex Inc., Elmwood Park, NJ |

-continued

| Acronym | Trade Name | Description | Source/Address |
|---|---|---|---|
| IPM | | Isopropyl myristate | Cognis Corp./Houston, TX |
| | FILIPPOBENO Olive Oil | Olive oil, 100% Olive Oil | Imported by Salov North America Corp./Hackensack, NJ |
| BHT | | Butylated hydroxytoluene | Sigma-Aldrich/St. Louis, MO |
| EDTA | EDTA (Na)$_2$ | Sodium salt of ethylenediamine tetraacetic acid | Sigma-Aldrich/St. Louis, MO |
| PLURONIC | PLURONIC F-68 | Poloxamer/block copolymer of propylene oxide and ethylene oxide | BASF Corp./Parsippany, NJ |
| CHG | | Chlorhexidine gluconate | Medichem, Spain |
| CHA | | Chlorhexidine diacetate | |
| | | Tartaric acid | Sigma-Aldrich/St. Louis, MO |
| | CAPTEX 355 | Glycerol tricaprylate/caprate | Abitec Corp, Janesville, WI |
| | CAPTEX 300 | Glycerol tricaprylate/caprate | Abitec Corp. Janesville, WI |
| | | $C_{10}H_{23}$ glycerin ether | (Preparation described in Example 26) |
| | CRODAPHOS SG | PPG-5 ceteth-10 phosphate | Croda Inc./Parsipanny, NJ |
| | POLYSTEP B12 | Sodium laureth-4 sulfate | Stepan Company/Northfield, IL |
| | MACKAM 50-SB | Lauramidopropylhydroxysultaine | McIntyre Group Ltd./University Park, IL |
| | HOSTAPUR SAS 93G | Sodium C14-C17 Sec alkyl sulfonate, 93% solids | Clariant Corp./Charlotte, NC |
| | HOSTAPUR SAS 60 | Sodium C14-C17 Sec alkyl sulfonate, 60% solids | Clariant Corp |
| LMDO | AMMONYX LMDO | Lauramidopropyldimethylamine oxide | Stepan Company |
| Pet | Snow White PET USP | White Petrolatum | Penreco |
| | | White beeswax | Acros |
| | PRISORINE 2021 | Isopropyl isostearate | Unichem |
| | SALCARE SC92 | Copolymer of acrylamide and trimethylaminoethylmethacrylate chloride salt | Ciba Specialty Chemicals Corp./High Point, NC |
| | NATROSOL PLUS TYPE | Cetyl hydroxyethyl cellulose | Hercules, Aqualon Division/Wilmington, DE |
| | CERAPHYL 31 | Lauryl Lactate 48% | ISP, Lombard IL |
| | PELEMOL LL | Lauryl Lactate 75% | Pheonix Chemical, Sommerville, NJ |
| | PURASOLV EHL | 2ethylhexyllactate | Purac America, Lincolnshire, IL |
| IPA | | Isopropal alcohol, Reagent grade | VWR International West Chester, PA |

Experimental. Ototoxicity Testing in Chinchillas

Initial screening of selected components for ototoxic effect was preformed using chinchillas. The compounds or compounds plus vehicle were placed in proximity to the round window membrane of the chinchilla and the tissues evaluated for ototoxic insult.

General Test Procedure: Chinchillas were mildly anesthetized using 0.1 cc IM ketamine. The skin overlying the ventral aspect of the left and right bulla were shaved and surgically prepped. An amount (0.1 cubic centimeter (cc)) of the test material was placed in the middle ear near the round window niche using a 1 cc syringe with a 23 guage needle by trans bullar injection. Three days later the procedure was repeated using the same test material in each ear. Fourteen days after the second injection (total survival time=17 days) the animals were sacrificed. The bullae were removed, the cochlea isolated and perfused with fixative through the round window membrane. After standard preparation (fixation and decalcification) the samples were dissected and the Organ of Corti isolated and evaluated for ototoxic insult. The surface preparation analysis of the Organ of Corti is a universally accepted method of evaluating hair cell loss due to ototoxic insult. The chinchilla is the standard test animal used and a 14 day survival time is adequate to screen for gross hair cell disruption due to ototoxic effect. The materials were tested in both a right and left ear but using two different animals. The surface prep histology was rated on a 1 to 4 scale with 1 being not ototoxic and 2-4 being increasingly severe ototoxicity. Presence of infection in the ear resulted in the test ear being removed from the study and not being ranked.

In addition to the experimental treatments, one group received intra-bullar injections with cortisporin, which was known to produce an ototoxic effect. This served as a positive control. Another group was treated with sterile saline which was known to produce no ototoxic effect, it served as a negative control. The results are reported in the Table of Ototoxicity Results below as either no toxicity (rating 1) or toxic (rating 2-4).

TABLE OF OTOTOXICITY RESULTS

| Compound | Function | Ototoxicity Result |
|---|---|---|
| GML 0.5% in water | Antimicrobial lipid | No toxicity |
| GML 1.0% in water | Antimicrobial lipid | No toxicity |
| GML 1% in IPM | Antimicrobial lipid | Toxic |
| PG monocaprylate 0.25% in water | Antimicrobial lipid | No toxicity |
| PG monocaprylate 1% in water | Antimicrobial lipid | No toxicity |
| CHG 0.25% in water | Antimicrobial | Toxic |
| CHA 0.25% in water | Antimicrobial | Toxic |
| Tartaric acid 1% in water | Enhancer | No toxicity |
| Lactic acid 0.5% in water | Enhancer | No toxicity |
| Lactic acid 1.0% in water | Enhancer | No toxicity |
| Mandelic acid 1.0% in water | Enhancer | No toxicity |
| Acetic acid 1% in water | Enhancer | Toxic |
| Propylene glycol 100% | Enhancer/vehicle | Toxic |
| Propylene glycol 50% in water | Enhancer/vehicle | Toxic |
| FINSOLV TN 100% | Vehicle/penetration enhancer | No toxicity |
| PEG 400 | Vehicle | Toxic |
| Olive oil | Vehicle | No toxicity |
| IPM 100% | Vehicle/penetration enhancer | Toxic |
| CAPTEX 355 100% | Surfactant | No toxicity |
| CAPTEX 300 100% | Surfactant | No toxicity |
| PLURONIC F68 10% in water | Surfactant | No toxicity |
| SLS 0.5% in water | Surfactant | Toxic |
| GEMTEX (DOSS) 1% in water | Surfactant | Toxic |
| Cortisporin in water | Positive control | Toxic |
| Saline | Negative control | No toxicity |

Examples 1-4

Antimicrobial compositions were prepared using the components shown in Table 1. The components were combined and heated to obtain a clear solution, that remained clear on cooling to room temperature. These solutions were used for further antimicrobial testing.

TABLE 1

| Ex. No. | Antiseptic | Wt-% | Vehicle | Wt-% | Enhancer | Wt-% | Surfactant | Wt-% |
|---|---|---|---|---|---|---|---|---|
| 1 | Propylene glycol monocaprylate* | 40 | Olive oil | 58.5 | Mandelic acid | 1.5 | NA | NA |
| 2 | Glycerol monolaurate | 5 | FINSOLV TN* | 89 | Benzoic acid | 1 | PLURONIC | 1 |
|   |   |   | Ethanol* | 5 |   |   |   |   |
| 3 | Propylene glycol monocaprylate | 2 | Water | 96.8 | BHT | 0.1 | PLURONIC | 1 |
|   |   |   |   |   | EDTA | 0.1 |   |   |
| 4 | 2-ethylhexy glycerin ether* | 99 | NA | NA | Mandelic acid | 1 | NA | NA |

NA—not applicable
*These components may also function as penetration agents.

Example 5

MIC Testing with *Streptococcus pneumoniae* Type 3

Minimal inhibitory concentrations (MIC) were determined by means of agar dilution according to procedures such as those described in National Committee for Clinical Laboratory Standards (1993); *Methods for Dilution Antimicrobial Susceptibility Tests for Bacteria That Grow Aerobically—Third Edition: Approved Standard M7-A3*. NCCLS, Villanova, Pa. Ten fold dilutions were made for all compounds from 1/10 to 1/10,000. Example 1-4 compositions had an MIC in the range of 1/1000 dilution.

A second experiment was performed beginning with the 1/100 dilutions of each compound and measured the CFU/mL at the dilutions. The results of those tests are presented in Table2 a-d below for dilutions of the Example solutions of 1/100, 1/500, 1/1000, and 1/5000. The initial inoculation was with $1 \times 10^6$/mL of organism. The samples were incubated at 37° C. in a 7% carbon dioxide incubator, stationary. The concentration of organisms present were determined at 0, 0.5, 1.5, 3, and 6 hours of incubation. The organism used was *Streptococcus pneumoniae* type 3 with the minimum level of detection of 0.0001 CFU/mL×106. The Control columns represent organism growth with no antimicrobial composition present. The numbers were rounded to the nearest whole number.

TABLE 2a

Example 1 with *Streptococcus pneumoniae* type 3

| CFU/mL × $10^6$ | | Example 1 Dilution levels | | | | |
|---|---|---|---|---|---|---|
| Time (hr) | Control | 1/100 | 1/500 | 1/1000 | 1/5000 | 1/10000 |
| 0 | 1 | 1 | 1 | 1 | 1 | 1 |
| 0.5 | 1 | 0.1 | 1 | 1 | 1 | 1 |
| 1.5 | 2 | 0.0001 | 0.0001 | 0.2 | 2 | 0.2 |
| 3 | 10 | 0.0001 | 0.0001 | 5 | 10 | 5 |
| 6 | 40 | 0.0001 | 0.0001 | 40 | 50 | 40 |

TABLE 2b

Example 2 with *Streptococcus pneumoniae* type 3

| CFU/mL × $10^6$ | | Example 2 Dilution levels | | | |
|---|---|---|---|---|---|
| Time (hr) | Control | 1/100 | 1/500 | 1/1000 | 1/5000 | 1/10000 |
| 0 | 1 | 1 | 1 | 1 | 1 | 1 |
| 0.5 | 1 | 0.1 | 1 | 1 | 1 | 1 |
| 1.5 | 2 | 0.0001 | 0.0001 | 1 | 2 | 0.2 |
| 3 | 10 | 0.0001 | 0.0001 | 10 | 10 | 5 |
| 6 | 40 | 0.0001 | 0.0001 | 40 | 40 | 40 |

TABLE 2c

Example 3 with *Streptococcus pneumoniae* type 3

| CFU/mL × $10^6$ | | Example 3 Dilution levels | | | |
|---|---|---|---|---|---|
| Time (hr) | Control | 1/100 | 1/500 | 1/1000 | 1/5000 | 1/10000 |
| 0 | 1 | 1 | 1 | 1 | 1 | 1 |
| 0.5 | 1 | 0.1 | 1 | 1 | 1 | 1 |
| 1.5 | 2 | 0.0001 | 0.02 | 1 | 2 | 2 |
| 3 | 10 | 0.0001 | 0.5 | 10 | 10 | 10 |
| 6 | 40 | 0.0001 | 40 | 40 | 40 | 40 |

TABLE 2d

Example 4 with *Streptococcus pneumoniae* type 3

| CFU/mL × $10^6$ | | Example 4 Dilution levels | | | |
|---|---|---|---|---|---|
| Time (hr) | Control | 1/100 | 1/500 | 1/1000 | 1/5000 | 1/10000 |
| 0 | 1 | 1 | 1 | 1 | 1 | 1 |
| 0.5 | 1 | 0.0001 | 0.002 | 1 | 1 | 1 |
| 1.5 | 2 | 0.0001 | 0.0001 | 0.1 | 2 | 2 |
| 3 | 10 | 0.0001 | 0.0001 | 0.009 | 10 | 10 |
| 6 | 40 | 0.0001 | 0.0001 | 0.001 | 40 | 40 |

The Tables (2a-d) show the effect of the Example formulations as compared to growth with no compound present (Control). The results in the tables indicate that the antimicrobial compositions of Examples 1, 2, and 4 were bactericidal after 1.5 hours of exposure at a 1/500 dilution with no recoverable organisms. The composition of Example 3 was bactericidal at 1.5 hours at a dilution of 1/100 with no recoverable organisms. The composition of Example 4 was bactericidal at a 1/100 dilution after only 30 minutes of exposure having no recoverable organisms.

Example 6

MIC Testing with *Haemophilus influenzae*

Bacterial kill rates levels determined as described in Example 5, however, the organism used was nontypable *Haemophilus influenzae* in Todd Hewitt media with supplements of NAD and Hemin. Example formulations 1, 2, and 4 were tested with the results presented below in Table 3a-c.

TABLE 3a

Example 1 with nontypable *Haemophilus influenzae*

| CFU/mL × $10^6$ | | Example 1 Dilution levels | | |
|---|---|---|---|---|
| Time (hr) | Control | 1/00 | 1/500 | 1/1000 |
| 0 | 2 | 2 | 2 | 2 |
| 0.5 | 2 | 0.2 | 1 | 2 |
| 1.5 | 3 | 0.005 | 0.3 | 3 |
| 6 | 10 | 0.0004 | 0.05 | 9 |

TABLE 3b

Example 2 with nontypable *Haemophilus influenzae*

| CFU/mL × $10^6$ | | Example 2 Dilution levels | | |
|---|---|---|---|---|
| Time (hr) | Control | 1/00 | 1/500 | 1/1000 |
| 0 | 2 | 2 | 2 | 2 |
| 0.5 | 2 | 0.09 | 1 | 2 |
| 1.5 | 3 | 0.002 | 0.1 | 3 |
| 6 | 10 | 0.0001 | 0.009 | 9 |

TABLE 3c

Example 4 with nontypable *Haemophilus influenzae*

| CFU/mL × $10^6$ | | Example 4 Dilution levels | | |
|---|---|---|---|---|
| Time (hr) | Control | 1/00 | 1/500 | 1/1000 |
| 0 | 2 | 2 | 2 | 2 |
| 0.5 | 2 | 0.09 | 1 | 2 |
| 1.5 | 3 | 0.002 | 0.1 | 3 |
| 6 | 10 | 0.0001 | 0.009 | 9 |

Table 3a-c show the Example formulations effectively killed the nontypable *Haemophilus influenzae*.

Example 7

Testing with *Streptococcus pneumoniae* Type 3 in Wiffle Ball Fluid

Fluid was collected using a procedure similar to that described in Lab Anim Sci. 1992 June; 42(3):307-11, "Evaluation of a subcutaneously implanted chamber for antibody production in rabbits," Clemons D J, Besch-Williford C, Steffen E K, Riley L K, Moore D H. The fluid represented a complex biological fluid containing enzymes, inflammatory cells, among other components and presented a complex fluid similar to that found within an inflamed ear. A sterilized plastic Wiffle golf ball that had been surgically implanted in the subcutis of the thoracic region of a rabbit was inoculated with 1 mL test solutions containing *Streptococcus pneumoniae* type 3 via a percutaneous injection into the core of the ball through one of the perforations in the chamber wall. Rabbits bearing chambers were inoculated with organism. Fluid was withdrawn and tested against Example compositions at a 1/100 level dilution of test compounds (Example 1, 2 and 4) as well as a control with no compound and only organism. The inoculated chambers were maintained in the rabbit and samples of fluid from the Wiffle ball chamber were removed at 2, 4, and 6 hours and concentration of organisms determined. This was compared to the organism level in fluid samples treated with the test formulation at 2, 4 and 6 hours after treatment The results are presented in Table 4a-c.

TABLE 4a

Example 1 in Rabbit fluid with *Streptococcus pneumoniae* type 3

| | CFU/mL × $10^6$ | Example 1 |
|---|---|---|
| Time (hr) | Control | 1/100 Dilution |
| 0 | 1.5 | 1.5 |
| 2 | 1.7 | 0.0001 |
| 4 | 9.2 | 0.0001 |
| 6 | 35 | 0.0001 |

TABLE 4b

Example 2 in Rabbit fluid with *Streptococcus pneumoniae* type 3

| | CFU/mL × $10^6$ | Example 2 |
|---|---|---|
| Time (hr) | Control | 1/100 Dilution |
| 0 | 1.5 | 1.5 |
| 2 | 1.6 | 0.0001 |
| 4 | 8.8 | 0.0001 |
| 6 | 37 | 0.0001 |

TABLE 4c

Example 4 in Rabbit fluid with *Streptococcus pneumoniae* type 3

| | CFU/mL × $10^6$ | Example 4 |
|---|---|---|
| Time (hr) | Control | 1/100 Dilution |
| 0 | 1.5 | 1.5 |
| 2 | 1.5 | 0.0001 |
| 4 | 9.8 | 0.0001 |
| 6 | 43 | 0.0001 |

The data in these tables indicate that the control samples show substantial growth of the microorganisms. The antimicrobial compositions show excellent bactericidal activity in a complex biological fluid environment.

Example 8

Toxicity Test of Examples 1, 2 and 4

Vaginal epithelial cell toxicity tests were run on Example 1, 2 and 4 and all showed no toxicity in this test.

Example 9

Detection of Transport through the Tympanic Membrane

Example 2 formulation was evaluated for transportability across the ear drum (tympanic membrane) and into the middle ear with an animal model test using chinchillas (400 g to 500 g). A cotton plug saturated with Example 2 formulation was placed against the outer ear membrane of a chinchilla. An opening was made into the middle ear through the bulla and 1 mL saline was placed in the middle ear. At 15, 30, and 60 min. the saline was withdrawn and replaced with fresh saline. Tympanometry was completed before and after the test compositions were applied to ensure the tympanic membrane was intact (without perforations). The saline samples were kept at 4° C. until assayed.

GC Analysis: Six samples of saline recovered from the middle ear of a chinchilla were analyzed by GC. They were recovered from both the left and right ears of the test animal at 15, 30, and 60 min after an antibacterial formulation was placed in the outer ear next to the tympanic membrane. The GC analysis detected the formulation components of GML, FINSOLV NT, and benzoic acid.

Standard preparation: A single external standard of GML (Medchem—97%) at 1 mg/mL was prepared in $CHCl_3$. Standards of methyl benzoate and FINSOLV NT were also available. Saline (0.9% NaCl) was prepared in the lab.

Sample Extraction: The six samples were contained in 1.5 mL clear plastic micorcentrifuge tubes. The 30- and 60-min samples were clear while the 15-min samples contained a water insoluble residue (there appeared to be so much antimicrobial composition in the sample collected a separate phase was noted by the analyst). The liquid was vortexed and transferred to separate 10 mL graduated clinical centrifuge tubes and the volume recorded. The sample tubes were rinsed once with approximately 0.5 mL saline vortexed and transferred to the centrifuge tube. The microtubes were rinsed a second time with approximately 0.75 mL chloroform which was also transferred to the clinical centrifuge tube. The chloroform dissolved the residue in the 15 min samples. The liquid level in the centrifuge tubes was brought to 1.7 mL by the addition of saline solution. A sample (4.5 mL) of $CHCl_3$ was then added to the centrifuge tubes using a 5-mL graduated glass pipette. The tubes were then sealed with TEFLON screw cap tops and vortexed for 2 min. They were then centrifuged in an IEC clinical centrifuge until 2 clear phases formed (approximately 5 min). Using Pasture pipettes, the lower (organic) phases were quantitatively transferred to a set of preweighed 7-mlL vials. The extracts were treated with diazomethane (DAM) which formed the methyl esters of acids present, in this case methyl benzoate from benzoic acid present. Extracts were placed on a warm heating block and taken to dryness under a stream of nitrogen. Once constant weight was obtained, the samples were re-weighed and the net weight was recorded. Using a graduated pipette enough $CHCl_3$ was added back to the 15 min extracts to achieve a concentration of 1 mg/mL in GML. The 30 and 60 min samples had much less weight so an arbitrary ½ mL of $CHCl_3$ was added. An aliquot of each sample was then transferred to an autosampler vial and analyzed by GC using the conditions below.

Gas Chromatography:
  Instrument—HP 5890
  Column—15 meter STABILWAX-DA, 0.25 μm film 0.25 mm ID
  Carrier—He, 2.07×$10^5$ N/m²(30 psi) constant pressure
  Injection—2 μL split 1:60, injector temp 250° C.
  Liner—Restek SILTEK deactivated liner with SILTEK deactivated glass wool (catalog number 22406-213.5)
  Program—110° C. initial, 7° C./min to 250°, hold 10 minutes
  Detector—FID at 250° C.

Figure 1B:
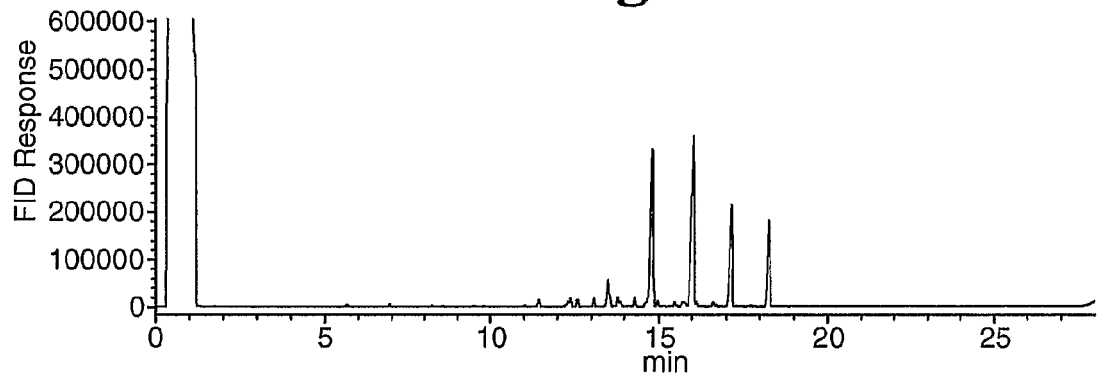
FIG. 1(b) is the GC chromatogram of FINSOLV TN.
Figure 1C:
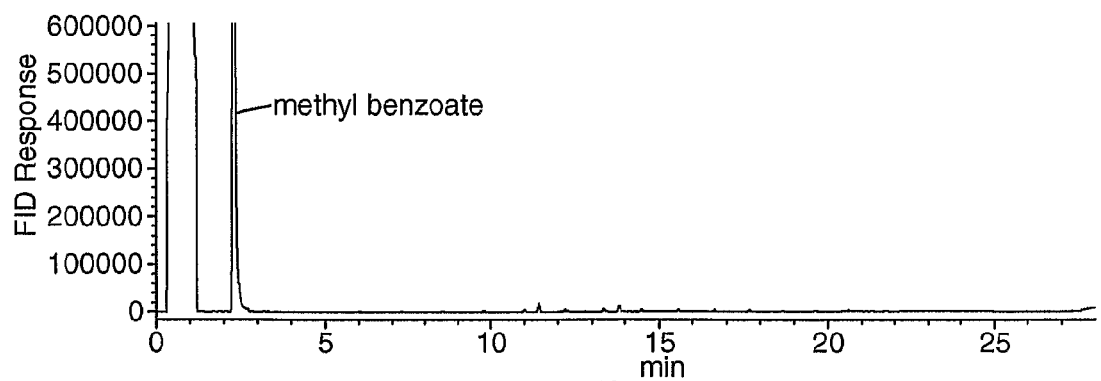
FIG. 1(c) is the GC chromatogram of methyl benzoate.
Figure 1D:
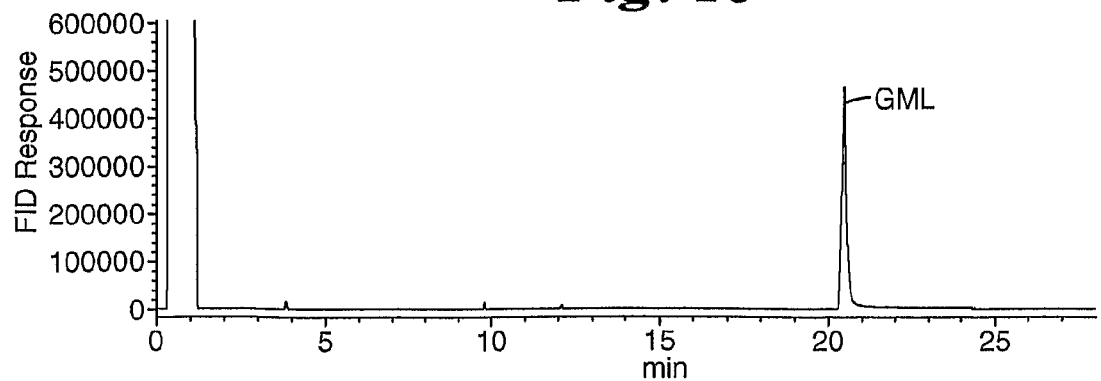
FIG. 1(d) is the GC chromatogram of glycerol monolaurate.

The total recovered GML was determined by direct GC analysis of the fractions. FIG. 1 shows the GC profile of the 15 min extract along with those of the formulation components. As indicated above a standard of methyl benzoate was substituted for benzoic acid. The components have been identified and the FINSOLV TN contributes most of the peak area. Table 5 shows the mg GML recovered at each time point from each ear as well as the totals as determined by GC. Methyl benzoate was also detected which was present because the extract had previously been derivatized with diazomethane (DAM), which formed the methyl ester of any benzoic acid present.

TABLE 5

GML Recovered from Chinchilla Middle Ear

| Time after Application (minutes) | Left ear GML (mg) | Right ear GML (mg) |
|---|---|---|
| 15 | 10.3 | 2.35 |
| 30 | 0.03 | 0.98 |
| 60 | Nd | Nd |
| Total | 10.33 | 3.33 |

Nd—none detected

Most of the material isolated from extraction of the 3 time point samples was in the 15 min samples. The 15 min left ear extract contained 198 mg of a clear, mildly viscous oil and the 15 min right ear extract contained 34 mg of the same oil. In contrast the 30 and 60 min extracts contained much less material and appeared to be dry. It is very surprising that this amount of composition passed into the middle ear so rapidly since the tympanic membrane has been reported to be a formidable barrier to many compositions.

NMR performed on the oil from the left ear at 15 minutes confirmed the presence of FINSOLV TN, methyl benzoate, and alkyl monogylceride. See FIG. 1.

Examples 10-11

Antimicrobial compositions were prepared using the components shown in Table 6a. White petrolatum was heated in a beaker to at least approximately 82° C. In another beaker, glycerin and DOSS were heated until the DOSS was dissolved and this solution was allowed to cool to approximately 82° C. Next, the contents of the first beaker were mixed with the contents of the second beaker with a mixing propeller. Mixing was continued until the mixture cooled to 71° C. at which point the GML was added and mixing continued as the mixture continued to cool. When the mixture had cooled to about 54° C., the lactic acid was added and mixing continued until the composition was about to congeal. Just before the composition congealed at approximately 43° C., the composition was removed from the mixer and poured into ointment jars.

TABLE 6a

| | | Components (weight percent) | | | |
|---|---|---|---|---|---|
| Example No. | GML | Lactic Acid (88%) | DOSS (100%) | Glycerin | White Petrolatum |
| 10 | 3.02 | 1.11 | 0.97 | 9.82 | 85.08 |
| 11 | 3.01 | 1.13 | 0.00 | 10.00 | 85.86 |

The compositions of Examples 10-11 were evaluated using the Antimicrobial Kill Rate Test and the results are shown in Table 6b.

TABLE 6b

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 10 | 3.02 | 3.84 | 6.47 | 3.59 | 5.25 | 5.29 |
| 11 | <3.02 | 3.02 | 3.14 | 2.88 | 3.54 | 3.16 |

The results indicate that the full formulation of Example 10 had good kill against both MRSA (Gram positive) and E. coli (Gram negative) organisms. The log reduction was in excess of 3.5 logs after 5 minutes and 5 logs after 10 minutes. Elimination of the surfactant from the formulation (Example 11) resulted in a significant reduction in antimicrobial efficacy.

Examples 12-16

Antimicrobial compositions were prepared as described in Examples 10-11 using the components shown in Table 7a. Mandelic acid was ground into a fine powder using a mortar and pestle and added to the glycerin and DOSS and heated to about 88° C. for Examples 12 and 13 or added directly to the hot, molten petrolatum at about 82° C. for Examples 14 and 15.

TABLE 7a

| | | Components (weight percent) | | | |
|---|---|---|---|---|---|
| Example No. | GML | Mandelic Acid | DOSS (100%) | Glycerin | White Petrolatum |
| 12 | 3.00 | 1.00 | 1.00 | 10.00 | 85.00 |
| 13 | 3.03 | 0.92 | 0.00 | 10.11 | 85.94 |
| 14 | 3.00 | 1.00 | 1.00 | 0.00 | 95.00 |
| 15 | 3.00 | 1.00 | 0.00 | 0.00 | 96.00 |
| 16 | 2.97 | 0.90 | 0.00 | 0.96 | 95.17 |

The compositions of Examples 12-16 were evaluated using the Antimicrobial Kill Rate Test and the results are shown in Table 7b and 7c.

TABLE 7b

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 12 | 3.6 | 5.7 | 5.9 | 4.0 | 5.6 | 6.1 |
| 13 | 2.8 | 3.9 | 4.3 | 5.7 | 5.6 | 6.0 |
| 14 | 5.0 | 5.8 | 5.4 | 5.4 | 5.8 | 6.3 |
| 15 | 2.4 | 2.6 | 3.6 | 3.2 | 3.3 | 3.7 |
| 16 | 2.3 | 3.1 | 4.1 | 4.0 | 3.9 | 4.7 |

TABLE 7c

| | Pseudomonas ae. (log reduction) | | |
|---|---|---|---|
| Example No. | After 2 minutes | After 5 minutes | After 10 minutes |
| 12 | 4.4 | 6.4 | 6.5 |
| 13 | 3.3 | 4.2 | 5.1 |
| 14 | 4.0 | 4.6 | 5.7 |
| 15 | 2.9 | 2.9 | 3.2 |
| 16 | 2.9 | 3.6 | 3.9 |

Example 12 contained a hydrophilic component (glycerin) and surfactant (DOSS) in addition to the antimicrobial lipid (GML) and enhancer (mandelic acid). This sample had the best antimicrobial activity overall, achieving greater than 5.9 log reduction against all three organisms at 10 minutes. Example 13 contained no surfactant (no DOSS), which led to a decrease in activity over Example 12. Example 14 which contained no hydrophilic component had decreased activity over Example 12 but the effect was not as great as elimination of the surfactant. Example 15 containing no hydrophilic component or surfactant showed relatively poor antimicrobial activity. Addition of only 1% hydrophilic component (Example 16) showed an improvement in antimicrobial activity.

Example 17

An antimicrobial composition was prepared using the components listed in Table 8a. GML, isopropyl isosterate, beeswax and FINSOLV TN were combined in a beaker, heated and stirred with a propeller mixer until a clear solution was obtained. Stirring was continued while cooling the solution to about 48° C. when the lactic acid was added. Stirring and cooling continued until the temperature was 43° C. when the composition was removed from the mixer and poured into the ointment jar.

TABLE 8a

| Example No. | Components (weight percent) | | | | |
|---|---|---|---|---|---|
| | GML | Lactic acid (88%) | White Beeswax | Isopropyl isosterate | FINSOLV TN |
| 17 | 10.00 | 1.00 | 20.00 | 29.00 | 40.00 |

The composition of Example 17 was evaluated using the Antimicrobial Kill Rate Test and the results are shown in Table 8b and 8c.

TABLE 8b

| Example No. | MRSA (log reduction) | | | E. coli (log reduction) | | |
|---|---|---|---|---|---|---|
| | After 2 minutes | After 5 minutes | After 10 minutes | After 2 minutes | After 5 minutes | After 10 minutes |
| 17 | >6.3 | >6.3 | >6.3 | 7.3 | 7.3 | 7.3 |

TABLE 8c

| | Pseudomonas ae. (log reduction) | | |
|---|---|---|---|
| Example No. | After 2 minutes | After 5 minutes | After 10 minutes |
| 17 | 8.0 | 8.0 | 8.0 |

The results indicated that the antimicrobial lipid plus enhancer in a non-petrolatum-based ointment had an exceptional kill rate of MRSA, E. coli, and Pseudomonas ae.

Examples 18-25

Antimicrobial Compositions were prepared as described in Examples 10-11 using the components shown in Table 9a. The surfactants were added like DOSS in Example 10.

TABLE 9a

| Example No. | Components (weight percent) | | | | | | |
|---|---|---|---|---|---|---|---|
| | GML | Lactic acid | Glycerin | Surfactant | | Component | |
| | | | | Type | Amt. | Type | Amt. |
| 18 | 3.00 | 1.00 | 10.00 | CRODAFOS SG | 2.00 | Pet | 84.00 |
| 19 | 3.00 | 1.00 | 10.00 | DOSS (100%) | 2.00 | Pet | 84.00 |
| 20 | 3.00 | 1.00 | 10.00 | POLYSTEP B12 | 2.00 | Pet | 84.00 |
| 21 | 3.00 | 1.00 | 10.00 | MACKAM 50-SB | 2.00 | Pet | 84.00 |
| 22 | 3.00 | 1.00 | 10.00 | HOSTAPUR SAS 93G | 2.00 | Pet | 84.00 |
| 23 | 3.00 | 1.00 | 10.00 | LMDO | 2.00 | Pet | 84.00 |
| 24 | 3.00 | 1.00 | 10.00 | DOSS (100%) | 2.00 | PEG | 84.00 |
| 25 | 3.00 | 1.00 | 10.00 | HOSTAPUR SAS 60 | 2.00 | Pet | 84.00 |

The compositions of Examples 18-25 were evaluated using the Antimicrobial Kill Rate Test and the results are shown in Table 9b.

TABLE 9b

| Example No. | MRSA (log reduction) | | | E. coli (log reduction) | | |
|---|---|---|---|---|---|---|
| | After 2 minutes | After 5 minutes | After 10 minutes | After 2 minutes | After 5 minutes | After 10 minutes |
| 18 | 6.41 | 6.17 | 6.41 | 5.29 | 5.56 | 2.65 |
| 19 | 3.33 | 3.38 | 6.17 | 5.85 | 5.54 | 6.14 |
| 20 | 5.74 | 6.41 | 5.88 | 3.49 | 4.34 | 6.11 |
| 21 | 4.18 | 5.05 | 5.90 | 2.63 | 2.80 | 4.47 |
| 22 | 5.73 | 6.11 | 6.11 | 6.03 | 6.23 | 6.23 |
| 23 | 3.45 | 5.16 | 5.78 | 2.69 | 3.40 | 4.05 |
| 24 | 6.11 | 6.11 | 6.11 | 6.23 | 6.23 | 6.23 |
| 25 | 5.73 | 5.02 | 6.22 | 6.07 | 6.17 | 6.17 |

The results indicated that Examples 18, 22, 24, and 25 had exceptional kill rates (>5 logs) after only 2 minutes against both MRSA and E. coli. The surfactants in these examples were anionic (sulfate, sulfonate, and phosphate). Example 20 also had very a good kill rate; however, the ethoxylation on this surfactant may have contributed to the lower efficacy shown against E. coli at the 2-minute and 5-minute time intervals. Example 19 contained DOSS, which had an exceptional kill rate (>6 logs) against both MRSA and E. coli after 10 minutes of exposure. Examples 21 and 23 contained zwitterionic and amine oxide surfactants, respectively, and the kill rate, while still good, was not as good as that of the anionic surfactants.

Example 26

The preparation of the $C10H_{23}$ Glycerin Ether was a two step process.

First isopropylidene glycerol was prepared by adding 100 grams (g) glycerol, 400 mL acetone, 0.65 g p-toluenesulfonic acid, and 50 g of 3 Å molecular sieves to a 1-liter NALGENE bottle with a cap. Rolling the bottle on a roller for 24 hours mixed the contents of the bottle. Next 0.95 g potassium carbonate ($K_2CO_3$) was added to the contents. The mixture was filtered, passed through an activated alumina column, concentrated on a rotary evaporator, and distilled using a water aspirator to pull a vacuum (boiling point (bp) approximately 100° C.). The final product was then used to prepare glycerol ether.

Second a 1-liter round-bottomed flask was purged with nitrogen and 500 mL xylene, 42 g isopropylidene glycerol, and 53.5 g potassium hydroxide (KOH) were added to the flask. The reaction flask was fitted with an overhead stirrer and a Dean-Stark trap. The contents were heated at reflux for approximately 15 hrs with azeotropic removal of $H_2O$. While continuing to heat at reflux, 61.4 g decyl bromide in 100 mL xylene was added dropwise to the reaction. After the addition was completed, the reaction was heated an additional 24 hrs at reflux. The contents were cooled, transferred to a separatory funnel, washed with deionized water 5 times using 100 mL of water each time, dried over magnesium sulfate (MgSO$_4$), filtered and concentrated on a rotarevaporator. The final product was distilled at reduced pressure (boiling point (bp) was approximately 136° C. at 0.5 millimeter (mm) Hg).

An antimicrobial composition was prepared using the components in Table 10a. The white petrolatum was heated to approximately 93° C. and the DOSS and the glyceryl ether were added to it while stirring using a mixing propeller. The mixture was stirred while being held at 93° C. until a clear solution was formed. The mixture was allowed to start cooling with continuous stirring. When the mixture reached approximately 65° C. the glycerin was added and the cooling and stirring continued. When the mixture reached approximately 49° C. the lactic acid was added and cooling and stirring continued until the composition was about to congeal (approximately 38° C.) and then it was poured into an ointment jar.

TABLE 10a

| Example No. | 88% Lactic Acid | $C_{10}H_{23}$ glycerin ether | 100% DOSS | Glycerin | White petrolatum |
|---|---|---|---|---|---|
| | | Components (weight percent) | | | |
| 26 | 1.13 | 1.46 | 1.02 | 10.07 | 88.94 |

The compositions of Example 26 were evaluated using the Antimicrobial Kill Rate Test and the results are shown in Table 10b.

TABLE 10b

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 26 | 3.16 | 3.70 | 4.51 | 4.68 | 5.88 | 5.47 |

The results indicated that over 3 log reductions after 2 minutes of exposure and over 4.5 log reductions after 10 minutes of exposure occurred for both MRSA and *E. coli* using an antimicrobial glycerin ether in combination with a enhancer (alpha-hydroxy acid).

Example 27

An antimicrobial composition was prepared using the components in Table 11a as described for Examples 10 and 11 but propylene glycol monocaprate was substituted for GML.

TABLE 11a

| | Components (weight percent) | | | | |
|---|---|---|---|---|---|
| Example No. | 88% Lactic Acid | Propylene glycol monocaprate | 100% DOSS | Glycerin | White petrolatum |
| 27 | 1.12 | 3.01 | 1.00 | 9.92 | 84.95 |

The compositions of Example 27 were evaluated using the Antimicrobial Kill Rate Test and the results are shown in Table 11b.

TABLE 11b

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 27 | 6.54 | 6.54 | 6.54 | 5.64 | 5.88 | 5.88 |

The results indicated that the antimicrobial composition containing propylene glycol monocaprate and an enhancer (lactic acid, an alpha-hydroxy acid) achieved an exceptional kill rate against MRSA (over 6 log reduction in 2 minutes) as well as an exceptional kill rate against *E. coli* (over 5.5 log reduction in 2 minutes).

LIPID ESTER EXAMPLES

Examples 28-32 and Comparative A

Antimicrobial compositions were prepared using the antimicrobial lipids and components shown in Table 12. For the formulation that contains IPA, the procedure was as follows. DOSS, PLURONIC P65 and lipid ester were added to IPA and mixed to dissolve forming a solution. Next, EDTA was added to water and the mixture stirred until EDTA dissolved. Then the ester containing IPA solution was added to the resulting water solution to form the test formulation. For formulations that do not contain IPA, the mixing procedure was that the DOSS and EDTA were added to the water and mixed to dissolve and form a solution. PLURONIC was added and the mixture stirred until the PLURONIC dissolved. Finally the ester was added to form the test formulation.

All of the formulations in Table 12 contained 10% PLURONIC in addition to the components listed with water making up the remaining portion of the formulation.

TABLE 12

| Example No. | Ester | Ester purity by GC | Components (Weight percent) | | | |
|---|---|---|---|---|---|---|
| | | | Ester | IPA | DOSS 50% | EDTA |
| 28 | Lauryl Lactate | 48 | 3 | 10 | 1 | 0.2 |
| 29 | Lauryl Lactate | 75 | 3 | 10 | 1 | 0.2 |
| 30 | Lauryl Lactate | 75 | 3 | 0 | 0 | 0 |
| 31 | 2ethylhexyllactate | Nd | 3 | 10 | 1 | 0.2 |
| 32 | 2ethylhexyllactate | Nd | 3 | 0 | 0 | 0 |
| Comparative A | None | Na | 0 | 10 | 1 | 0.2 |

Nd—not determined.
Na—not applicable

The compositions of Examples 28-32 and Comparative A were evaluated using the Antimicrobiol Kill Test and the results are shown in Table 13a-c.

TABLE 13a

Antimicrobial Kill Test Results

| | Log Reduction of *S. aureus* (ATCC 33593) Initial inoculum 7.95 log | | |
|---|---|---|---|
| Example Formulation | After 1 minute | After 3 minutes | After 5 minutes |
| 29 | 4.63 | 4.22 | 5.95 |
| 30 | <2.41* | <2.41* | <2.41* |
| 31 | 4.32 | 5.95 | 5.95 |

TABLE 13a-continued

Antimicrobial Kill Test Results

| Example Formulation | Log Reduction of S. aureus (ATCC 33593) Initial inoculum 7.95 log | | |
|---|---|---|---|
| | After 1 minute | After 3 minutes | After 5 minutes |
| 32 | <2.41* | <2.41* | 3.35 |
| Comparative A | <2.04* | <2.04* | <2.04* |

*The entry of <2.41 or <2.04 resulted from high initial inoculums and lack of antimicrobial activity in the time length tested that lead to colony counts too numerous to count even on the highest dilution plate. This prevented an exact log reduction from being determined. The log reduction was somewhere between 0 and 2 logs. Approximately 2.4 log was the lower limit of detection.

TABLE 13b

Antimicrobial Kill Test Results

| Example Formulation | Log Reduction of E. coli (ATCC11229) Initial inoculum 7.59 log | | |
|---|---|---|---|
| | After 1 minute | After 3 minutes | After5 minutes |
| 28 | <2.04* | <2.04* | <2.04* |
| 31 | 5.59 | 5.59. | 5.59 |
| Comparative A | <2.04* | <2.04* | <2.04* |

.*The entry of <2.04 resulted from high initial inoculums and lack of antimicrobial activity in the time length tested that lead to colony counts too numerous to count even on the highest dilution plate. This prevented an exact log reduction from being determined. The log reduction was somewhere between 0 and 2 logs. Approximately 2 log was the lower limit of detection.

TABLE 13c

Antimicrobial Kill Test Results

| Example Formulation | Log Reduction of E. coli (ATCC11229) Initial inoculum 5.81 log | | | |
|---|---|---|---|---|
| | After 1 minute | After 3 minutes | After 5 minutes | After 10 minutes |
| 29 | <0.27* | <0.27* | <0.27* | 0.38 |
| 30 | <0.27* | <0.27* | <0.27* | <0.27* |
| 32 | 1.49 | 3.58 | 3.39 | 3.81 |

*The entry of <0.27 resulted from high initial inoculums and lack of antimicrobial activity in the time length tested that lead to colony counts too numerous to count even on the highest dilution plate. This prevented an exact log reduction from being determined. The log reduction was somewhere between 0 and 0.27 logs. Approximately 0.27 log was the lower limit of detection.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of treating otitis media in a subject, the method comprising delivering an antimicrobial composition across the tympanic membrane and/or tympanic membrane surrounding tissue to the middle ear by contacting the tympanic membrane, and/or tympanic membrane surrounding tissue with the antimicrobial composition comprising:
an effective amount of an antimicrobial lipid component having a solubility in water of no greater than 1.0 gram per 100 grams deionized water and comprising an antiseptic selected from the group of a (C7-C14)saturated fatty acid monoester of glycerol, a (C7-C14)saturated fatty acid monoester of propylene glycol, a (C8-C22) unsaturated fatty acid monoester of glycerol, a (C8-C22) unsaturated fatty acid monoester of propylene glycol, an alkoxylated derivative of any of the foregoing having a free hydroxyl group, and combinations thereof; wherein the alkoxylated derivative has less than 5 moles of alkoxide per mole of glycerol or propylene glycol; and
an effective amount of a penetration agent, wherein the penetration agent promotes the diffusion of the antimicrobial component into the middle ear;
wherein the fatty acid esters or alkoxylate derivatives thereof comprise less than 15 wt-% di- or tri-esters based on the total weight of the antimicrobial lipid component; and
wherein the viscosity of the composition is less than 20 cps at 23° C.

2. A method of treating otitis media and/or otitis externa in a subject, the method comprising delivering an antimicrobial composition across the tympanic membrane and/or tympanic membrane surrounding tissue to the middle ear by contacting the tympanic membrane, and/or tympanic membrane surrounding tissue with the antimicrobial composition, the composition comprising:
greater than 2 wt-% and less than 6 wt-% of an antimicrobial lipid component having a solubility in water of no greater than 1.0 gram per 100 grams deionized water and comprising an antiseptic selected from the group of a (C7-C14)saturated fatty acid monoester of gylcerol, a (C7-C14)saturated fatty acid monoester of propylene glycol, a (C8-C22)unsaturated fatty acid monoester of glycerol, a (C8-C22)unsaturated fatty acid monoester of propylene glycol, an alkoxylated derivative of any of the foregoing having a free hydroxyl group, and combinations thereof; wherein the alkoxylated derivative has less than 5 moles of alkoxide per mole of glycerol or propylene glycol;
wherein the viscosity of the composition is less than 20 cps at 23° C.

3. A method of treating otitis media in a subject, the method comprising delivering an antimicrobial composition across the tympanic membrane and/or tympanic membrane surrounding tissue to the middle ear by contacting the tympanic membrane, and/or tympanic membrane surrounding tissue with the antimicrobial composition comprising:
an effective amount of an antimicrobial lipid component having a solubility in water of no greater than 1.0 gram per 100 grams deionized water and comprising an antiseptic selected from the group of a (C7-C14)saturated fatty acid monoester of glycerol, a (C7-C14)saturated fatty acid monoester of a propylene glycol, a (C8-C22) unsaturated fatty acid monoester of glycerol, a (C8-C22) unsaturated fatty acid monoester of propylene glycol, an alkoxylated derivative of any of the foregoing having a free hydroxyl group, and combinations thereof; wherein the alkoxylated derivative has less than 5 moles of alkoxide per mole of glycerol or propylene glycol; and
an effective amount of a penetration agent, wherein the penetration agent promotes the diffusion of the antimicrobial component into the middle ear;
wherein the antimicrobial composition is free of antibiotics.

4. A method of treating otitis media in a subject, the method comprising delivering an antimicrobial composition across the tympanic membrane and/or tympanic membrane surrounding tissue to the middle ear by contacting the tympanic membrane, and/or tympanic membrane surrounding tissue with the antimicrobial composition, the composition comprising an effective amount of an antimicrobial lipid component having a solubility in water of no greater than 1.0 gram per 100 grams deionized water and comprising an antiseptic selected from the group of a (C7-C14)saturated fatty monoether of glycerol, a (C7-C14)saturated fatty monoether of propylene glyol, a (C8-C22)unsaturated fatty monoether of glycerol, a (C8-C22)unsaturated fatty monoether of propylene glycol, an alkoxylated derivative of any of the foregoing having a free hydroxyl group, and combinations thereof; wherein the alkoxylated derivative has less than 5 moles of alkoxide per mole of l glycerol or propylene glycol.

5. The method of claim 4, wherein the antimicrobial composition further comprises an effective amount of a penetration agent, wherein the penetration agent promotes the diffusion of the antimicrobial component into the middle ear.

6. The method of claim 4, wherein the viscosity of the composition is less than 20 cps at 23° C.

7. The method of any of claims 1-3, and 4, wherein the antimicrobial composition further comprises a surfactant.

8. The method of any of claims 1 and 3, wherein the penetration agent is present in an amount of at least 2% by weight.

9. The method of any of claims 1-3, and 4, wherein the antimicrobial composition achieves at least 4 log reduction in test bacteria in 10 minutes.

10. The method of any of claims 1-3, and 4, wherein the antimicrobial composition further comprises an enhancer component.

11. The method of any of claims 1 and 3, wherein the penetration agent is selected from the group consisting of lower alcohols, polyols, glycols, sulfoxides, amides, ketones, oleates, lactam compounds, long chain branched or straight chain saturated or unsaturated alcohols having 8-22 carbon atoms, dialkylamino acetates, and admixtures thereof.

12. The method of any of claims 1-3, and 4, wherein the antimicrobial composition is free of antigen.

13. The method of any of claims 1-3 and 4, wherein the antimicrobial composition is buffered to a pH which is less than 7.

* * * * *

UNITED STATES PATENT AND TRADEMARK OFFICE
CERTIFICATE OF CORRECTION

PATENT NO.        : 8,476,319 B2                                     Page 1 of 7
APPLICATION NO.   : 11/908185
DATED             : July 2, 2013
INVENTOR(S)       : Matthew Scholz et al.

It is certified that error appears in the above-identified patent and that said Letters Patent is hereby corrected as shown below:

On the Title Page

Page 4, Column 1 Item (56) (Other Publications)
Line 31, Delete "Perservatives" and insert -- Preservatives --, therefor.
Line 34, Delete "Philidelphia" and insert -- Philadelphia --, therefor.
Line 44, Delete "bacteiuria" and insert -- bacteriuria --, therefor.
Line 49, Delete "Antimicrobil" and insert -- Antimicrobial --, therefor.
Line 53, Delete "dermatologishes" and insert -- dermatologisches --, therefor.
Line 60, Delete "Staphylococus aureas" and insert -- Staphylococcus aureus --, therefor.
Line 64, Delete "Salmoneallae" and insert -- Salmonella --, therefor.

Page 4, Column 2 Item (56) (Other Publications)
Line 1, Delete "Karabra," and insert -- Kabara, --, therefor.
Line 26, Delete "invections"," and insert -- infections", --, therefor.
Line 51, Delete "aureua" and insert -- aureus --, therefor.
Line 56, Delete "Sensive" and insert -- Sensitive --, therefor.
Line 59, Delete "Syndrom" and insert -- Syndrome --, therefor.
Line 59-60, Delete "Staphylococal" and insert -- Staphylococcal --, therefor.
Line 71, Delete "Lipds," and insert -- Lipids, --, therefor.

Page 5, Column 1 Item (56) (Other Publications)
Line 1, Delete ""Aersols,"" and insert -- "Aerosols," --, therefor.
Line 12, Delete "Antibotic" and insert -- Antibiotic --, therefor.
Line 13, Delete "Pseudomonos" and insert -- Pseudomonas --, therefor.
Line 23, Delete "Monoacylglyserol," and insert -- Monoacylglycerol, --, therefor.
Line 27, Delete "Catalzed" and insert -- Catalyzed --, therefor.
Line 30, Delete "Conrtibute" and insert -- Contribute --, therefor.

Signed and Sealed this
Sixth Day of January, 2015

Michelle K. Lee
*Deputy Director of the United States Patent and Trademark Office*

CERTIFICATE OF CORRECTION (continued)
U.S. Pat. No. 8,476,319 B2

Page 5, Column 2 Item (56) (Other Publications)
Line 7, Delete "infectous" and insert -- infectious --, therefor.
Line 32, Delete "Bacteris"," and insert -- Bacteria", --, therefor.

In the Specification

Column 1
Line 7, Delete "Mar. 20," and insert -- Mar. 10, --, therefor.
Line 51, Delete "Haemophilis" and insert -- Haemophilus --, therefor.
Line 51, Delete "catarhalis)" and insert -- catarrhalis) --, therefor.

Column 3
Line 19, Delete "membrante" and insert -- membrane --, therefor.

Column 5
Line 23, Delete "membrante" and insert -- membrane --, therefor.

Column 7
Line 65, Delete "nasoparangyl" and insert -- nasopharyngeal --, therefor.

Column 10
Line 11, Delete "Haemophilis" and insert -- Haemophilus --, therefor.
Line 12, Delete "catarhalis" and insert -- catarrhalis --, therefor.

Column 11
Line 2, Delete "Pseudamonas" and insert -- Pseudomonas --, therefor.
Line 3, Delete "Haemophilis" and insert -- Haemophilus --, therefor.
Line 10, Delete "Haemophilis" and insert -- Haemophilus --, therefor.
Line 10, Delete "catarhalis" and insert -- catarrhalis --, therefor.
Line 22, Delete "Haemophilis" and insert -- Haemophilus --, therefor.
Line 23, Delete "catarhalis," and insert -- catarrhalis, --, therefor.

Column 13
Line 51, Delete "afflications." and insert -- afflictions. --, therefor
Line 59, Delete "afflications" and insert -- afflictions --, therefor.
Line 62, Delete "Esherichia" and insert -- Escherichia --, therefor.
Line 62, Delete "Haemophilis" and insert -- Haemophilus --, therefor.
Line 67, Delete "Haemophilis" and insert -- Haemophilus --, therefor.
Line 67, Delete "catarhalis," and insert -- catarrhalis, --, therefor.

Column 14
Line 5, Delete "auerginosa," and insert -- aeruginosa, --, therefor.
Line 34, Delete "Haemophilis" and insert -- Haemophilus --, therefor.

Column 15
Line 18, Delete "innoculum" and insert -- inoculum --, therefor.
Line 46, Delete "nasopharangyl" and insert -- nasopharyngeal --, therefor.

Column 16
Line 34, Delete "opque" and insert -- opaque --, therefor.

Column 17
Line 60, Delete "nonioinic" and insert -- nonionic --, therefor.
Line 62, Delete "(CRODAPHOS" and insert -- (CRODAFOS --, therefor.
Line 67, Delete "microscrystalline" and insert -- microcrystalline --, therefor.

Column 18
Line 10, Delete "gycols" and insert -- glycols --, therefor.
Line 31, Delete "there of" and insert -- thereof --, therefor.
Line 45, Delete "PEG 110-PEG" and insert -- PEG 10-PEG --, therefor.
Line 67, Delete "trymethoprim," and insert -- trimethoprim, --, therefor.

Column 19
Line 5, Delete "coxacillin," and insert -- cloxacillin, --, therefor.
Line 6, Delete "amoxycillin," and insert -- amoxicillin, --, therefor.
Line 13, Delete "amoxycillin," and insert -- amoxicillin, --, therefor.
Line 26-27, Delete "domeclocycline," and insert -- demeclocycline, --, therefor.
Line 30, Delete "cinocacin," and insert -- cinoxacin, --, therefor.
Line 38, Delete "pheny-l]" and insert -- phenyl] --, therefor.
Line 42-43, Delete "carbaphenern," and insert -- carbapenem, --, therefor.
Line 49, Delete "azinomicyin-A, busucaberin," and insert -- azinomycin-A, bisucaberin, --, therefor.
Line 50, Delete "calichemycin, chromoximycin," and insert -- calicheamicin, chromomycin, --, therefor.
Line 55, Delete "mitoxantorone" and insert -- mitoxantrone, --, therefor.
Line 62, Delete "narbofloxacin," and insert -- marbofloxacin, --, therefor.

Column 20
Line 48, Delete "mono ethers." and insert -- monoethers. --, therefor.

Column 21
Line 2, Delete "(mono laurin)," and insert -- (monolaurin), --, therefor.
Line 3, Delete "(mono caprylin)," and insert -- (monocaprylin), --, therefor.
Line 3, Delete "(mono caprin)" and insert -- (monocaprin) --, therefor.
Line 8, Delete "arachonic" and insert -- arachidonic --, therefor.

Column 23
Line 2, Delete "carpic," and insert -- capric, --, therefor.
Line 20, Delete "allyl" and insert -- alkyl --, therefor.

CERTIFICATE OF CORRECTION (continued)

Column 23
Line 28, Delete "allyl" and insert -- alkyl --, therefor.

Column 25
Line 64-65, Delete "p-isoarnylphenol." and insert -- p-isoamylphenol. --, therefor.

Column 26
Line 3, Delete "terabromo" and insert -- tetrabromo --, therefor.
Line 16, Delete "enjenol." and insert -- eugenol. --, therefor.
Line 46, Delete "Antispetics" and insert -- Antiseptics --, therefor.
Line 55, Delete "benzalkoium" and insert -- benzalkonium --, therefor.

Column 27
Line 54, Delete "be come" and insert -- become --, therefor.

Column 28
Line 41, Delete "1,2-ethan ediyl))," and insert -- 1,2-ethanediyl)), --, therefor.

Column 29
Line 12, Delete "Psuedomonas" and insert -- Pseudomonas --, therefor.

Column 31
Line 24, Delete "4-aminosalyclic acid," and insert -- 4-aminosalicylic acid, --, therefor.

Column 32
Line 66, Delete "enterochlin," and insert -- enterochelin, --, therefor.

Column 35
Line 3, Delete "TPNB" and insert -- TPnB --, therefor.
Line 27, Delete "galacose," and insert -- galactose, --, therefor.

Column 37
Line 13, Delete "aralklyl" and insert -- aralkyl --, therefor.

Column 38
Line 46, Delete "CRODAPHOS" and insert -- CRODAFOS --, therefor.
Line 46, Delete "Parsipanny, N.J.," and insert -- Parsippany, N.J., --, therefor.

Column 40
Line 8, Delete "tymphanic" and insert -- tympanic --, therefor.

Column 41
Line 34, Delete "polyhrydric" and insert -- polyhydric --, therefor.

CERTIFICATE OF CORRECTION (continued)
U.S. Pat. No. 8,476,319 B2

Column 42
Line 14, Delete "suc" and insert -- such --, therefor.

Column 43
Line 12, Delete "isoparafins" and insert -- isoparaffins --, therefor.
Line 16-17, Delete "isoparafins," and insert -- isoparaffins, --, therefor.

Column 44
Line 9, Delete "prilocalne," and insert -- prilocaine, --, therefor.
Line 9-10, Delete "bupivicaine," and insert -- bupivacaine, --, therefor.
Line 13, Delete "mechlofenameate," and insert -- meclofenamate, --, therefor.
Line 14, Delete "nabumeone," and insert -- nabumetone, --, therefor.
Line 15-16, Delete "salsate," and insert -- salsalate, --, therefor.
Line 33, Delete "clortrimazole," and insert -- clotrimazole, --, therefor.
Line 55, Delete "chlorbutanol," and insert -- chlorobutanol, --, therefor.
Line 55, Delete "iodopropylnyl" and insert -- iodopropynyl --, therefor.

Column 47
Line 27, Delete "crystialline" and insert -- crystalline --, therefor.
Line 27-28, Delete "semicrylastalline" and insert -- semicrystalline --, therefor.

Column 49
Line 47-48, Delete "betonite," and insert -- bentonite, --, therefor.
Line 48, Delete "montmorrillonite," and insert -- montmorillonite, --, therefor.

Column 50
Line 47, Delete "Polyquatemium" and insert -- Polyquaternium --, therefor.

Column 51
Line 20, Delete "aqeuous" and insert -- aqueous --, therefor.
Line 37, Delete "Masterisizer" and insert -- Mastersizer --, therefor.
Line 45-46, Delete "Masterisizer" and insert -- Mastersizer --, therefor.
Line 61, Delete "Polyquatemium-4." and insert -- Polyquaternium-4. --, therefor.
Line 65, Delete "Polyquatemium 24" and insert -- Polyquaternium 24 --, therefor.

Column 53
Line 5-6, Delete "dimethyldiallyammonium" and insert -- dimethyldiallylammonium --, therefor.

Column 54
Line 15, Delete "Polyquatemium 37." and insert -- Polyquaternium 37. --, therefor.
Line 17-18, Delete "Polyquatemium 32." and insert -- Polyquaternium 32. --, therefor.
Line 32, Delete "Polyquatemium-16)," and insert -- Polyquaternium-16), -- therefor.

Column 55
Line 13, Delete "alklyl," and insert -- alkyl, --, therefor.
Line 15, Delete "Arsitoflex" and insert -- Aristoflex --, therefor.
Line 62, Delete "(hexlmethacrylate)," and insert -- (hexylmethacrylate), --, therefor.
Line 62, Delete "(isodecl" and insert -- (isodecyl --, therefor.
Line 65, Delete "(octadecl" and insert -- (octadecyl --, therefor.

Column 57
Line 47, Delete "polyacryaltes," and insert -- polyacrylates, --, therefor.
Line 48, Delete "polye(thylene" and insert -- Poly(ethylene --, therefor.
Line 48, Delete "methacryalte" and insert -- methacrylate --, therefor.

Column 59
Line 40, Delete "terephalate, polybuteleneterephalate," and insert -- terephthalate, polybuteleneterephthalate, --, therefor.
Line 45-46, Delete "polybutylene terephalate," and insert -- polybutylene terephthalate, --, therefor.
Line 49, Delete "perflourinated" and insert -- perfluorinated --, therefor.

Column 60
Line 55, Delete "Staphyloccus" and insert -- Staphylococcus --, therefor.

Column 61
Line 26, Delete "Staphyloccus" and insert -- Staphylococcus --, therefor.
Line 26, Delete "Staphylococus" and insert -- Staphylococcus --, therefor.

Column 62
Line 53, Delete "Mayi" and insert -- Mayr --, therefor.
Line 65, Delete "Mallinkrodt" and insert -- Mallinckrodt --, therefor.

Column 63
Line 26, Delete "CRODAPHOS" and insert -- CRODAFOS --, therefor.
Line 26, Delete "Parsipanny," and insert -- Parsippany, --, therefor.
Line 50, Delete "Pheonix" and insert -- Phoenix --, therefor.
Line 51, Delete "Sommerville, NJ" and insert -- Somerville, NJ --, therefor.
Line 52, Delete "2ethylhexyllactate" and insert -- 2-ethylhexyllactate --, therefor.
Line 54, Delete "Isopropal" and insert -- Isopropyl --, therefor.

Column 65
Line 60, Delete "2-ethylhexy" and insert -- 2-ethylhexyl --, therefor.

Column 66
Line 26, Delete "106." and insert -- $10^6$. --, therefor.

CERTIFICATE OF CORRECTION (continued)
U.S. Pat. No. 8,476,319 B2

Column 70
Line 11, Delete "micorcentrifuge" and insert -- microcentrifuge --, therefor.
Line 32, Delete "mlL" and insert -- mL --, therefor.

Column 71
Line 25, Delete "monogylceride." and insert -- monoglyceride. --, therefor.

Column 73
Line 4, Delete "isosterate," and insert -- isostearate, --, therefor.
Line 18, Delete "isosterate" and insert -- isostearate --, therefor.

Column 74
Line 46, Delete "C10H$_{23}$" and insert -- C$_{10}$H$_{23}$ --, therefor.

Column 75
Line 4, Delete "rotarevaporator." and insert -- rotary evaporator. --, therefor.

Column 76
Line 47, Delete "2ethylhexyllactate" and insert -- 2-ethylhexyllactate --, therefor.
Line 48, Delete "2ethylhexyllactate" and insert -- 2-ethylhexyllactate --, therefor.
Line 54, Delete "Antimicrobiol" and insert -- Antimicrobial --, therefor.

In the Claims

Column 78
Line 30, In Claim 2, delete "gylcerol," and insert -- glycerol, --, therefor.

Column 79
Line 9, In Claim 4, delete "glyol," and insert -- glycol, --, therefor.
Line 14, In Claim 4, after "of" delete "l".